(12) United States Patent
Sun et al.

(10) Patent No.: US 8,765,944 B2
(45) Date of Patent: Jul. 1, 2014

(54) COMPOUNDS FOR THE TREATMENT OF HEPATITIS C

(75) Inventors: Li-Qiang Sun, Glastonbury, CT (US); Eric Mull, Guilford, CT (US); Qian Zhao, Wallingford, CT (US); Tao Wang, Farmington, CT (US); Zhongxing Zhang, Madison, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 304 days.

(21) Appl. No.: 13/210,776

(22) Filed: Aug. 16, 2011

(65) Prior Publication Data

US 2012/0213729 A1 Aug. 23, 2012

Related U.S. Application Data

(60) Provisional application No. 61/375,060, filed on Aug. 19, 2010.

(51) Int. Cl.
  *C07D 251/52* (2006.01)
  *A61K 31/53* (2006.01)
  *A61P 31/12* (2006.01)

(52) U.S. Cl.
  USPC .......................... 544/208; 544/209; 514/245

(58) Field of Classification Search
  USPC .................................. 544/208, 209; 514/245
  See application file for complete search history.

(56) References Cited

U.S. PATENT DOCUMENTS

| 4,816,064 A | 3/1989 | Konno et al. |
| 7,163,943 B2 | 1/2007 | Timmer et al. |
| 7,169,785 B2 | 1/2007 | Timmer et al. |
| 2009/0286778 A1 | 11/2009 | Combs et al. |
| 2011/0086858 A1 | 4/2011 | Wang et al. |

FOREIGN PATENT DOCUMENTS

| WO | WO 2004/026881 | 4/2004 |
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO 2010/118367 | 10/2010 |

OTHER PUBLICATIONS

U.S. Appl. No. 13/086,036, filed Apr. 13, 2011, Wang et al.
U.S. Appl. No. 13/086,704, filed Apr. 14, 2011, Wang et al.

*Primary Examiner* — Venkataraman Balasubramanian
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

9 Claims, No Drawings

COMPOUNDS FOR THE TREATMENT OF HEPATITIS C

CROSS-REFERENCE TO RELATED APPLICATIONS

This application claims the benefit of U.S. provisional application Ser. No. 61/375,060 filed Aug. 19, 2010.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S, *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the N52-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

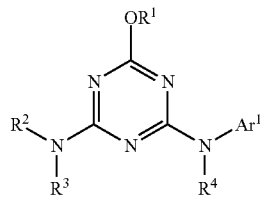

I where
$Ar^2$ is phenyl substituted with 1 $CON(R^5)(R^6)$ or $SON(R^5)(R^6)$ and with 0-3 substituents selected from halo and alkyl;
$Ar^2$ is phenyl substituted with 0-3 substituents selected from halo, alkyl, alkoxy, alkenyl, alkenyloxy, or $CON(R^7)(R^8)$;
$Ar^3$ is phenyl substituted with 0-3 substituents selected from halo, alkyl, and alkoxy;
$Ar^4$ is phenyl or pyridinyl and is substituted with 0-3 substituents selected from halo, alkyl, and alkoxy;
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is alkyl, $(Ar^2)$alkyl, $(Ar^2)$cycloalkyl, or $(R^9)$piperazinyl;
$R^3$ is hydrogen;
$R^4$ is hydrogen;
$R^5$ is $(R^{10})$alkyl, $((R^{10})$cycloalkyl)alkyl, $((R^{10})$alkyl)cycloalkyl, $(((R^{10})$alkyl)cycloalkyl)$, alkylSO$_2$, haloalkylSO$_2$, (cycloalkyl)alkylSO$_2$, alkenylSO$_2$, cycloalkylSO$_2$, (alkyl)cycloalkylSO$_2$, $(R^{10})$alkylSO$_2$, $((R^{10})$cycloalkyl)alkylSO$_2$, $((R^{10})$alkyl)cycloalkylSO$_2$, $(((R^{10})$alkyl)cycloalkyl)SO$_2$, $Ar^4SO_2$, $(R^{11})(R^{12})NSO_2$, or $R^{13}$;
$R^6$ is hydrogen or alkyl;
$R^7$ is alkylSO$_2$, cycloalkylSO$_2$, or $(Ar^3)SO_2$;
$R^8$ is hydrogen or alkyl;
$R^9$ is alkylCO, cycloalkylCO, $(Ar^3)$CO, alkylCO$_2$, cycloalkylCO$_2$, alkylSO$_2$, cycloalkylSO$_2$, or $(Ar^3)SO_2$;
$R^{10}$ is hydrogen, halo, $OR^{14}$, $N(R^{15})(R^{16})$, $CON(R^{17})(R^{18})$, $SO_2N(R^{19})(R^{20})$, or $Ar^4$;
$R^{11}$ is hydrogen or alkyl;
$R^{12}$ is hydrogen or alkyl;
$R^{13}$ is azetidinyl, pyrrolidinyl, piperidinyl, piperazinyl, or morpholinyl, and is substituted with 1 $CON(R^{17})(R^{18})$ and with 0-2 substituents selected from alkyl, alkylCO and alkoxyCO;
or $R^{13}$ is aminoalkyl and is substituted with 1 $CON(R^{17})(R^{18})$ and with 0-2 substituents selected from alkyl, alkylCO and alkoxyCO;
or $R^{13}$ is (imidazolyl)alkyl and is substituted with 1 $CON(R^{17})(R^{18})$ and with 0-1 alkyl substituent;
$R^{14}$ is hydrogen, alkyl, alkylCO, alkoxyCO, alkylaminoCO, or $(Ar^4)NHCO$;

$R^{15}$ is hydrogen, alkyl, cycloalkyl, $(Ar^4)$alkyl, alkylCO, haloalkylCO, alkoxyCO, alkylNHCO, $Ar^4CO$, alkylNHCO, $Ar^4NHCO$, $Ar^4$, (N-BOC-pyrrolidinyl)carboxyl or (N-BOC-piperidinyl)carboxyl;
$R^{16}$ is hydrogen, alkyl;
or $R^{15}$ and $R^{16}$ taken together with the nitrogen to which they are attached is azetidinyl, pyrrolidinyl, piperidinyl, piperazinyl, or morpholinyl, and is substituted with 0-2 substituents selected from alkyl, alkylCO and $Ar^4$;
or $R^{15}$ and $R^{16}$ taken together with the nitrogen to which they are attached is a [1-4.0-3.1-4] bridged bicyclic amine and is substituted with 0-3 substituents selected from alkyl, carboxy, alkoxycarbonyl, and carboxamido;
$R^{17}$ is hydrogen, alkyl, alkylSO$_2$, haloalkylSO$_2$, hydroxyalkylSO$_2$, alkoxyalkylSO$_2$, (cycloalkyl)alkylSO$_2$, alkenylSO$_2$, cycloalkylSO$_2$, (alkyl)cycloalkylSO$_2$, $SO_2N(R^{19})(R^{20})$, $Ar^4$, or $R^{21}$;
$R^{18}$ is hydrogen or alkyl;
or $R^{17}$ and $R^{18}$ taken together with the nitrogen to which they are attached is azetidinyl, pyrrolidinyl, piperidinyl, piperazinyl, or morpholinyl, and is substituted with 0-2 substituents selected from alkyl, alkylCO or $Ar^4$;
or $R^{17}$ and $R^{18}$ taken together with the nitrogen to which they are attached is a [1-4.0-3.1-4] bridged bicyclic amine and is substituted with 0-3 substituents selected from alkyl, carboxy, alkoxycarbonyl, and carboxamido;
$R^{19}$ is hydrogen, alkyl, cycloalkyl, $(Ar^4)$alkyl, alkylCO, haloalkylCO, alkoxyCO, cycloalkylCO, alkylNHCO, $Ar^4CO$, alkylNHCO, $Ar^4NHCO$, $Ar^4$, (N-BOC-piperidinyl)carboxamido, or (N-BOC-pyrrolidinyl)carboxamide;
$R^{20}$ is hydrogen or alkyl;
$R^{21}$ is alkyl or cycloalkyl and is substituted with 1 $CON(R^{22})(R^{23})$ and with 0-2 substituents selected from halo, alkyl, haloalkyl, alkenyl, cycloalkyl, and halocycloalkyl;
$R^{22}$ is hydrogen, alkyl, alkylSO$_2$, haloalkylSO$_2$, hydroxyalkylSO$_2$, alkoxyalkylSO$_2$, (cycloalkyl)alkylSO$_2$, alkenylSO$_2$, cycloalkylSO$_2$, (alkyl)cycloalkylSO$_2$, $SO_2N(R^{19})(R^{20})$, or $Ar^4$; and
$R^{23}$ is hydrogen or alkyl;
or a pharmaceutically acceptable salt thereof.

Another aspect of the invention is a compound of formula I where $R^1$ is haloalkyl or a pharmaceutically acceptable salt thereof.

Another aspect of the invention is a compound of formula I where $R^1$ is trifluoroethyl or a pharmaceutically acceptable salt thereof.

Another aspect of the invention is a compound of formula I where $Ar^2$ is phenyl substituted with 1 $CON(R^5)(R^6)$ and with 0-3 substituents selected from halo and alkyl or a pharmaceutically acceptable salt thereof, or a pharmaceutically acceptable salt thereof.

Another aspect of the invention is a compound of formula I where $R^5$ is alkylSO$_2$, haloalkylSO$_2$, (cycloalkyl)alkylSO$_2$, alkenylSO$_2$, cycloalkylSO$_2$, (alkyl)cycloalkylSO$_2$, $(R^{10})$alkylSO$_2$, $((R^{10})$cycloalkyl)alkylSO$_2$, $((R^{10})$alkyl)cycloalkylSO$_2$, $(((R^{10})$alkyl)cycloalkyl)SO$_2$, $Ar^4SO_2$, or $(R^{11})(R^{12})NSO_2$; or a pharmaceutically acceptable salt thereof.

Another aspect of the invention is a compound of formula I where $R^5$ is $(R^{10})$alkyl, $((R^{10})$cycloalkyl)alkyl, $((R^{10})$alkyl)cycloalkyl, or $(((R^{10})$alkyl)cycloalkyl); $R^{10}$ is $CON(R^{17})(R^{18})$ or $SO_2N(R^{19})(R^{20})$; $R^{17}$ is alkylSO$_2$, haloalkylSO$_2$, hydroxyalkylSO$_2$, alkoxyalkylSO$_2$, (cycloalkyl)alkylSO$_2$, alkenylSO$_2$, cycloalkylSO$_2$, (alkyl)cycloalkylSO$_2$, or $SO_2N(R^{19})(R^{20})$; and $R^{19}$ is alkylCO, haloalkylCO, alkoxyCO, cycloalkylCO, alkylNHCO, $Ar^4CO$, alkylNHCO, or $Ar^4NHCO$; or a pharmaceutically acceptable salt thereof.

Another aspect of the invention is a compound of formula I where $R^5$ is $(R^{10})$alkyl, $((R^{10})$cycloalkyl$)$alkyl, $((R^{10})$alkyl$)$cycloalkyl, or $(((R^{10})$alkyl$)$cycloalkyl$)$; $R^{10}$ is $CON(R^{17})(R^{18})$; $R^{17}$ is $R^{21}$; and $R^{22}$ is alkylSO$_2$, haloalkylSO$_2$, hydroxyalkylSO$_2$, alkoxyalkylSO$_2$, (cycloalkyl)alkylSO$_2$, alkenylSO$_2$, cycloalkylSO$_2$, (alkyl)cycloalkylSO$_2$, or SO$_2$N$(R^{19})(R^{20})$; or a pharmaceutically acceptable salt thereof.

Another aspect of the invention is a compound of formula I where $R^2$ is $(Ar^2)$cycloalkyl substituted with 0-2 substituents selected from halo, alkyl, alkoxy, alkenyl, and alkenyloxy, and substituted with 1 $CON(R^7)(R^8)$; or a pharmaceutically acceptable salt thereof.

Another aspect of the invention is a compound of formula I where $R^2$ is $(Ar^2)$cyclopropyl substituted with 0-2 substituents selected from halo, alkyl, alkoxy, alkenyl, and alkenyloxy, and substituted with 1 $CON(R^7)(R^8)$; or a pharmaceutically acceptable salt thereof.

Another aspect of the invention is a compound of formula I where $N(R^2)(R^3)$ taken together is $(R^9)$piperazinyl or $((R^9)$NH$)$piperidinyl; or a pharmaceutically acceptable salt thereof.

Another aspect of the invention is a compound of formula I where $Ar^1$ is phenyl substituted with 1 $SON(R^5)(R^6)$ and with 0-3 substituents selected from halo and alkyl; or a pharmaceutically acceptable salt thereof.

Another aspect of the invention is a compound of formula I where $R^1$ is trifluoroethyl, or a pharmaceutically acceptable salt thereof.

Another aspect of the invention is a compound of formula I where $R^2$ is $(Ar^2)$cycloalkyl, or a pharmaceutically acceptable salt thereof.

Another aspect of the invention is a compound of formula I where $R^2$ is $(Ar^2)$cyclopropyl, or a pharmaceutically acceptable salt thereof.

Another aspect of the invention is a compound of formula I where $Ar^1$ is phenyl substituted with 1 $CON(R^5)(R^6)$ and with 0-3 substituents selected from halo and alkyl, or a pharmaceutically acceptable salt thereof.

Another aspect of the invention is a compound of formula I where $Ar^2$ is phenyl substituted with 1 $SON(R^5)(R^6)$ and with 0-3 substituents selected from halo and alkyl, or a pharmaceutically acceptable salt thereof.

Any scope of any variable, including $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, Ar^1, Ar^2, Ar^3$, and $Ar^4$, can be used independently with the scope of any other instance of a variable. Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 1 to 6 carbons. "Alkenylene" means a straight or branched divalent alkyl group composed of 2 to 6 carbons with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). Phenylene is a divalent benzene ring. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection Assays.

HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The HCV E1 and E2 envelope coding sequences (genotype 1b) were amplified and isolated from infected patient serum. Media containing pseudoparticles was collected 3 days following transfection, filtered, and stored at −20° C. as a viral stock. Infections were performed in 384-well plates by mixing pseudovirus with 1×10⁴ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and Data Analysis.

Test compounds were serially diluted 3-fold in dimethyl sulfoxide (DMSO) to give a final concentration range in the assay of 50.0 µM to 0.04 µM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A:=0.5-100 nM; B=100-1000 nM; C=1000-5000 nM). Representative data for compounds are reported in Table 1.

TABLE 1

| Examples | $EC_{50}$ (nM) | $EC_{50}$ (nM) |
| --- | --- | --- |
| 1001 | A | |
| 1002 | A | |
| 1003 | A | |
| 1004 | A | 5.3 |
| 1005 | A | |
| 1006 | A | 39 |
| 1007 | A | |
| 1008 | A | 81 |
| 1009 | A | |
| 1010 | A | |
| 1011 | A | 0.48 |
| 1012 | A | 0.25 |
| 1013 | A | |
| 1014 | A | |
| 1015 | A | |
| 1016 | A | |
| 1017 | A | |
| 1018 | A | |
| 1019 | A | |
| 1020 | A | |
| 1021 | A | 94 |
| 1022 | A | |
| 1023 | A | |
| 1024 | A | |
| 1025 | A | |
| 1026 | B | 103 |
| 1027 | A | |
| 1028 | A | 60 |
| 1029 | A | |
| 1030 | A | |
| 1031 | A | |
| 1032 | A | |
| 1033 | A | |
| 1034 | A | |
| 1035 | A | |
| 1036 | A | |
| 1037 | A | |
| 1038 | A | |
| 1039 | A | |
| 1040 | A | |
| 1041 | A | |
| 1042 | A | |
| 1043 | A | |
| 1044 | A | |
| 1045 | A | |
| 1046 | A | |
| 1047 | A | |
| 1048 | A | |
| 1049 | A | |
| 1050 | A | |
| 47 | A | |
| 2002 | A | |
| 2003 | B | 293 |
| 2004 | A | |
| 2005 | C | 1270 |
| 2006 | A | |
| 2007 | B | 487 |
| 2008 | A | |
| 2009 | A | 97 |
| 2010 | A | 67 |
| 2011 | A | |
| 2012 | A | |
| 2013 | A | |
| 2014 | A | |
| 2015 | A | |
| 2016 | A | |
| 2017 | A | 3.2 |
| 2018 | A | |
| 2019 | A | |
| 2020 | A | |
| 2021 | A | |
| 2022 | A | |
| 2023 | A | |
| 2024 | A | |
| 2025 | A | |
| 2026 | A | |
| 2027 | A | |
| 2028 | A | |
| 2029 | A | |
| 2030 | A | |
| 2031 | A | |
| 2032 | A | 1.3 |
| 2033 | A | |
| 2034 | A | |
| 2035 | A | |
| 2036 | A | |
| 2037 | A | |
| 2038 | A | |
| 2039 | A | |
| 2040 | A | |
| 2041 | A | |
| 2042 | A | |
| 2043 | A | |
| 2044 | A | |
| 2045 | A | 0.72 |
| 2046 | A | |
| 2047 | A | |
| 2048 | A | |
| 2049 | A | |
| 2050 | A | |
| 2051 | A | |
| 2052 | A | |
| 2053 | A | |
| 2054 | A | |
| 2055 | A | |
| 2056 | A | |
| 2057 | A | |
| 2058 | A | |
| 2059 | A | |
| 2060 | A | |
| 2061 | A | |
| 2062 | A | |
| 2063 | A | 37.9 |
| 2064 | A | |
| 2065 | A | |
| 2066 | A | |
| 2067 | A | |
| 2068 | A | |
| 2069 | A | |
| 2070 | A | |
| 2071 | A | |
| 2072 | A | |

TABLE 1-continued

| Examples | EC$_{50}$ (nM) | EC$_{50}$ (nM) |
|---|---|---|
| 2073 | A | |
| 2074 | A | |
| 2075 | A | |
| 2076 | A | |
| 2077 | A | |
| 2078 | A | |
| 2079 | A | |
| 2080 | A | |
| 2081 | A | |
| 2082 | A | |
| 2083 | A | |
| 2084 | A | 6.0 |
| 2085 | A | |
| 2086 | A | |
| 2087 | A | |
| 2088 | A | |
| 2089 | A | |
| 2090 | A | |
| 2091 | A | |
| 2092 | A | |
| 2093 | A | |
| 2094 | A | |
| 2095 | A | |
| 2096 | A | |
| 3001 | C | |
| 3002 | B | 477 |
| 3003 | B | 822 |
| 3004 | C | 1642 |
| 3005 | C | |
| 3006 | C | 2698 |
| 3007 | C | 2803 |
| 3008 | B | 976 |
| 3009 | C | |
| 4000 | A | |
| 4001 | A | |
| 4002 | A | |
| 4003 | A | |
| 4004 | A | 2.6 |
| 4005 | A | |
| 5000 | A | |
| 5001 | NA | |
| 5002 | A | |
| 6000 | A | |
| 7001 | A | |
| 7002 | A | |
| 7003 | A | |
| 8001 | C | |
| 8002 | C | |
| 8003 | C | |
| 8004 | C | 2977 |
| 8005 | C | |
| 8006 | C | 2988 |
| 8007 | C | 5399 |
| 8008 | C | |
| 8009 | C | |
| 8010 | C | |
| 8011 | A | |
| 8012 | A | |
| 8013 | A | |
| 8014 | A | 12.7 |
| 8015 | A | |
| 8016 | A | |
| 8017 | A | |
| 8018 | A | |
| 8019 | A | |
| 8020 | A | |
| 8021 | A | |
| 8022 | C | |
| 8023 | C | |
| 8024 | C | |
| 8025 | C | |
| 8026 | C | |
| 8027 | C | |
| 8028 | C | 17590 |
| 8029 | C | |
| 8030 | C | |
| 8031 | C | |
| 8032 | C | |
| 8033 | C | 36140 |
| 8034 | C | 22990 |
| 8035 | C | |
| 8036 | C | |
| 8037 | C | |
| 8038 | C | |
| 8039 | NA | |
| 8040 | C | |
| 8041 | C | |
| 8042 | A | |
| 8043 | NA | |
| 8044 | NA | |
| 8045 | NA | |
| 8046 | NA | |
| 8047 | NA | |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Pharmaceuticals Inc., New York, NY |

TABLE 2-continued

| Brand Name | Physiological Class | Type of Inhibitor or Target | Source Company |
|---|---|---|---|
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon - α | Interferon | albumin IFN-α2b | Human Genome Sciences Inc., Rockville, MD |

TABLE 2-continued

| Brand Name | Physiological Class | Type of Inhibitor or Target | Source Company |
|---|---|---|---|
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |

TABLE 2-continued

| Brand Name | Physiological Class | Type of Inhibitor or Target | Source Company |
|---|---|---|---|
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "6" for delta, "δ" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

Example 1001

Preparation of Compound 1001

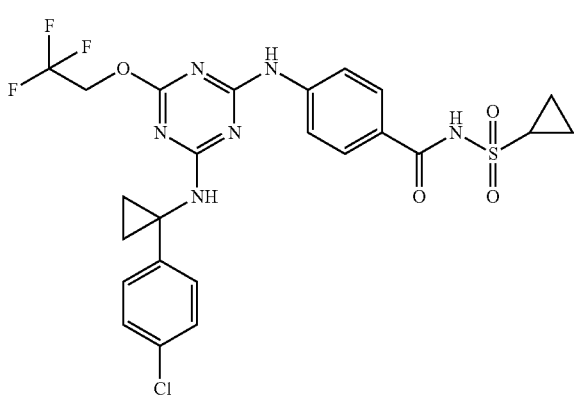

Compound 1001

Scheme 1

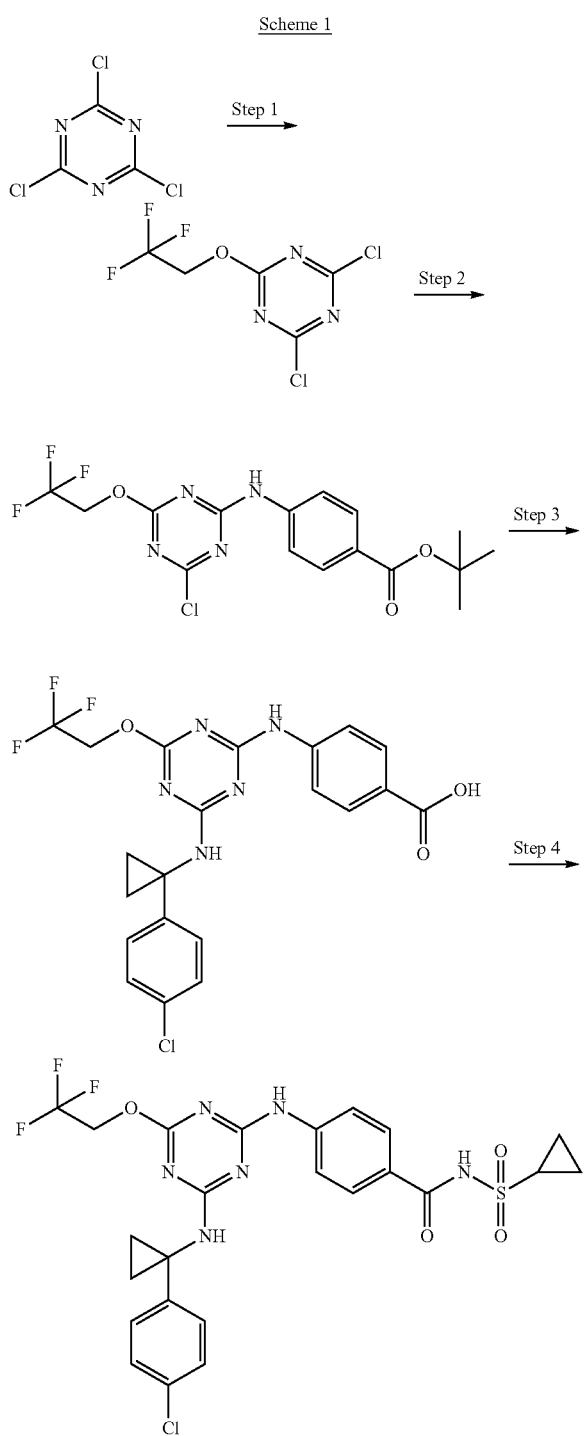

Step 1:
To a solution of 2,4,6-trichloro-1,3,5-triazine (15 g, 81 mmol) in THF (300 mL) was added 2,2,2-trifluoroethanol (8.14 g, 81 mmol) and Hunig's Base (15.63 mL, 89 mmol). The resulting mixture was stirred for 16 h. After removal of most THF and precipitape through a plug washing with THF, the filtrate was concentrate to give a crude that will be used as it is.

Step 2:
To a solution of the product in Step 1 above (10 g, 40.3 mmol) in THF (100 mL) was added tert-butyl 4-aminobenzoate (7.79 g, 40.3 mmol) and Hunig's Base (7.04 mL, 40.3 mmol). The resulting mixture was stirred for 16 h. The precipitate was filtered and washed with $Et_2O$, dried, then washed with water and dried to give 10.6 g of the desired product as a solid. LC-MS (Condition A), MS m/z ($M^+$+H) 405.0.

Step 3:
To a slurry of tert-butyl 4-(4-chloro-6-(2,2,2-trifluoroethoxy)-1,3,5-triazin-2-ylamino)benzoate (3.6 g, 8.89 mmol) and 1-(4-chlorophenyl)cyclopropanamine (1.491 g, 8.89 mmol) in THF (50 mL) was stirred for 5 h at 80° C. The precipitate was filtrated through a plug washing with THF to give acrude product that was purified by Biotage eluting with 4/1-hexane/ethyl acetate to give 1.8 g of tert-butyl 4-(4-(1-(4-chlorophenyl)cyclopropylamino)-6-(2,2,2-trifluoroethoxy)-1,3,5-triazin-2-ylamino)benzoate as a solid. LC-MS (Condition A), MS m/z ($M^+$+H) 536.0. A solution of above tert-butyl 4-(4-(1-(4-chlorophenyl)cyclopropylamino)-6-(2,2,2-trifluoroethoxy)-1,3,5-triazin-2-ylamino)benzoate (4 g, 7.46 mmol) and HCl in dioxane (7.46 ml, 4 M) was stirred for 4 h. Concentration gav 3.58 g of the desired product as a solid, LC-MS (Condition A), MS m/z ($M^+$+H) 480.05.

Step 4:
To a solution of 4-(4-(1-(4-chlorophenyl)cyclopropylamino)-6-(2,2,2-trifluoroethoxy)-1,3,5-triazin-2-ylamino) benzoic acid (20 mg, 0.042 mmol) in DMF (2 mL) solution were added EDCI (16 mg, 0.083 mmol), cyclopropanesulfonamide (10.0 mg, 0.083 mmol) and DMAP (10 mg, 0.083 mmol). The mixture was stirred at room temperature for 16 hs. The residue was purified by prep.HPLC to give Compound 1001 as white solid (9.9 mg, 39%). 1H NMR (400 MHz, MeOD) δ ppm 1.12 (m, 2H), 1.33 (m, 6H), 3.12 (m, 1H), 4.87 (s, 2H), 7.25 (m, 4H), 7.68 (m, 3H), 7.88 (m, 1H); LC-MS (Condition A), MS m/z 583.1 ($M^+$+H).

Example 1002

Preparation of Compound 1002

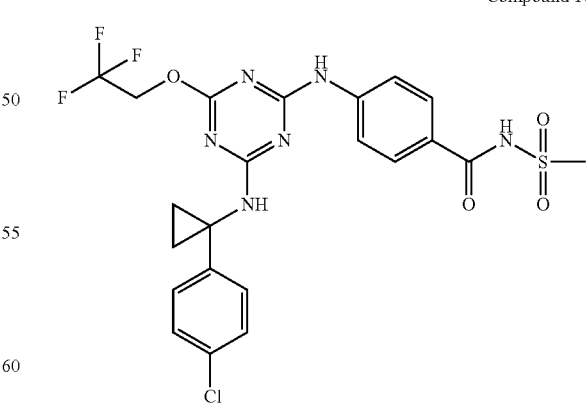

Compound 1002

The Compound 1002 was synthesized following the procedure reported in Example 1001. Methanesulfonamide was used as starting material instead of cyclopropanesulfonamide in step 4. $^1$H NMR (400 MHz, MeOD) δ ppm 1.33 (m, 4H), 3.96 (s, 3H), 4.87 (m, 2H), 7.25 (m, 4H), 7.68 (m, 3H), 7.88 (m, 1H); LC-MS (Condition A), MS m/z 557.0 (M⁺+H).

Example 1003

Preparation of Compounds 1003

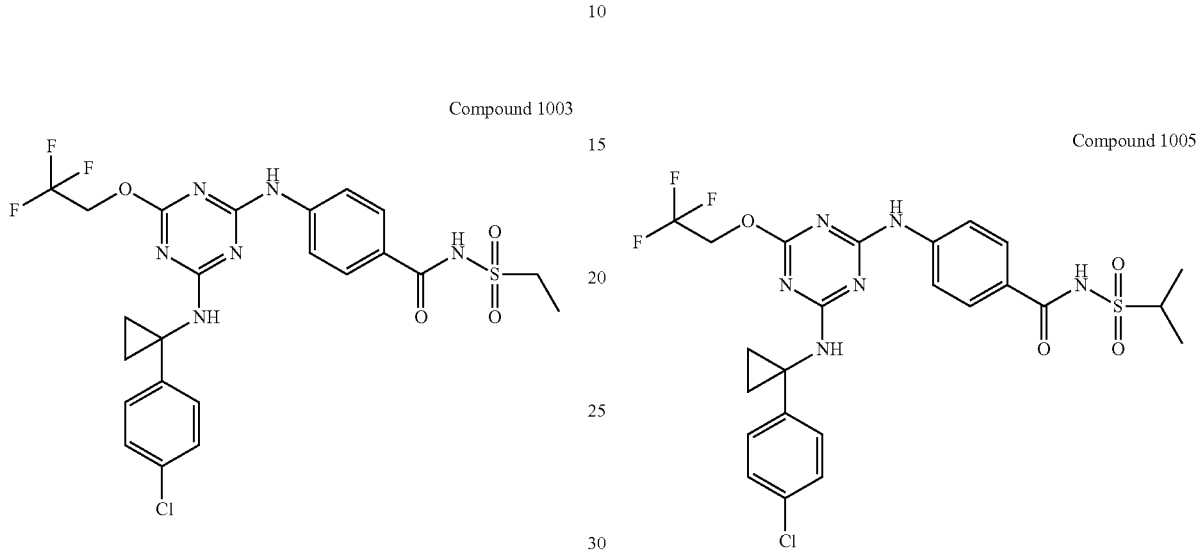

Compound 1003

The Compound 1003 was synthesized following the procedure reported in Example 1001. Ethanesulfonamide was used as starting material instead of cyclopropanesulfonamide in step 4. ¹H NMR (400 MHz, MeOD) δ ppm 1.33 (m, 7H), 3.52 (m, 2H), 4.87 (m, 2H), 7.25 (m, 4H), 7.68 (m, 3H), 7.88 (m, 1H); LC-MS (Condition A), MS m/z 571.1 (M⁺+H).

Example 1004

Preparation of Compounds 1004

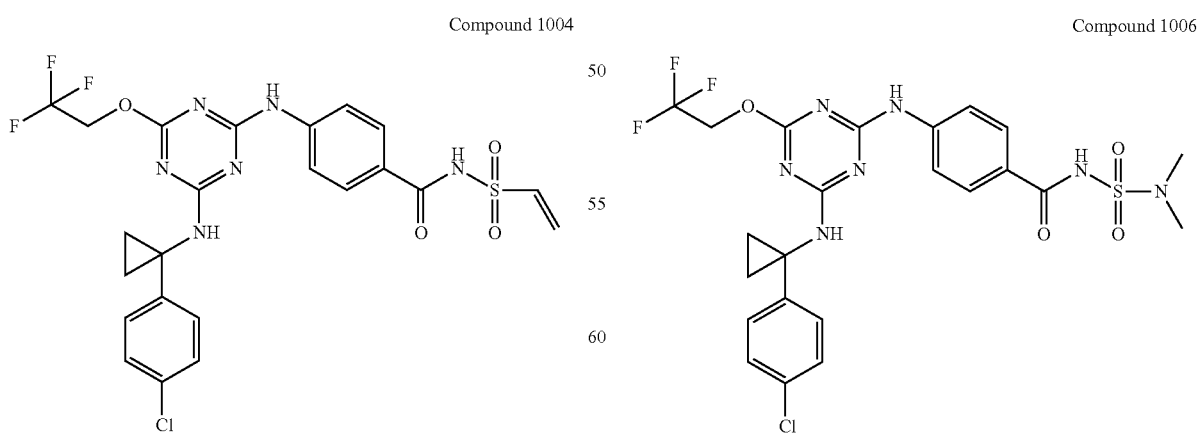

Compound 1004

The Compound 1003 was synthesized following the procedure reported in Example 1001. Ethenesulfonamide was used as starting material instead of cyclopropanesulfonamide in step 4. LC-MS (Condition A), MS m/z 569.0 (M⁺+H).

Example 1005

Preparation of Compounds 1005

Compound 1005

The Compound 1005 was synthesized following the procedure reported in Example 1001. Propane-2-sulfonamide was used as starting material instead of cyclopropanesulfonamide in step 4. LC-MS (Condition A), MS m/z 585.1 (M⁺+H).

Example 1006

Preparation of Compounds 1006

Compound 1006

The Compound 1006 was synthesized following the procedure reported in Step 4 Example 1001. N,N-dimethylsulfamide was used as starting material instead of cyclopropanesulfonamide in step 4. LC-MS (Condition A), MS m/z 586.1 (M⁺+H).

Example 1007

Preparation of Compounds 1007

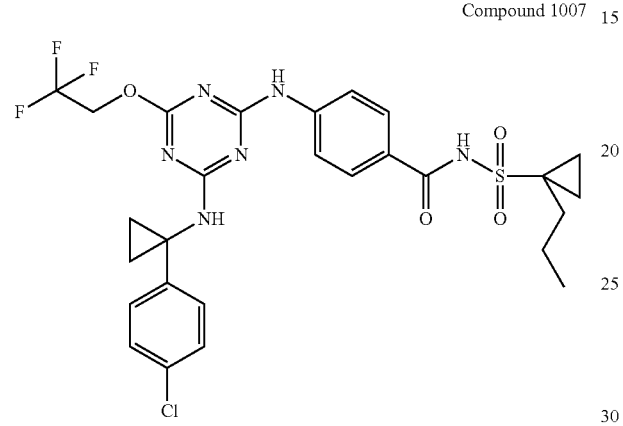

Compound 1007

The Compound 1007 was synthesized following the procedure reported in Example 1001. 1-Propylcyclopropane-1-sulfonamide was used as starting material instead of cyclopropanesulfonamide in step 4. LC-MS (Condition A), MS m/z 625.1 (M⁺+H).

Example 1008

Preparation of Compound 1008

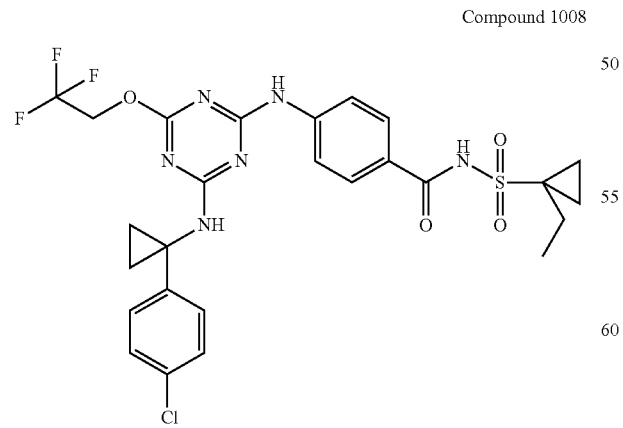

Compound 1008

The Compound 1008 was synthesized following the procedure reported in Example 1001. 1-ethylcyclopropane-1-sulfonamide was used as starting material instead of cyclopropanesulfonamide in step 4. LC-MS (Condition A), MS m/z 611.1 (M⁺+H).

Example 1009

Preparation of Compounds 1009

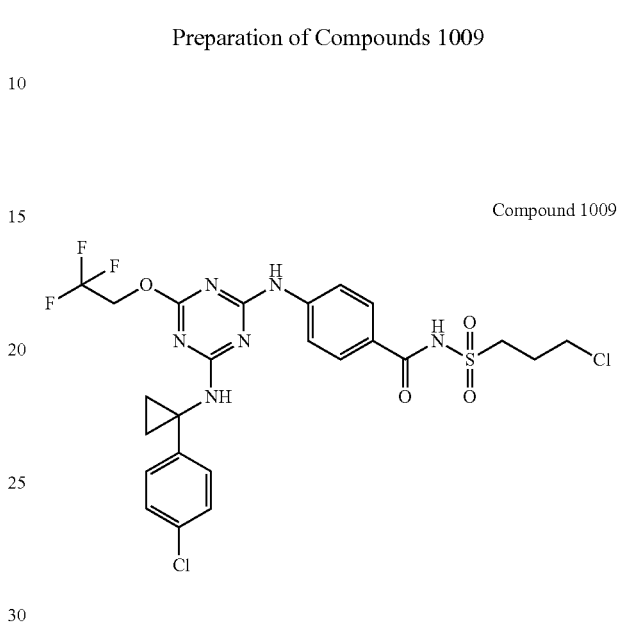

Compound 1009

Compound 1009 was prepared by the same method as Compound 1001 with the following modifications: 3-Chloropropane-1-sulfonamide instead of cyclopropanesulfonamide in Step 4 was used as a starting material to give Compound 1009 (130 mg, 38%). LC-MS (Condition B), MS m/z (M⁺+H) 619.08.

Example 1010

Preparation of Compound 1010

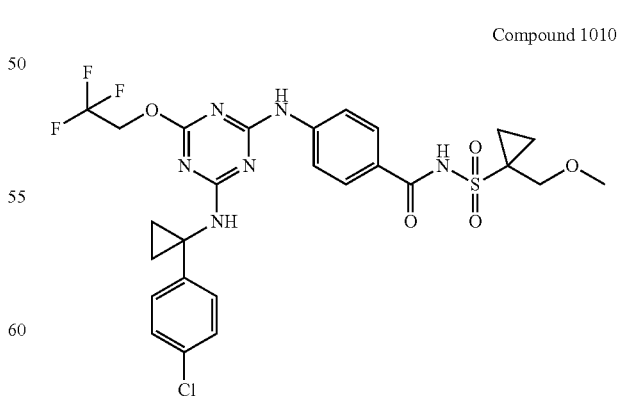

Compound 1010

Compound 1010 was prepared by the same method as Compound 1001 with the following modifications: 1-(Methoxymethyl)cyclopropane-1-sulfonamide instead of cyclopropanesulfonamide in Step 4 was used as a starting material to give Compound 1010 (7 mg, 49%). LC-MS (Condition B), MS m/z (M$^+$+H) 627.27.

Example 1011

Preparation of Compound 1011

Compound 1011

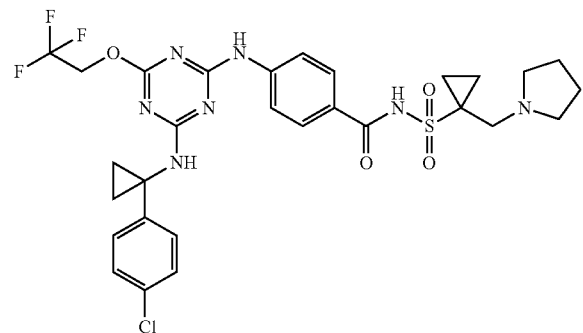

Scheme 1

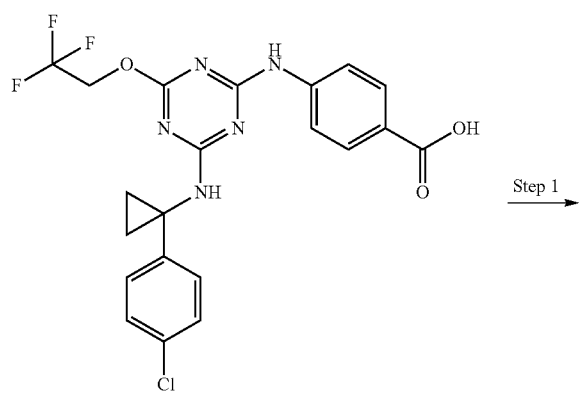

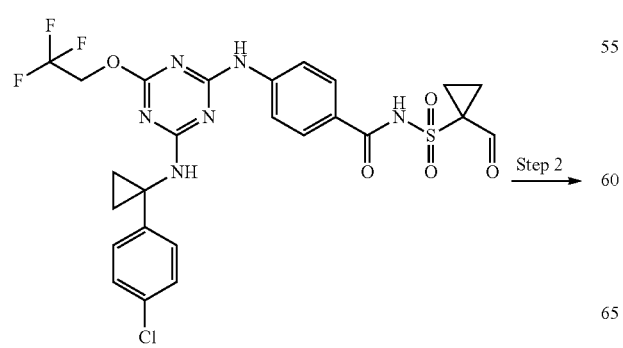

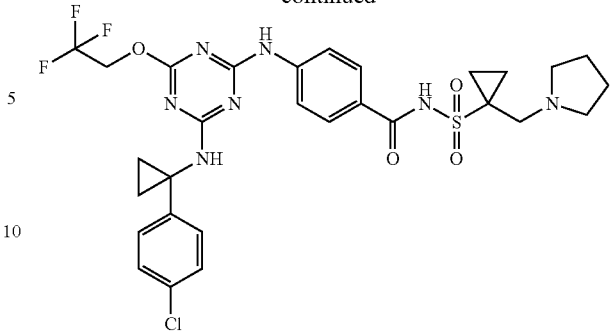

Step 1:
To a solution of 4-(4-(1-(4-chlorophenyl)cyclopropylamino)-6-(2,2,2-trifluoroethoxy)-1,3,5-triazin-2-ylamino)benzoic acid (200 mg, 0.417 mmol), 1-formylcyclopropane-1-sulfonamide, TFA (110 mg, 0.417 mmol), and Hunig's Base (0.364 mL, 2.084 mmol) in CH$_2$Cl$_2$ (10 mL) was added PyBOP (325 mg, 0.625 mmol) and then stirred for 16 h. After concentration, the residue was purified by Biotage to give 200 mg of the product containing some impurity that will be used as it is. LC-MS (Condition B), MS m/z (M$^+$+H) 611.

Step 2:
A stirred solution of 4-(4-(1-(4-chlorophenyl)cyclopropylamino)-6-(2,2,2-trifluoroethoxy)-1,3,5-triazin-2-ylamino)-N-(1-formylcyclopropylsulfonyl)benzamide (30 mg, 0.049 mmol), the product of Step 1, Example 1051, in DCE (3 mL) was treated with pyrrolidine (4.19 mg, 0.059 mmol) followed by NaHB(OAc)$_3$ (31.2 mg, 0.147 mmol). After stirring at rt for 16 h, the reaction was diluted with CH$_2$Cl$_2$ and quenched with NaHCO$_3$, dried over Na$_2$SO$_4$, concentrated and purified by prep HPLC give 22 mg of the desired product as TFA salt. $^1$H NMR (400 MHz, MeOD) δ ppm 1.30-1.39 (m, 4H), 1.61-1.72 (m, 4H), 2.36 (t, J=7.05 Hz, 2H), 3.20 (s, 3H), 3.37 (t, J=6.55 Hz, 2H), 4.85 (m, 2H) 7.19-7.28 (m, 4H), 7.60 (t, J=8.31 Hz, 3H), 7.75-7.85 (m, 1H); LC-MS (Condition B), MS m/z (M$^+$+H) 666.

Example 1012

Preparation of Compound 1012

Compound 1012

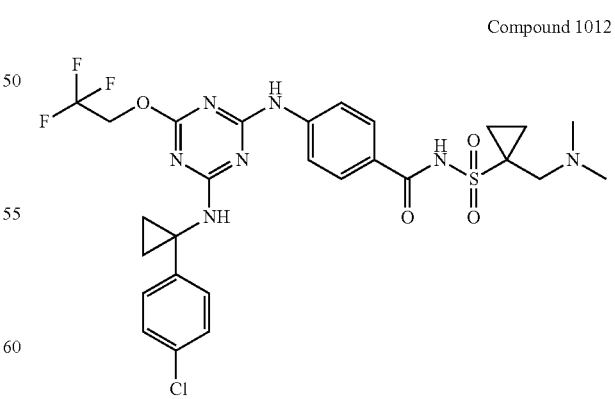

Compound 1012 was prepared by the same method as Compound 1011 with the following modifications: Dimethylamine instead of pyrrolidine in Step 2 was used as a starting material to give Compound 1012 (10 mg, 39%). $^1$H NMR (400 MHz, MeOD) δ ppm 1.02-1.12 (m, 2H), 1.17-1.26 (m, 2H), 1.27-1.38 (m, 4H), 1.61-1.72 (m, 4H), 2.36 (t, J=6.92 Hz, 2H), 2.89-2.96 (m, 1H), 3.37 (t, J=6.55 Hz, 2H), 4.85 (m, 2H), 7.23 (m, 4H), 7.61 (m, 3H), 7.80 (m, 1H); LC-MS (Condition B), MS m/z (M$^+$+H) 640.

Example 1013

Preparation of Compound 1013

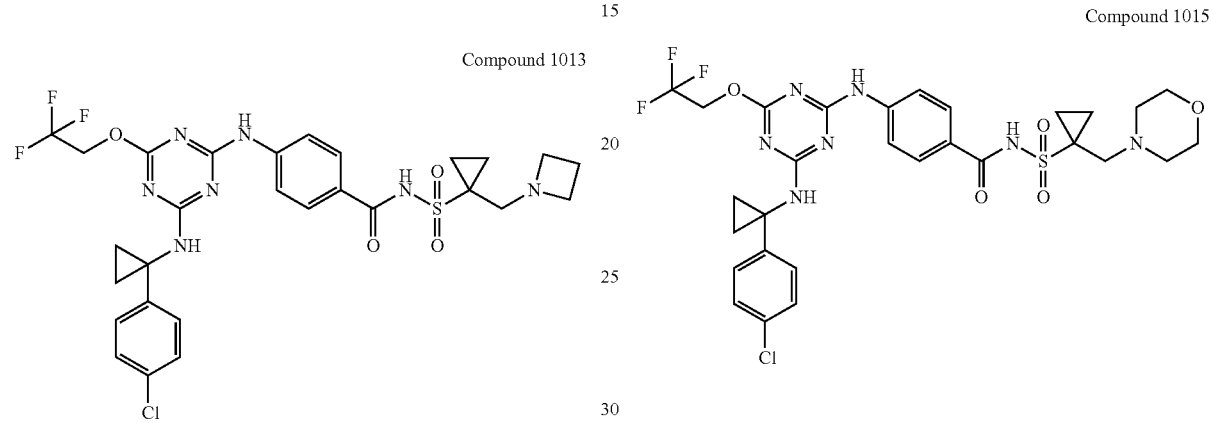

Compound 1013

Compound 1013 was prepared by the same method as Compound 1011 with the following modifications: Azetidine instead of pyrrolidine in Step 2 was used as a starting material to give Compound 1013 (10 mg, 36%). LC-MS (Condition B), MS m/z (M$^+$+H) 652.21.

Example 1014

Preparation of Compound 1014

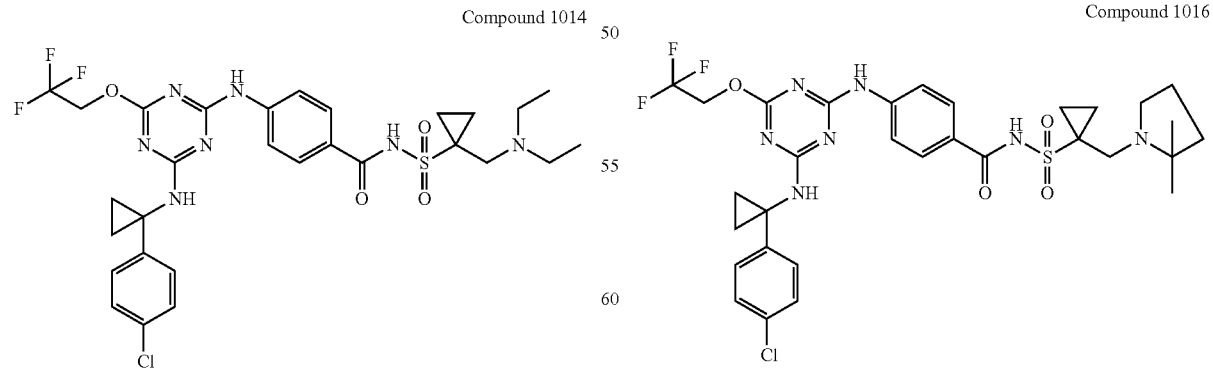

Compound 1014

Compound 1014 was prepared by the same method as Compound 1011 with the following modifications: Diethylamine instead of pyrrolidine in Step 2 was used as a starting material to give Compound 1014 (11 mg, 40%). LC-MS (Condition B), MS m/z (M$^+$+H) 668.24.

Example 1015

Preparation of Compound 1015

Compound 1015

Compound 1015 was prepared by the same method as Compound 1011 with the following modifications: Morpholine instead of pyrrolidine in Step 2 was used as a starting material to give Compound 1015 (22 mg, 78%). LC-MS (Condition B), MS m/z (M$^+$+H) 682.20.

Example 1016

Preparation of Compound 1016

Compound 1016

Compound 1016 was prepared by the same method as Compound 1011 with the following modifications: 2,2-Dimethylpyrrolidine instead of pyrrolidine in Step 2 was used as

Example 1017

Preparation of Compound 1017

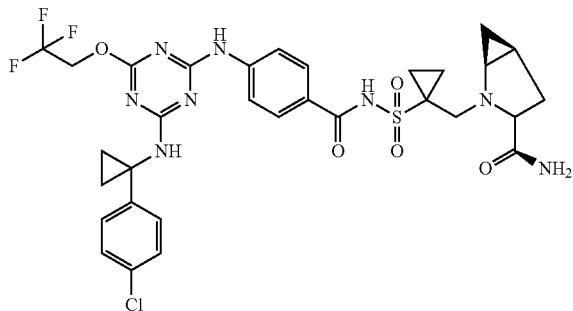

Compound 1017

Compound 1017 was prepared by the same method as Compound 1011 with the following modifications: (1S,3S,5S)-2-Azabicyclo [3.1.0]hexane-3-carboxamide, HCl instead of pyrrolidine in Step 2 was used as a starting material to give Compound 1017 (5 mg, 17%). LC-MS (Condition B), MS m/z (M$^+$+H) 721.33.

Example 1018

Preparation of Compound 1018

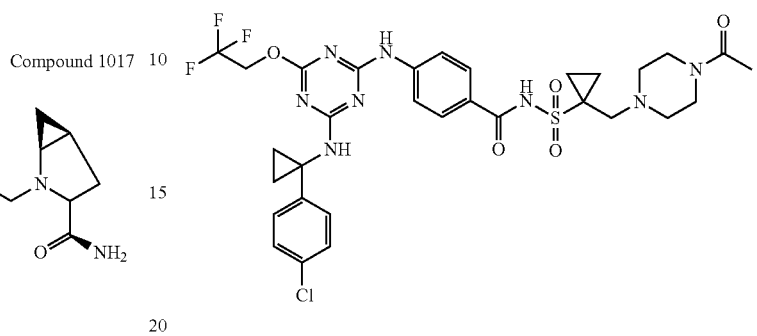

Compound 1018

Compound 1018 was prepared by the same method as Compound 1011 with the following modifications: 1-(piperazin-1-yl)ethanone instead of pyrrolidine in Step 2 was used as a starting material to give Compound 1018 (15 mg, 52%). LC-MS (Condition B), MS m/z (M$^+$+H) 723.36.

Example 1019

Preparation of Compound 1019

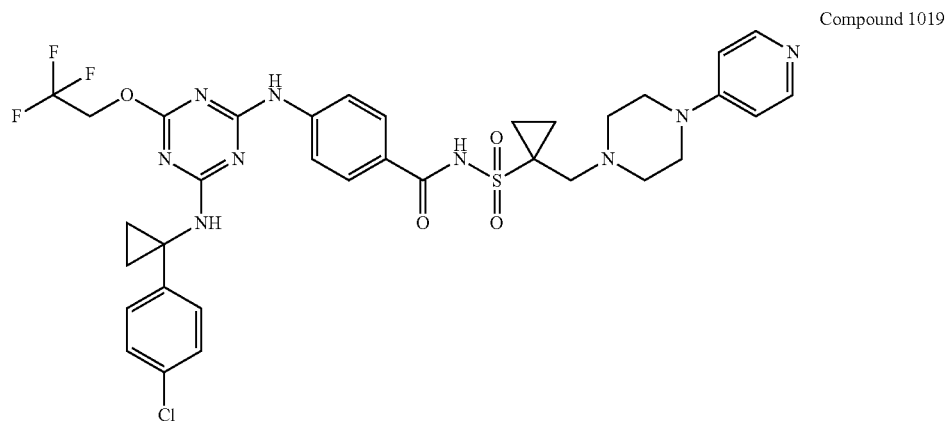 [SMILES: O=C(NS(=O)(=O)C1(CN2CCN(c3ccncc3)CC2)CC1)c1ccc(Nc2nc(NC3(c4ccc(Cl)cc4)CC3)nc(OCC(F)(F)F)n2)cc1]

Compound 1019

Compound 1019 was prepared by the same method as Compound 1011 with the following modifications: 1-(Pyridin-4-yl)piperazine instead of pyrrolidine in Step 2 was used as a starting material to give Compound 1019 (6 mg, 16%). LC-MS (Condition B), MS m/z (M$^+$+H) 758.36.

Example 1020

Preparation of Compound 1020

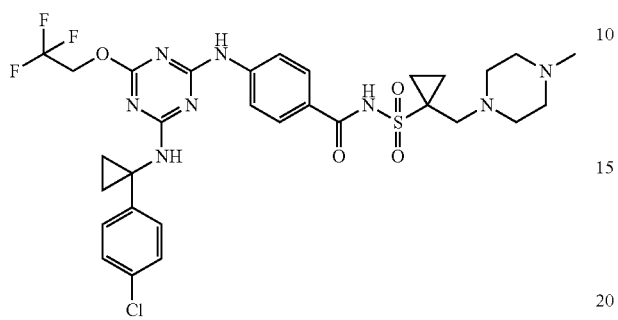

Compound 1020

Compound 1020 was prepared by the same method as Compound 1011 with the following modifications: 1-Methylpiperazine instead of pyrrolidine in Step 2 was used as a starting material to give Compound 1020 (15 mg, 47%). LC-MS (Condition B), MS m/z (M$^+$+H) 695.33.

Example 1021

Preparation of Compound 1021

Compound 1021

Compound 1021 was prepared by the same method as Compound 1011 with the following modifications: N-Methylaniline instead of pyrrolidine in Step 2 was used as a starting material to give compound 1021 (6 mg, 23%). LC-MS (Condition B), MS m/z (M$^+$+H) 702.33.

Example 1022

Preparation of Compound 1022

Compound 1022

Compound 1022 was prepared by the same method as Compound 1011 with the following modifications: N-Methylcyclopropanamine instead of pyrrolidine in Step 2 was used as a starting material to give compound 1022 (8 mg, 30%). LC-MS (Condition B), MS m/z (M$^+$+H) 666.30.

Example 1023

Preparation of Compound 1023

Compound 1023

Compound 1023 was prepared by the same method as Compound 1011 with the following modifications: 3,3-Dimethylpyrrolidine instead of pyrrolidine in Step 2 was used as a starting material to give compound 1023 (7 mg, 23%). LC-MS (Condition B), MS m/z (M++H) 694.35.

Example 1024

Preparation of Compound 1024

Scheme 1

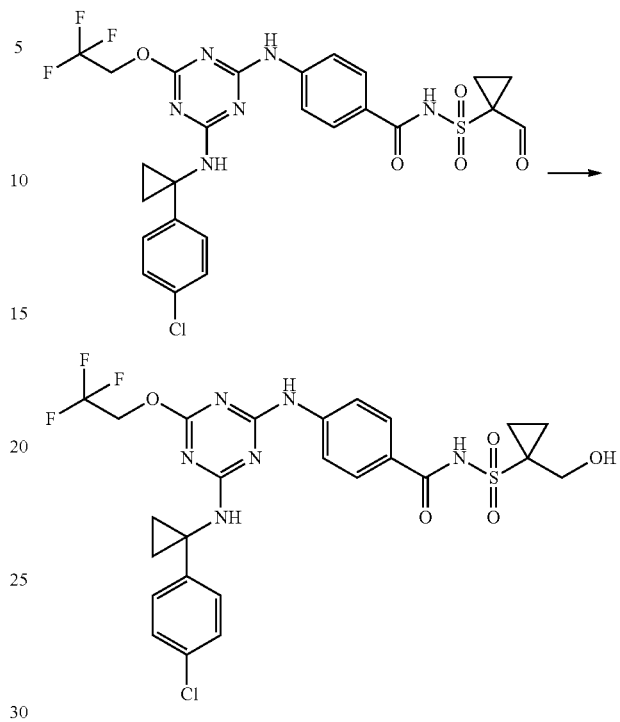

Compound 1024

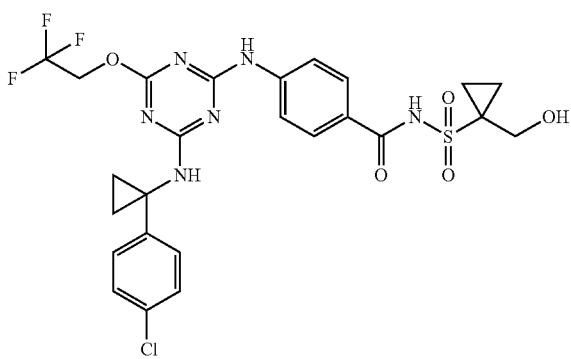

Compound 1024 was prepared by the same method as Compound 1011 with the following modifications: 3-Azabicyclo[3.1.0]hexanee instead of pyrrolidine in Step 2 was used as a starting material to give Compound 1024 (5 mg, 18%). LC-MS (Condition B), MS m/z (M++H) 678.32.

Example 1025

Preparation of Compound 1025

To a solution of 4-(4-(1-(4-chlorophenyl)cyclopropylamino)-6-(2,2,2-trifluoroethoxy)-1,3,5-triazin-2-ylamino)-N-(1-formylcyclopropylsulfonyl)benzamide (50 mg, 0.082 mmol) in CH$_2$Cl$_2$ (5 mL) and MeOH (2.5 mL) was added NaBH$_4$ (12.38 mg, 0.327 mmol) and then stirred for 2 h. The reaction was quenched with 1 N HCl and extracted with ethyl acetate, washed with water, dried over MgSO4, concentrated, purified by prep HPLC to give 40 mg (76%) of the desired product as a solid. LC-MS (Condition B), MS m/z (M++H) 613.12.

Example 1026

Preparation of Compound 1026

Compound 1025

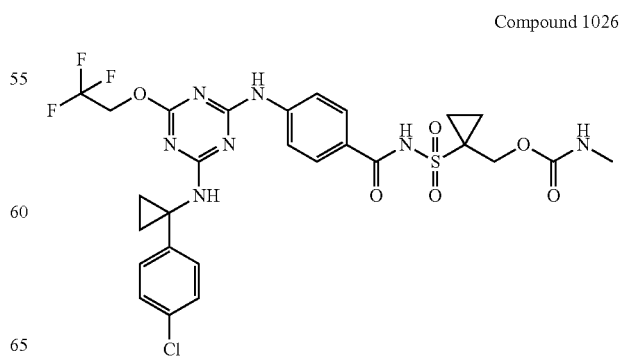

Compound 1026

Scheme 1

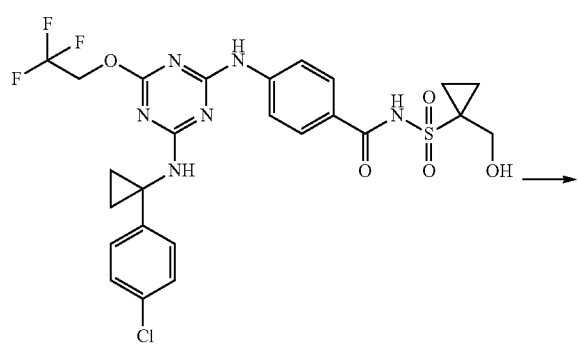

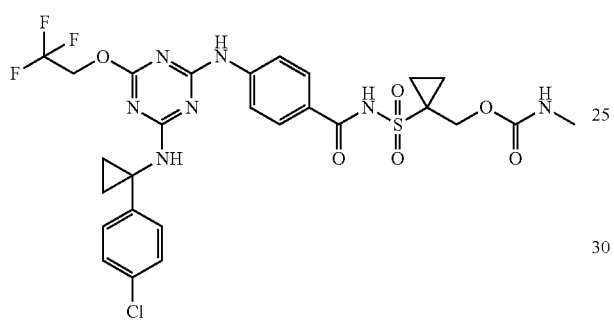

A stirred solution of 4-(4-(1-(4-chlorophenyl)cyclopropylamino)-6-(2,2,2-trifluoroethoxy)-1,3,5-triazin-2-ylamino)-N-(1-(hydroxymethyl)cyclopropylsulfonyl)benzamide (20 mg, 0.033 mmol) in DCE (3 mL) was treated with isocyanatomethane (1.861 mg, 0.033 mmol) followed by Hunig's Base (5.70 μl, 0.033 mmol). After stirring at rt for 16 h, concentration and purification by prep HPLC to give 5 mg (22%) of the desired product as a solid. LC-MS (Condition B), MS m/z (M$^+$+H) 670.28.

Example 1027

Preparation of Compound 1027

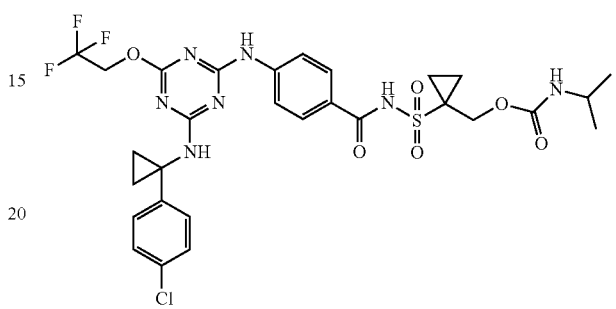

Compound 1027

Compound 1027 was prepared by the same method as Compound 1026 with the following modifications: 2-Isocyanatopropane instead of isocyanatomethane was used as a starting material to give Compound 1027 (13 mg, 54%). LC-MS (Condition B), MS m/z (M$^+$+H) 698.32.

Example 1028

Preparation of Compound 1028

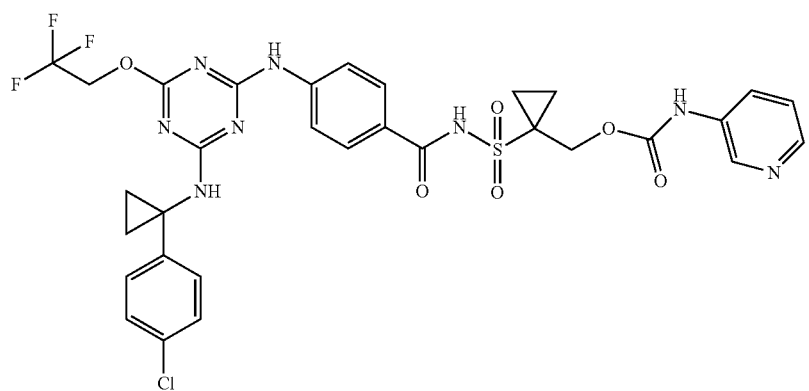

Compound 1028

Compound 1028 was prepared by the same method as Compound 1026 with the following modifications: 3-Isocyanatopyridine instead of isocyanatomethane was used as a starting material to give Compound 1028 (7 mg, 26%). LC-MS (Condition B), MS m/z (M$^+$+H) 733.30.

Example 1029
Preparation of Compound 1029
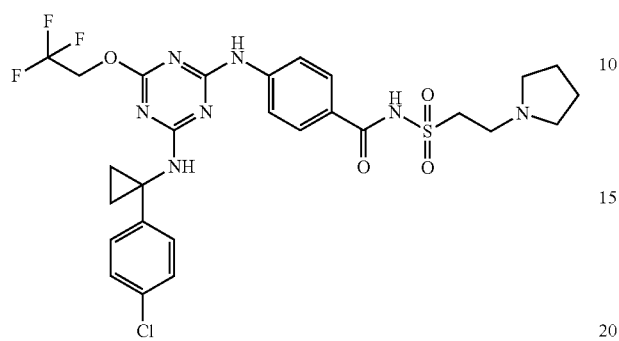
Compound 1029
Scheme 1
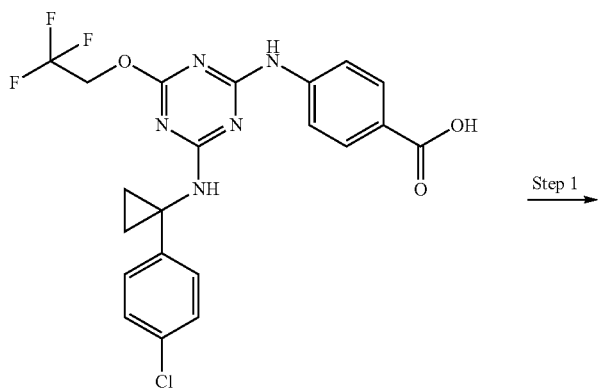
Step 1 →
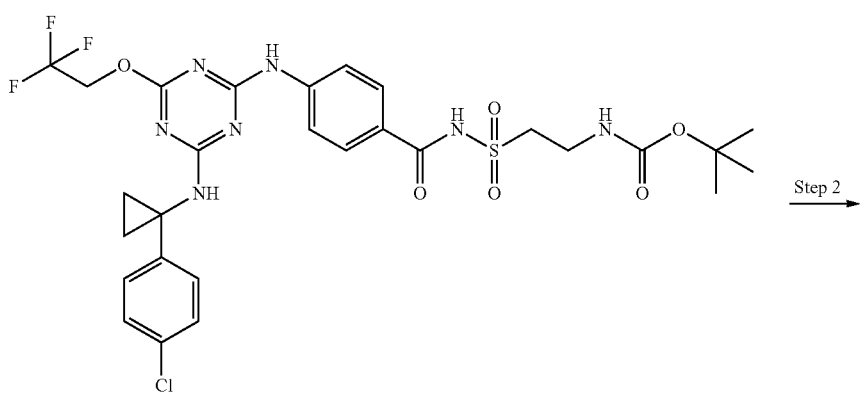
Step 2 →

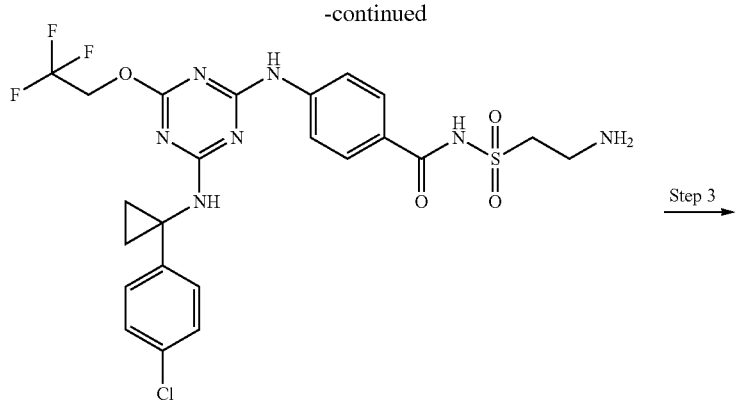

Step 3 →

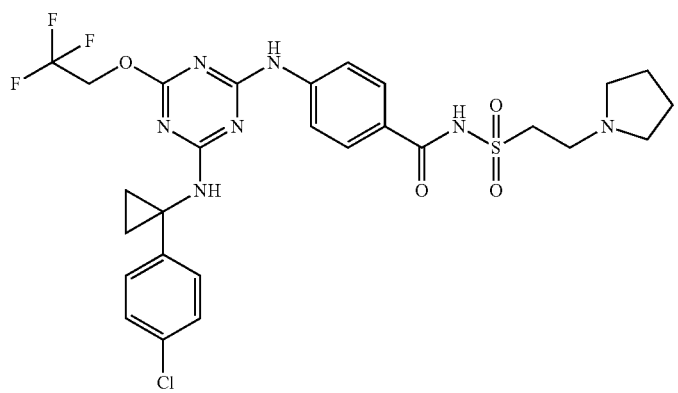

Step 1:

4-(4-(1-(4-chlorophenyl)cyclopropylamino)-6-(2,2,2-trifluoroethoxy)-1,3,5-triazin-2-ylamino)benzoic acid (400 mg, 1.784 mmol), PyBOP (1266 mg, 2.432 mmol), and Hunig's Base (1.416 mL, 8.11 mmol) were stirred in DCM (Volume: 3 mL) for 3 days. The solvent was removed and the crude material was purified by silica gel chromatography using EtOAc followed by 5% MeOH/DCM to give tert-butyl 2-(N-(4-(4-(1-(4-chlorophenyl)cyclopropylamino)-6-(2,2,2-trifluoroethoxy)-1,3,5-triazin-2-ylamino)benzoyl)sulfamoyl)ethylcarbamate (1.1 g). 1H NMR (400 MHz, MeOD) δ ppm 1.27-1.52 (m, 13H), 3.55 (t, J=6.0 Hz, 2H), 3.69 (t, J=5.6 Hz, 2H), 4.83-5.02 (m, 2H), 7.21-7.36 (m, 4H), 7.66-7.82 (m, 3H), 7.89-7.98 (m, 1H); LC-MS (Method A), MS m/z (M$^+$+H) 686.0.

Step 2:

tert-butyl 2-(N-(4-(4-(1-(4-chlorophenyl)cyclopropylamino)-6-(2,2,2-trifluoroethoxy)-1,3,5-triazin-2-ylamino)benzoyl)sulfamoyl)ethylcarbamate (1.1 g, 1.603 mmol) and 4 N HCl in Dioxane (2 mL, 8.00 mmol) were stirred for 1 h then concentrated under vacuum to give N-(2-aminoethylsulfonyl)-4-(4-(1-(4-chlorophenyl)cyclopropylamino)-6-(2,2,2-trifluoroethoxy)-1,3,5-triazin-2-ylamino)benzamide as the HCl salt which was not purified further (410 mg). 1H NMR (400 MHz, DMSO-d$_6$) δ ppm 1.21-1.48 (m, 4H), 3.17-3.31 (m, 2H), 3.83 (t, J=7.2 Hz, 2H), 4.15 (br s, 2H) (NH$_2$), 5.00 (q, J=9.0 Hz, 2H), 7.19-7.39 (m, 4H), 7.69-7.83 (m, 2H), 7.92 (br. s., 3H), 8.86 (br. s., 1H), 10.13 (br. s., 1H); LC-MS (Condition A), MS m/z (M$^+$+H) 586.0.

Step 3:

To a solution of N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol) in Acetonitrile (Volume: 2 mL) was added 1,4-dibromobutane (6.96 mg, 0.032 mmol) and POTASSIUM CARBONATE (21.23 mg, 0.154 mmol). The mixture was heated to 65° C. for 16 h. After cooling to rt, the mixture was diluted with EtOAc, washed with water, and brine. The organic layer was dried over MgSO$_4$ and concentrated. The crude product was purified by rev. phase preparative HPLC (Column: Sunfire prep C18 OBO 5 uM, 30×100 mm by Waters Corp) using a gradient of 20-100% ACN/water w/0.1% TFA modifier to give 4-(4-(1-(4-chlorophenyl)cyclopropylamino)-6-(2,2,2-trifluoroethoxy)-1,3,5-triazin-2-ylamino)-N-(2-(pyrrolidin-1-yl)ethylsulfonyl)benzamide (3 mg) as the TFA salt. 1H NMR (400 MHz, DMSO-d$_6$) δ ppm 1.17-1.48 (m, 4H), 1.80-2.12 (m, 4H), 3.37-4.41 (m, 8H), 5.00 (q, J=9.0 Hz, 2H), 7.15-7.44 (m, 4H), 7.67-7.86 (m, 3H), 7.93 (s, 1H), 8.86 (br. s., 1H), 9.71 (br. s., 1H), 10.13 (br. s., 1H); LC-MS (Condition A), MS m/z (M⁺+H) 640.0.

Example 1030

Preparation of Compound 1030

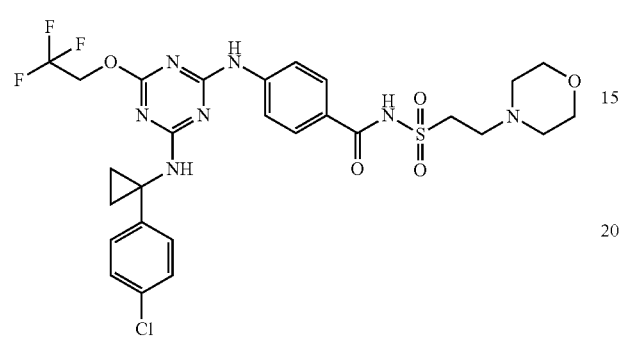

Compound 1030

Compound 1030 was prepared by the same method as Compound 1029 with the following modifications: 1-iodo-2-(2-iodoethoxy)ethane instead of 1,4-dibromobutane in Step 3 was used as a starting material to give compound 1030 (4 mg) as the TFA salt. 1H NMR (400 MHz, DMSO-d₆) δ ppm 1.17-1.48 (m, 4H), 1.80-2.12 (m, 4H), 3.37-4.41 (m, 8H), 5.00 (q, J=9.0 Hz, 2H), 7.15-7.44 (m, 4H), 7.67-7.86 (m, 3H), 7.93 (s, 1H), 8.86 (br. s., 1H), 9.71 (br. s., 1H), 10.13 (br. s., 1H); LC-MS (Condition A), MS m/z (M⁺+H) 656.0.

Example 1031

Preparation of Compound 1031

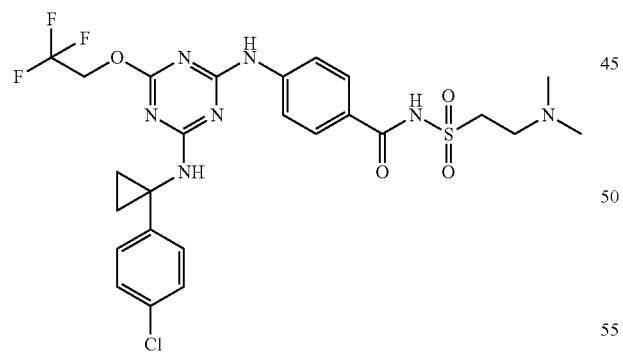

Compound 1031

Compound 1031 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), formaldehyde (9.15 μl, 0.123 mmol), Et₃N (21.41 μl, 0.154 mmol), were dissolved in DCM (Volume: 2 mL) and NaH(AcO)₃ (26.0 mg, 0.123 mmol) was added to the solution. The reaction was stirred for 4 h. The solvent was removed under vacuum and the crude product was purified by rev. phase preparative HPLC (Column: Sunfire prep C18 OBO 5 uM, 30×100 mm by Waters Corp) using a gradient of 20-100% ACN/water w/0.1% TFA modifier to give Compound 1031 (15 mg) as the TFA salt. 1H NMR (400 MHz, DMSO-d₆) δ ppm 1.17-1.48 (m, 4H), 1.80-2.12 (m, 4H), 3.37-4.41 (m, 8H), 5.00 (q, J=9.0 Hz, 2H), 7.15-7.44 (m, 4H), 7.67-7.86 (m, 3H), 7.93 (s, 1H), 8.86 (br. s., 1H), 9.71 (br. s., 1H), 10.13 (br. s., 1H); LC-MS (Condition A), MS m/z (M⁺+H) 614.0.

Example 1032

Preparation of Compound 1032

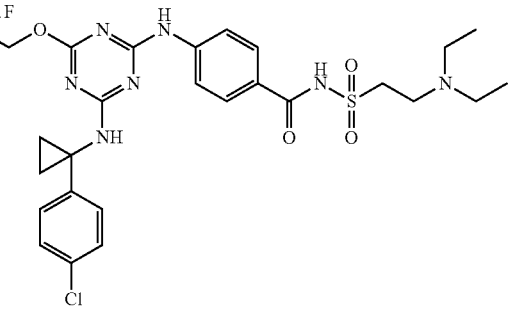

Compound 1032

Compound 1032 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), acetaldehyde (6.77 mg, 0.154 mmol), AcOH (1.758 μl, 0.031 mmol), were dissolved in DCM (Volume: 2 mL) and SODIUM TRIACETOXYBOROHYDRIDE (32.6 mg, 0.154 mmol) was added to the solution. The reaction was stirred for 4 h. The solvent was removed under vacuum and the crude product was purified by rev. phase HPLC (Column: Sunfire prep C18 OBO 5 uM, 30×100 mm by Waters Corp) using a gradient of 20-100% ACN/water w/0.1% TFA modifier to give compound 1032 (23 mg) as the TFA salt. 1H NMR (400 MHz, DMSO-d₆) δ ppm 1.19 (t, J=7.3 Hz, 6H), 1.27-1.42 (m, 4H), 3.14-3.29 (m, 4H), 3.45-3.58 (m, 2H), 3.97-4.10 (m, 2H), 5.00 (q, J=9.0 Hz, 2H), 7.16-7.40 (m, 4H), 7.69-7.85 (m, 3H), 7.93 (s, 1H), 8.85 (br. s., 1H), 9.46 (br. s., 1H), 10.13 (br. s., 1H); LC-MS (Condition A), MS m/z (M⁺+H) 642.0.

Example 1033

Preparation of Compound 1033

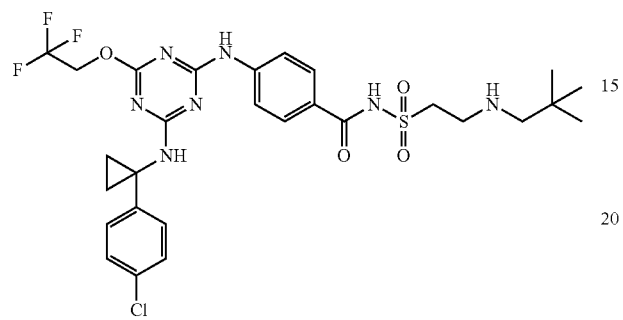

Compound 1033

Compound 1033 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), pivalaldehyde (2.78 mg, 0.032 mmol), AcOH (1.758 μl, 0.031 mmol) were dissolved in DCM (Volume: 2 mL) and stirred for 2 h followed by the addition of SODIUM TRIACETOXYBOROHYDRIDE (13.02 mg, 0.061 mmol). The reaction was stirred for 4 h. The solvent was removed under vacuum and the crude product was purified by rev. phase HPLC (Column: Sunfire prep C18 OBO 5 uM, 30×100 mm by Waters Corp) using a gradient of 20-100% ACN/water w/0.1% TFA modifier to give compound 1033 (6 mg) as the TFA salt. 1H NMR (400 MHz, DMSO-d₆) δ ppm 0.99 (s, 9H), 1.28-1.43 (m, 4H), 2.89 (t, J=6.1 Hz, 2H), 3.31-3.43 (m, 2H), 3.85-4.02 (m, 2H), 5.00 (q, J=8.8 Hz, 2H), 7.18-7.39 (m, 4H), 7.67-7.84 (m, 3H), 7.93 (s, 1H), 8.21 (br. s., 2H), 8.85 (br. s., 1H), 10.10 (br. s., 1H); LC-MS (Condition A), MS m/z (M⁺+H) 656.0.

Example 1034

Preparation of Compound 1034

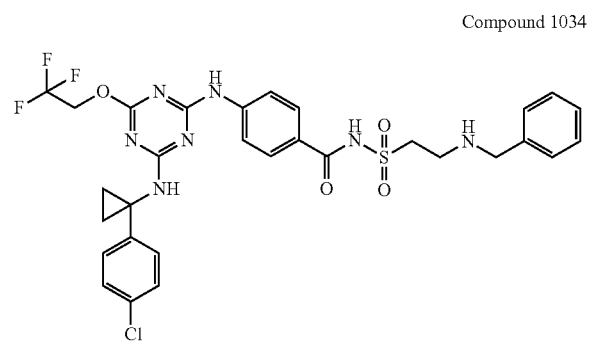 [SMILES: O=C(NS(=O)(=O)CCNCc1ccccc1)c1ccc(Nc2nc(NC3(c4ccc(Cl)cc4)CC3)nc(OCC(F)(F)F)n2)cc1]

Compound 1034

Compound 11034 was prepared by the same method as Compound 1029 with the following modifications: benzaldehyde instead of pivalaldehyde in Step 3 was used as a starting material to give compound 1034 (7 mg) as the TFA salt. 1H NMR (400 MHz, DMSO-d₆) δ ppm 1.20-1.45 (m, 4H), 3.32-3.46 (m, 2H), 3.85-4.01 (m, 2H), 4.26 (br. s., 2H), 5.00 (q, J=9.0 Hz, 2H), 7.20-7.30 (m, 2H), 7.31-7.39 (m, 2H), 7.41-7.57 (m, 5H), 7.67-7.85 (m, 3H), 7.88-8.00 (m, 1H), 8.85 (br. s., 1H), 8.99 (br. s., 2H), 10.13 (br. s., 1H); LC-MS (Condition A), MS m/z (M⁺+H) 676.0.

Example 1035

Preparation of Compound 1035

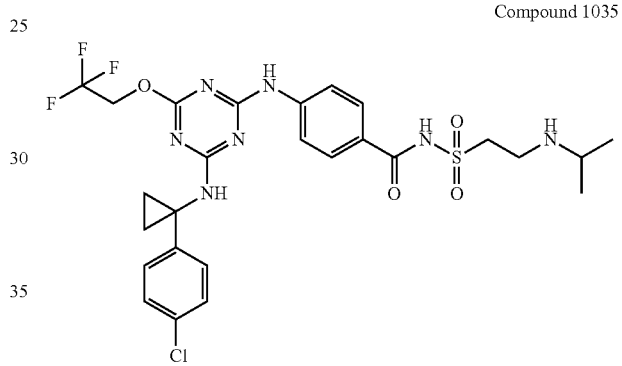

Compound 1035

Compound 1035 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol) was dissolved in DCM. To this solution was added propan-2-one (2.141 mg, 0.037 mmol) and TITANIUM(IV) ISOPROPDXIDE (18.00 μl, 0.061 mmol). The reaction was stirred for 16 h, then SODIUM TRIACETOXYBOROHYDRIDE (13.02 mg, 0.061 mmol) was added and the reaction was stirred for an additional 4 h. The reaction was quenched with a 1M solution of NaHSO₄ and extracted with DCM. The organic layer was collected, dried over sodium sulfate, and concentrated under vacuum. The crude product was purified by rev. phase preparative HPLC (Column: Sunfire prep C18 OBO 5 uM, 30×100 mm by Waters Corp) using a gradient of 20-100% ACN/water w/0.1% TFA modifier to give Compound 1035 (5 mg) as the TFA salt. 1H NMR (400 MHz, DMSO-d₆) δ ppm 1.23 (d, J=6.5 Hz, 6H), 1.28-1.43 (m, 4H), 3.28-3.46 (m, 3H), 3.81-3.93 (m, 2H), 5.00 (q, J=9.0 Hz, 2H), 7.19-7.30 (m, 2H), 7.30-7.39 (m, 2H), 7.66-7.85 (m, 3H), 7.88-7.97 (m, 1H), 8.53 (br. s., 2H), 8.85 (br. s., 1H), 10.12 (br. s., 1H); LC-MS (Condition A), MS m/z (M⁺+H) 614.0.

Example 1036

Preparation of Compound 1036

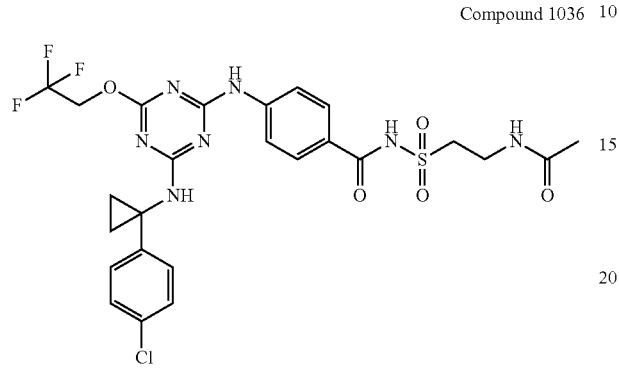

Compound 1036

Compound 1036 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), and Hunig's Base (0.027 mL, 0.154 mmol) were dissolved in DCM (Volume: 2 mL). Acetyl chloride (2.65 mg, 0.034 mmol) was added to the reaction mixture and was stirred for 2 h. LC/MS showed the reaction to be complete. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier to give Compound 1036 (10 mg). 1H NMR (400 MHz, DMSO-$d_6$) δ ppm 1.26-1.44 (m, 4H), 1.73 (s, 3H), 3.46 (q, J=6.4 Hz, 2H), 3.65 (t, J=6.9 Hz, 2H), 5.00 (q, J=9.0 Hz, 2H), 7.17-7.40 (m, 4H), 7.67-7.83 (m, 3H), 7.87-7.97 (m, 1H), 8.05 (t, J=5.1 Hz, 1H), 8.85 (br. s., 1H), 10.11 (br. s., 1H), 11.83 (br. s., 1H); LC-MS (Condition A), MS m/z (M⁺+H) 628.0.

Example 1037

Preparation of Compounds 1037

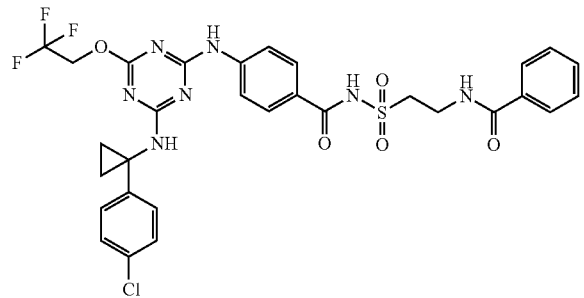

Compound 1037

Compound 1037 was prepared by the same method as Compound 1029 with the following modifications: benzoyl chloride instead of acetyl chloride in Step 3 was used as a starting material to give compound 1037 (10 mg). 1H NMR (400 MHz, DMSO-$d_6$) δ ppm 1.24-1.49 (m, 4H), 3.65-3.74 (m, 2H), 3.76-3.83 (m, 2H), 5.00 (q, J=9.0 Hz, 2H), 7.19-7.56 (m, 7H), 7.65-7.97 (m, 6H), 8.62-8.71 (m, 1H), 8.84 (br. s., 1H), 10.10 (br. s., 1H), 11.89 (br. s., 1H); LC-MS (Condition A), MS m/z (M⁺+H) 690.0.

Example 1038

Preparation of Compound 1038

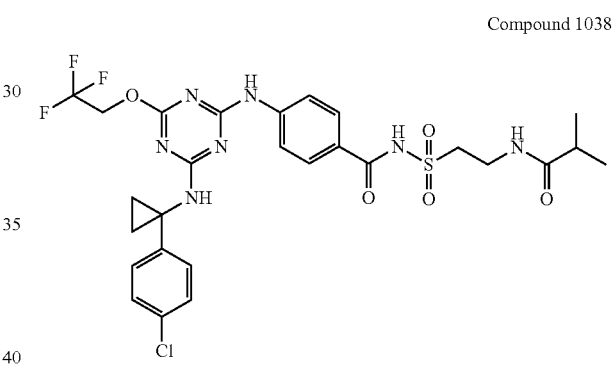

Compound 1038

Compound 1038 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (25 mg, 0.043 mmol), isobutyric acid (5.64 mg, 0.064 mmol), PyBOP (33.3 mg, 0.064 mmol), and Hunig's Base (0.037 mL, 0.213 mmol) were stirred in DCM (Volume: 2 mL) for 16 h. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier to give compound 1038 (18 mg). 1H NMR (400 MHz, MeOD) δ ppm 1.08 (d, 6H), 1.34-1.45 (m, 4H), 2.38 (quin, J=6.9 Hz, 1H), 3.63-3.71 (m, 2H), 3.71-3.78

(m, 2H), 4.90-4.94 (m, 2H), 7.23-7.36 (m, 4H), 7.67-7.82 (m, 3H), 7.88-7.99 (m, 1H), LC-MS (Condition A), MS m/z (M⁺+H) 656.0.

Example 1039

Preparation of Compound 1039

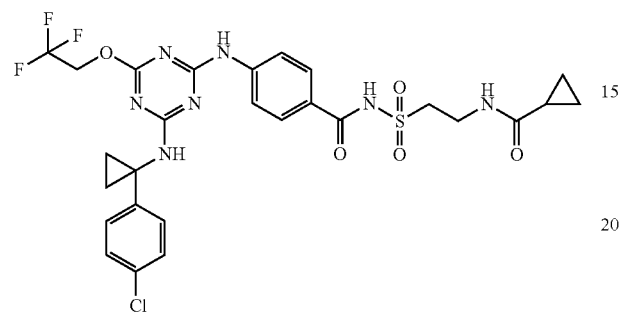

Compound 1039

Compound 1039 was prepared by the same method as Compound 1038 with the following modifications: cyclopropane carboxylic acid instead of isobutyric acid in Step 3 was used as a starting material to give Compound 1110 (17 mg). 1H NMR (400 MHz, MeOD) δ ppm 0.61-0.72 (m, 2H), 0.75-0.83 (m, 2H), 1.34-1.51 (m, 5H), 3.65-3.72 (m, 2H), 3.72-3.78 (m, 2H), 4.87-4.95 (m, 2H), 7.23-7.35 (m, 4H), 7.66-7.81 (m, 3H), 7.88-7.98 (m, 1H); LC-MS (Condition A), MS m/z (M⁺+H) 654.0.

Example 1040

Preparation of Compound 1040

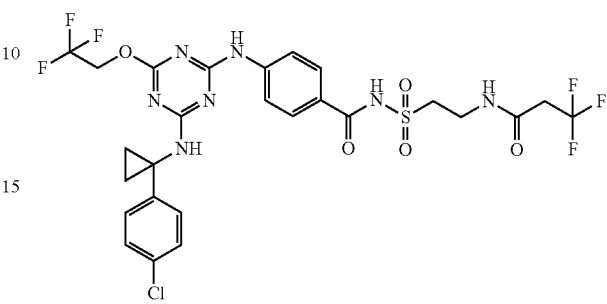

Compound 1040

Compound 1040 was prepared by the same method as Compound 1038 with the following modifications: 3,3,3-trifluoropropanoic acid instead of isobutyric acid in Step 3 was used as a starting material to give compound 1040 (17 mg). 1H NMR (400 MHz, MeOD) δ ppm 7.87-7.99 (m, 1H), 7.67-7.81 (m, 3H), 7.23-7.34 (m, 4H), 4.86-4.94 (m, 2H), 3.67-3.81 (m, 4H), 3.15 (q, J=10.8 Hz, 2H), 1.33-1.47 (m, 4H); LC-MS (Condition A), MS m/z (M⁺+H) 696.0.

Example 1041

Preparation of Compound 1041

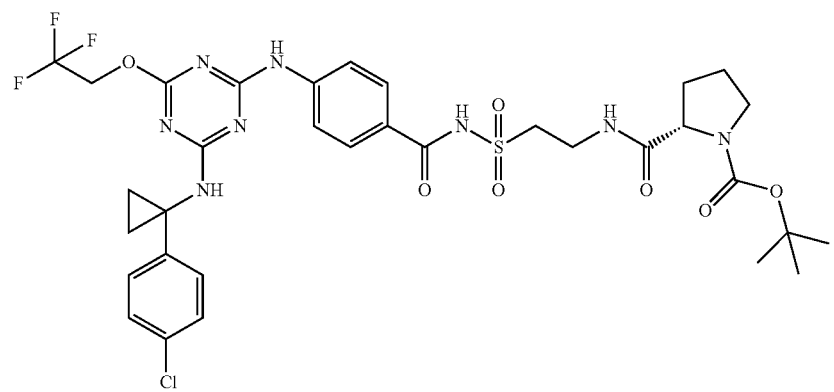

Compound 1041

Compound 1041 was prepared by the same method as compound 1038 with the following modifications: (S)-1-(tert-butoxycarbonyl)pyrrolidine-2-carboxylic acid instead of isobutyric acid in Step 3 was used as a starting material. After HPLC, the product fractions were diluted with EtOAc and washed with water 2×, followed by brine. The organic layer was collected, dried over sodium sulfate, and concentrated under vacuum to give compound 1041 (18 mg). 1H NMR (400 MHz, MeOD) δ ppm 7.91 (s, 1H), 7.63-7.80 (m, 3H), 7.19-7.34 (m, 4H), 4.84-4.92 (m, 2H), 4.10 (dd, J=8.7, 3.9 Hz, 1H), 3.62-3.80 (m, 4H), 3.39-3.53 (m, 2H), 1.77-2.24 (m, 4H), 1.26-1.53 (m, 13H); LC-MS (Condition A), MS m/z (M⁺+H) 783.0.

Example 1042

Preparation of Compound 1042

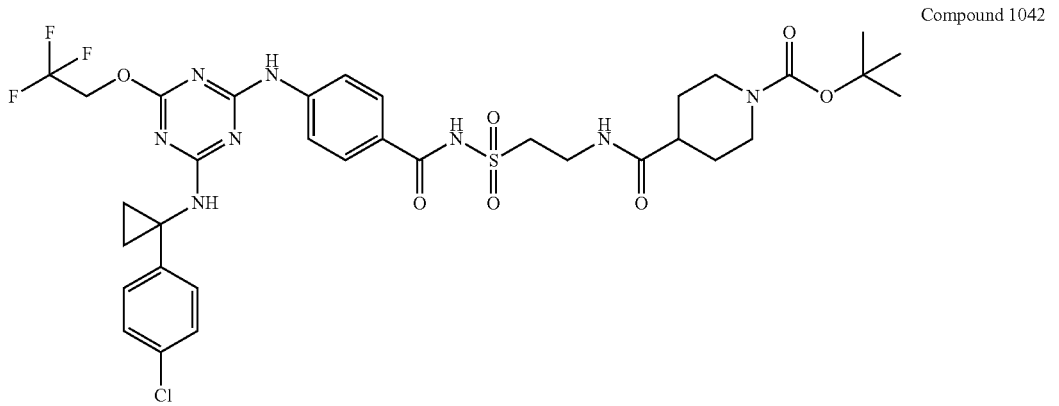 [SMILES: CC(C)(C)OC(=O)N1CCC(C(=O)NCCS(=O)(=O)NC(=O)c2ccc(Nc3nc(NC4(c5ccc(Cl)cc5)CC4)nc(OCC(F)(F)F)n3)cc2)CC1]

Compound 1042 was prepared by the same method as compound 1038 with the following modifications: 1-(tert-butoxycarbonyl)piperidine-4-carboxylic acid instead of isobutyric acid in Step 3 was used as a starting material. After HPLC, the product fractions were diluted with EtOAc and washed with water 2×, followed by brine. The organic layer was collected, dried over sodium sulfate, and concentrated under vacuum to give compound 1042 (18 mg). 1H NMR (400 MHz, MeOD) δ ppm 7.90-7.99 (m, 1H), 7.63-7.85 (m, 3H), 7.22-7.37 (m, 4H), 4.86-4.95 (m, 2H), 3.94-4.12 (m, 2H), 3.61-3.76 (m, 4H), 2.58-2.78 (m, 2H), 2.14-2.33 (m, 1H), 1.56-1.70 (m, 2H), 1.24-1.55 (m, 15H); LC-MS (Condition A), MS m/z (M$^+$+H) 797.0.

Example 1043

Preparation of Compound 1043

Compound 1043 was prepared by the same method as Compound 1038 with the following modifications: nicotinic acid instead of isobutyric acid in Step 3 was used as a starting material to give compound 1043 (18 mg). 1H NMR (400 MHz, MeOD) δ ppm 9.01-9.05 (m, 1H), 8.76-8.81 (m, 1H), 8.46-8.54 (m, 1H), 7.63-7.90 (m, 5H), 7.23-7.37 (m, 4H), 4.88-4.94 (m, 2H), 3.88-3.99 (m, 4H), 1.35-1.46 (m, 4H); LC-MS (Condition A), MS m/z (M$^+$+H) 691.0.

Example 1044

Preparation of Compounds 1044

Compound 1044 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), and Hunig's Base (0.027 mL, 0.154 mmol) were dissolved in DCM (Volume: 2 mL). Methyl chloroformate (5.81 mg, 0.061 mmol) was added to the reaction mixture and was stirred for 10 min then quenched with 2 drops of water. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier to give compound 1044 (19 mg). 1H NMR (400 MHz, MeOD) δ ppm 7.87-7.98 (m, 1H), 7.67-7.81 (m, 3H), 7.23-7.37 (m, 4H), 4.87-4.94 (m, 2H), 3.70-3.78 (m, 2H), 3.58-3.64 (m, 2H), 3.54 (s, 3H), 1.35-1.46 (m, 4H); LC-MS (Condition A), MS m/z (M⁺+H) 644.0.

Example 1045

Preparation of Compound 1045

Compound 1045

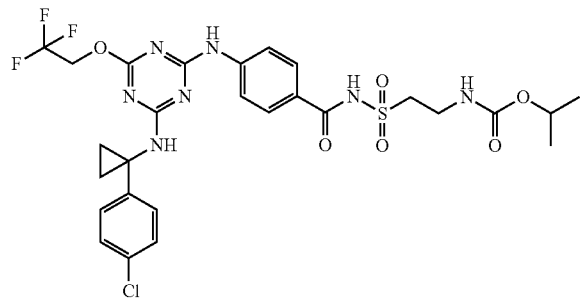

Compound 1045 was prepared by the same method as Compound 1044 with the following modifications: isoproply chloroformate instead of methyl chloroformate in Step 3 was used as a starting material to give Compound 1045 (18 mg). 1H NMR (400 MHz, MeOD) δ ppm 7.86-8.00 (m, 1H), 7.67-7.80 (m, 3H), 7.22-7.36 (m, 4H), 4.86-4.94 (m, 2H), 4.72-4.83 (m, 1H), 3.73 (t, J=6.1 Hz, 2H), 3.59 (t, J=6.3 Hz, 2H), 1.34-1.45 (m, 4H), 1.13 (d, J=6.3 Hz, 6H), LC-MS (Condition A), MS m/z (M⁺+H) 672.0.

Example 1046

Preparation of Compound 1046

Compound 1046 was prepared by the same method as Compound 1044 with the following modifications: neopentyl chloroformate instead of methyl chloroformate in Step 3 was used as a starting material to give Compound 1046 (13 mg). 1H NMR (400 MHz, MeOD) δ ppm 7.87-7.99 (m, 1H), 7.66-7.81 (m, 3H), 7.23-7.38 (m, 4H), 4.86-4.94 (m, 2H), 3.71-3.77 (m, 2H), 3.58-3.67 (m, 4H), 1.33-1.46 (m, 4H), 0.86 (s, 9H); LC-MS (Condition A), MS m/z (M⁺+H) 700.0.

Example 1047

Preparation of Compound 1047

Compound 1047

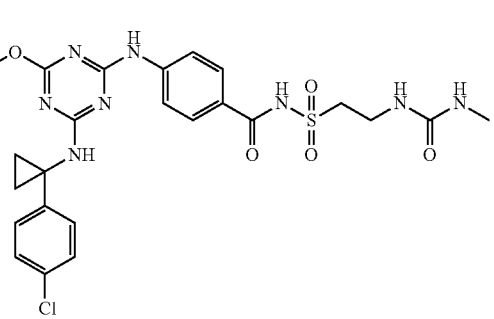

Compound 1047 was prepared by modification of Step 3 of the method to prepare compound 1029. N-(2-aminoethylsulfonyl)-4-(4-(1-(4-chlorophenyl)cyclopropylamino)-6-(2,2,2-trifluoroethoxy)-1,3,5-triazin-2-ylamino)benzamide HCl salt (20 mg, 0.031 mmol), and Hunig's Base (0.027 mL, 0.154 mmol) were dissolved in DCM (Volume: 2 mL). Methyl isocyanate (3.50 mg, 0.061 mmol) was added to the reaction mixture and was stirred for 10 min then quenched with 2 drops of water. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier to give compound 1047 (19 mg). 1H NMR (400 MHz, MeOD) δ ppm 1.34-1.45 (m, 4H), 2.63 (s, 3H), 3.60-3.68 (m, 2H), 3.68-3.75 (m, 2H), 4.87-4.94 (m, Compound 1046

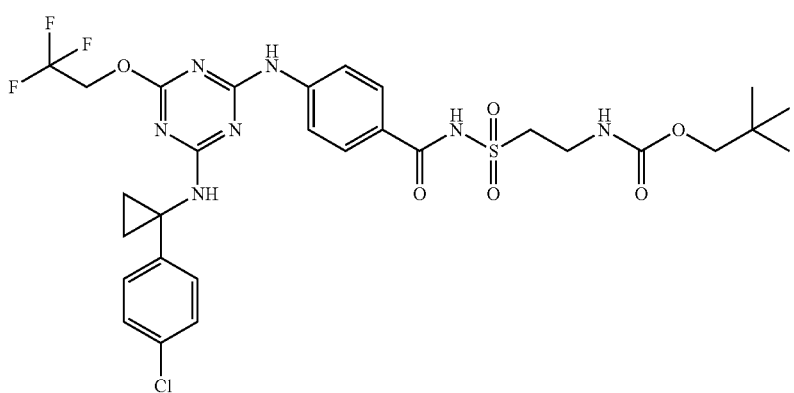

2H), 7.22-7.36 (m, 4H), 7.65-7.81 (m, 3H), 7.86-7.98 (m, 1H); LC-MS (Condition A), MS m/z (M⁺+H) 643.0.

Example 1048

Preparation of Compound 1048

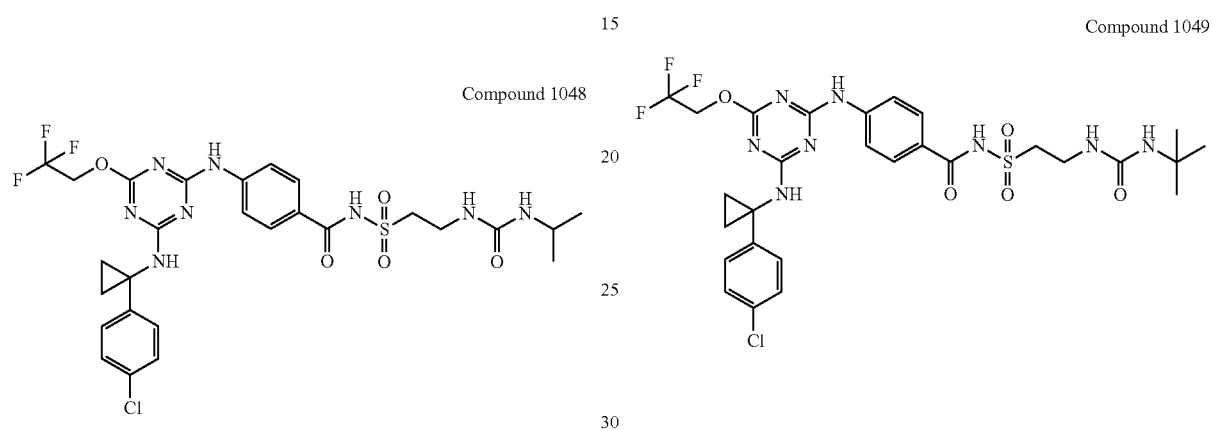

Compound 1048

Compound 1048 was prepared by the same method as Compound 1047 with the following modifications: isopropyl isocyanate instead of methyl isocyanate in Step 3 was used as a starting material to give Compound 1119 (16 mg). 1H NMR (400 MHz, MeOD) δ ppm 1.06 (d, 6H), 1.33-1.45 (m, 4H), 3.59-3.78 (m, 4H), 4.73-4.83 (m, 1H), 4.86-4.96 (m, 2H), 7.20-7.36 (m, 4H), 7.66-7.81 (m, 3H), 7.87-7.98 (m, 1H); LC-MS (Condition A), MS m/z (M⁺+H) 671.0.

Example 1049

Preparation of Compound 1049

Compound 1049

Compound 1049 was prepared by the same method as Compound 1047 with the following modifications: tert-butyl isocyanate instead of methyl isocyanate in Step 3 was used as a starting material to give Compound 1049 (15 mg). 1H NMR (400 MHz, MeOD) δ ppm 1.26 (s, 9H), 1.34-1.45 (m, 4H), 3.59 (t, J=5.6 Hz, 2H), 3.69 (t, J=5.8 Hz, 2H), 4.86-4.93 (m, 2H), 7.22-7.35 (m, 4H), 7.67-7.81 (m, 3H), 7.88-7.99 (m, 1H); LC-MS (Condition A), MS m/z (M⁺+H) 685.0. 050121.

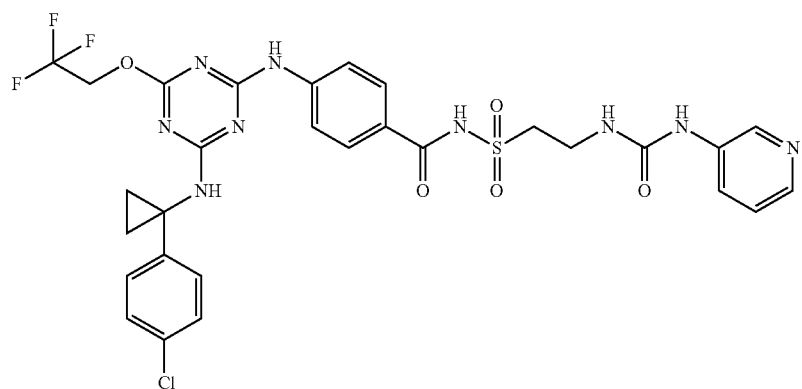

Compound 1050

Compound 1050 was prepared by the same method as Compound 1047 with the following modifications: pyridine-3-isocyanate instead of methyl isocyanate in Step 3 was used as a starting material to give compound 1050 (15 mg). 1H NMR (400 MHz, MeOD) δ ppm 1.34-1.46 (m, 4H), 3.75-3.88 (m, 4H), 4.87-4.93 (m, 2H), 7.23-7.35 (m, 4H), 7.61-7.80 (m, 3H), 7.81-7.91 (m, 2H), 8.16 (ddd, J=8.6, 2.4, 1.3 Hz, 1H), 8.35 (d, J=5.5 Hz, 1H), 9.18 (d, J=2.3 Hz, 1H); LC-MS (Condition A), MS m/z (M$^+$+H) 706.0.

Examples 2001 and 2002

Preparation of Compounds 2001 and 2002

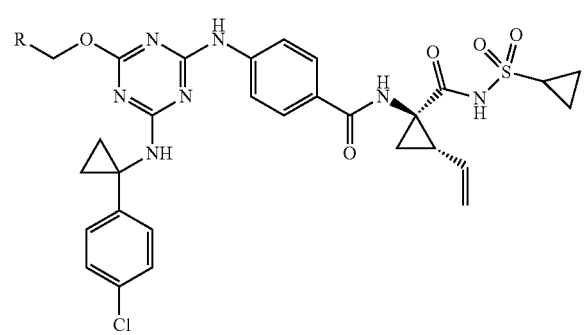

R = H Compound 2001  R = CF$_3$ Compound 2002

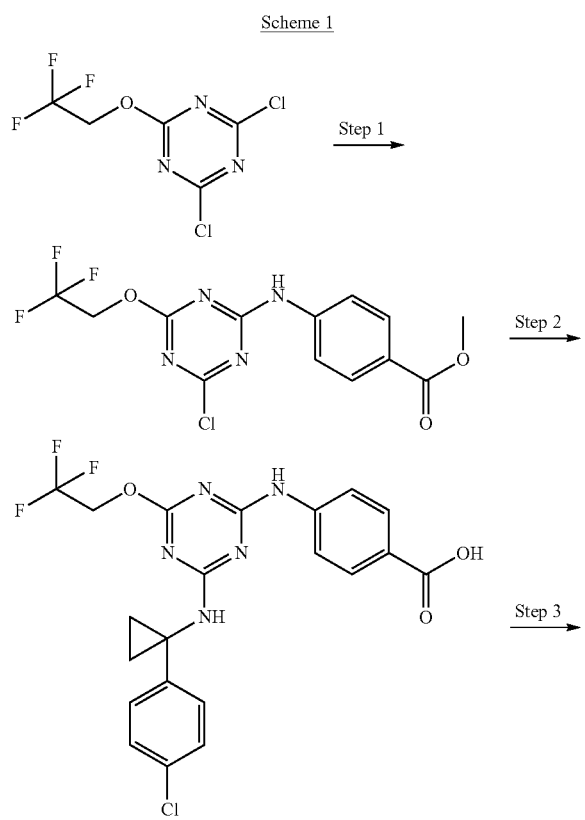

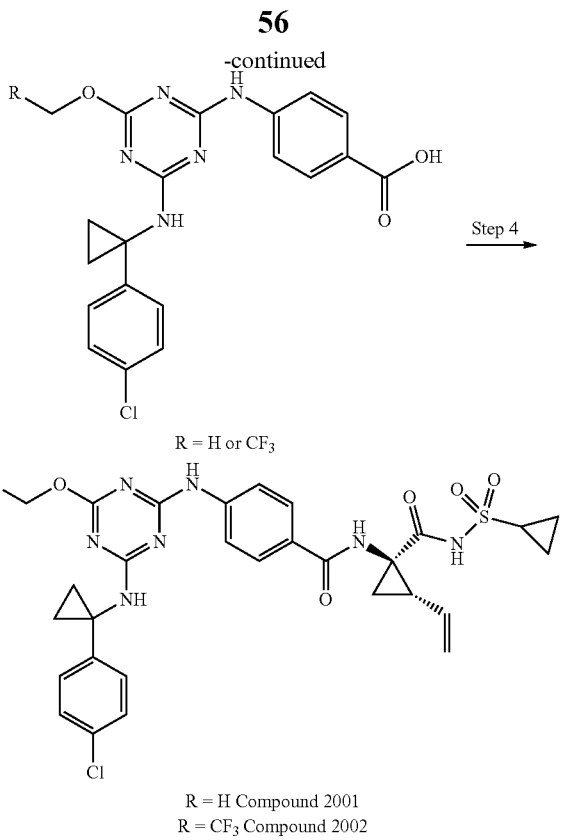

Step 1:
To a solution of 2,4-dichloro-6-(2,2,2-trifluoroethoxy)-1,3,5-triazine (2.009 g, 8.1 mmol) in THF (10 mL) was added methyl 4-aminobenzoate (1.224 g, 8.10 mmol) and Hunig's Base (1.415 mL, 8.10 mmol). The resulting mixture was stirred for 16 h. The precipitate was filtrated through a plug washing with THF to give 1.5 g of the desired product.

Step 2:
To a solution of methyl 4-(4-chloro-6-(2,2,2-trifluoroethoxy)-1,3,5-triazin-2-ylamino)benzoate (870 mg, 2.4 mmol) from Step 1 in THF (10 mL) was added 1-(4-chlorophenyl)cyclopropanamine, HCl (500 mg, 2.450 mmol) and Hunig's Base (1.677 mL, 9.60 mmol). The resulting mixture was stirred for 16 h. The precipitate was filtrated through a plug washing with THF to give a crude product that was purified by Biotage eluting with 4/1-hexane/ethyl acetate to give 1.1 g of the desired product as a solid.

Step 3:
To a solution of methyl 4-(4-(1-(4-chlorophenyl)cyclopropylamino)-6-(2,2,2-trifluoroethoxy)-1,3,5-triazin-2-ylamino)benzoate (1.1 g, 2.227 mmol) from Step 2 in MeOH (10 mL), THF (10.00 mL) and Water (5.00 mL) was added MeOH (10 mL). The resulting solution was reflux for 0.5 h. After concentration, the residue was acidified by 1 N HCl and solid was collected with a plug washing with water to give a white solid (1 g) as a mixture that was used in the next step as it is.

Step 4:
To a solution of the products from Step 3 above (33 mg), (1R,2S)-1-amino-N-(cyclopropylsulfonyl)-2-vinylcyclopropanecarboxamide, HCl (22.01 mg, 0.083 mmol), and N-ethyl-N-isopropylpropan-2-amine (0.060 mL, 0.344 mmol) in CH$_2$Cl$_2$ (2 mL) was added HATU (39.2 mg, 0.103 mmol). The resulting solution was stirred for 2 h. After concentration, the residue was purified by prep HPLC to give 22 mg of the first fraction Compound 2001 and 16 mg of the second fraction Compound 2002.

Data of compound 2001: LC-MS (Condition B), MS m/z 565.1 (M$^+$+H) 624.08.

Data of compound 2002: LC-MS (Condition B), MS m/z 565.1 (M$^+$+H) 692.07.

Examples 2003 and 2004

Preparation of Compounds 2003 and 2004

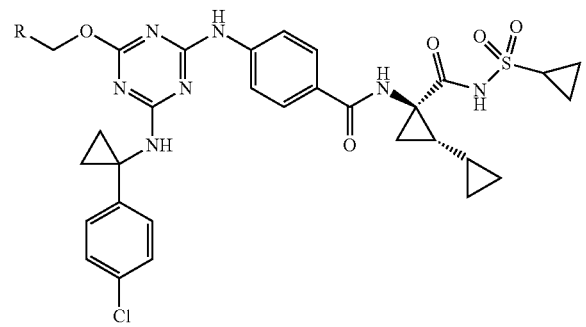

R = H Compound 2003  R = CF$_3$ Compound 2004

Compounds 2003 and 2004 were prepared by the same method as Compounds 2001 and 2002 with the following modifications: (1S,2R)-2-Amino-N-(cyclopropylsulfonyl)bi(cyclopropane)-2-carboxamide, HCl instead of (1R,2S)-1-amino-N-(cyclopropylsulfonyl)-2-vinylcyclopropanecarboxamide, HCl was used as a starting material in Step 4 to give Compounds 2003 (22 mg) and 2004 (16 mg).

Data of compound 2003: LC-MS (Condition B), MS m/z 565.1 (M$^+$+H) 638.09.

Data of compound 2004: LC-MS (Condition B), MS m/z 565.1 (M$^+$+H) 706.10.

Examples 2005 and 2006

Preparation of Compounds 2005 and 2006

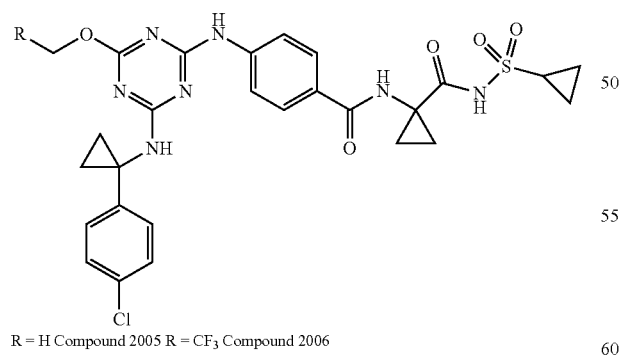

R = H Compound 2005  R = CF$_3$ Compound 2006

Compounds 2003 and 2004 were prepared by the same method as Compounds 2001 and 2002 with the following modifications: 1-Amino-N-(cyclopropylsulfonyl)cyclopropanecarboxamide, HCl instead of (1R,2S)-1-amino-N-(cyclopropylsulfonyl)-2-vinylcyclopropanecarboxamide, HCl was used as a starting material in Step 4 to give Compounds 2005 (40 mg) and 2006 (16 mg).

Data of compound 2005: LC-MS (Condition B), MS m/z 565.1 (M$^+$+H) 598.04.

Data of compound 2006: LC-MS (Condition B), MS m/z 565.1 (M$^+$+H) 666.01.

Examples 2007 and 2008

Preparation of Compounds 2007 and 2008

R = H Compound 2007  R = CF$_3$ Compound 2008

Compounds 2007 and 2008 were prepared by the same method as Compounds 2001 and 2002 with the following modifications: (1R,2R)-1-Amino-2-(difluoromethyl)-N-(1-methylcyclopropylsulfonyl)cyclopropanecarboxamide, HCl instead of (1R,2S)-1-amino-N-(cyclopropylsulfonyl)-2-vinylcyclopropanecarboxamide, HCl was used as a starting material in Step 4 to give Compounds 2007 (22 mg) and 2008 (16 mg).

Data of compound 2007: LC-MS (Condition B), MS m/z 565.1 (M$^+$+H) 662.06.

Data of compound 2008: LC-MS (Condition B), MS m/z 565.1 (M$^+$+H) 730.04.

Example 2009

Preparation of Compound 2009

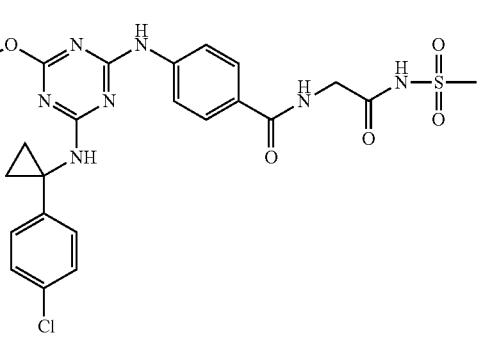

Compound 2009

Scheme 2

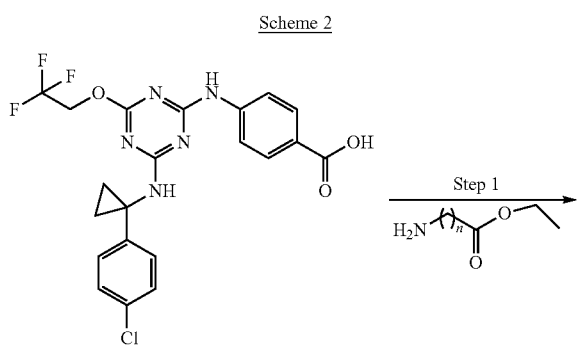

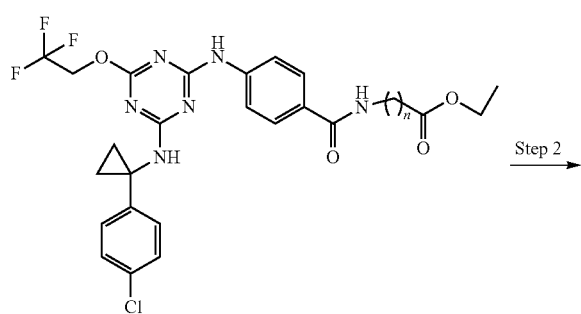

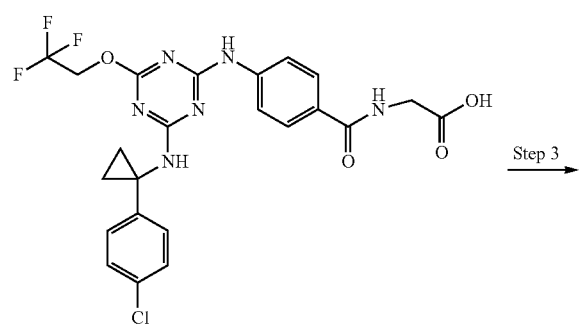

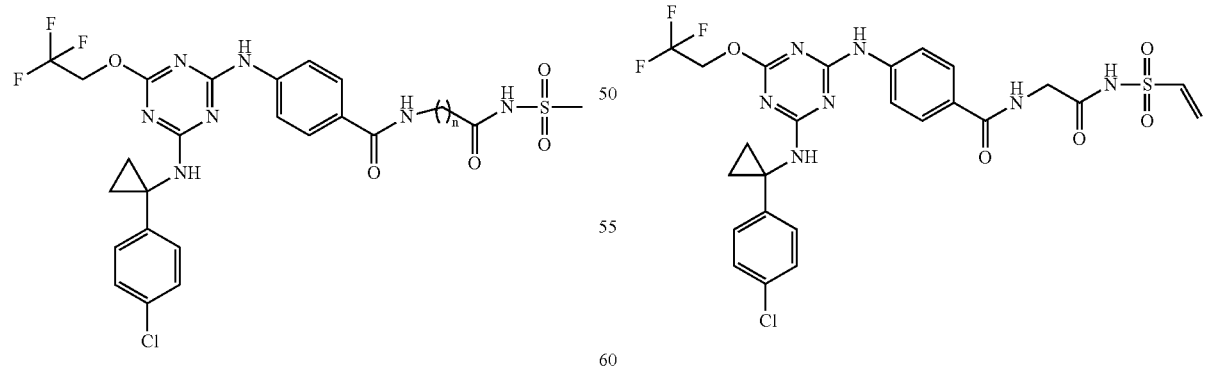

Step 1:

To a solution of 4-(4-(1-(4-chlorophenyl)cyclopropylamino)-6-(2,2,2-trifluoroethoxy)-1,3,5-triazin-2-ylamino) benzoic acid (200 mg, 0.42 mmol) in DCM (5 mL) solution were added ethyl 2-aminoacetate (65 mg, 0.63 mmol), HATU (238 mg, 0.63 mmol) and iPr$_2$NEt (0.22 mL, 1.25 mmol). The mixture was stirred at room temperature for 16 hs. The solvent was removed under vacuum. The residue was purified via silica gel column (EtOAC/Hexanes 20% to 40%) to give ethyl 2-(4-(4-(1-(4-chlorophenyl)cyclopropylamino)-6-(2,2,2-trifluoroethoxy)-1,3,5-triazin-2-ylamino)benzamido)acetate (240 mg, 100%) as white solid. LC-MS (Condition A), MS m/z 565.1 (M$^+$+H).

Step 2:

To a suspension of ethyl 2-(4-(4-(1-(4-chlorophenyl)cyclopropylamino)-6-(2,2,2-trifluoroethoxy)-1,3,5-triazin-2-ylamino)benzamido)acetate (240 mg, 0.43 mmol) in THF and water solution (6 mL, 1:1 ratio) was added NaOH (68 mg, 1.7 mmol). The mixture was heated to reflux for 2 hours. After cooling to room temperature, the reaction solution was acidified with 1N HCl. The product was extracted by EtOAc. The organic layer was washed with brine, dried over Na$_2$SO$_4$ and concentrated under vacuum. The crude product was used directly in the next step.

Step 3:

To a solution of intermediate from step 2 (20 mg, 0.037 mmol) in DMF (2 mL) were added EDCI (18 mg, 0.09 mmol), methanesulfonamide (9.0 mg, 0.09 mmol) and DMAP (11.4 mg, 0.09 mmol). The mixture was stirred at room temperature for 16 hs. The residue was purified by prep.HPLC to give Compound 2009 as white solid (2.6 mg, 11%). 1H NMR (400 MHz, MeOD) δ ppm 0.87 (m, 2H), 1.27 (s, 2H), 1.33 (m, 2H), 3.16 (s, 3H), 7.25 (m, 4H), 7.60-7.69 (m, 3H), 7.84 (m, 1H); LC-MS (Condition A), MS m/z 614.0 (M$^+$+H).

Example 2010

Preparation of Compound 2010

Compound 2010

The Compound 2010 was synthesized following the procedure reported in Scheme 2 of Example 2009. Ethenesulfonamide was used as starting material instead of methanesulfonamide. LC-MS (Condition A), MS m/z 626.0 (M⁺+H).

Example 2011

Preparation of Compound 2011

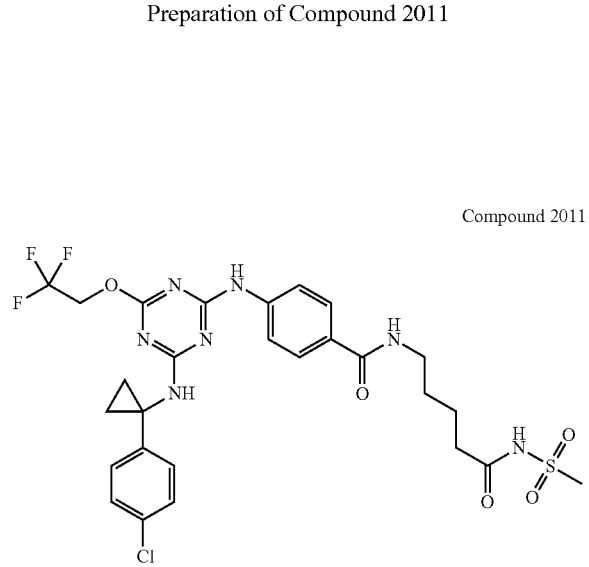

Compound 2011

The Compound 2011 was synthesized following the procedure reported in Scheme 2 of Example 2009. 5-Aminovalerate HCl and ethenesulfonamide were used as starting material instead of ethyl 2-aminoacetate and methanesulfonamide. LC-MS (Condition A), MS m/z 656.1 (M⁺+H).

Example 2012

Preparation of Compound 2012

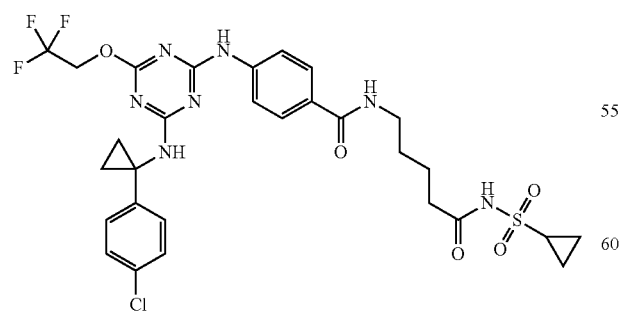

Compound 2012

The Compound 2012 was synthesized following the procedure reported in Scheme 2 of Example 2009. 5-Aminovalerate HCl and cyclopropanesulfonamide were used as starting material instead of ethyl 2-aminoacetate and methanesulfonamide. LC-MS (Condition A), MS m/z 682.0 (M⁺+H).

Example 2013

Preparation of Compound 2013

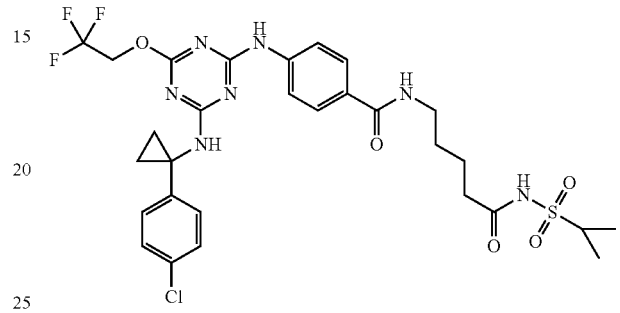

Compound 2013

The Compound 2013 was synthesized following the procedure reported in Scheme 2 of Example 2009. 5-Aminovalerate HCl and propane-2-sulfonamide were used as starting material instead of ethyl 2-aminoacetate and methanesulfonamide. LC-MS (Condition A), MS m/z 684.1 (M⁺+H).

Example 2014

Preparation of Compound 2014

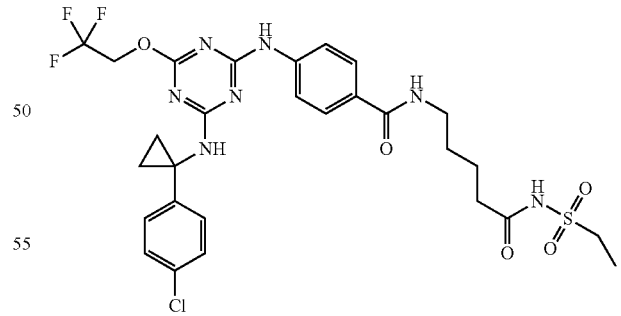

Compound 2014

The Compound 2014 was synthesized following the procedure reported in Scheme 2 of Example 2009. 5-Aminovalerate HCl and ethanesulfonamide were used as starting material instead of ethyl 2-aminoacetate and methanesulfonamide. LC-MS (Condition A), MS m/z 670.1 (M$^+$+H).

Example 2015

Preparation of Compound 2015

Compound 2015

The Compound 2015 was synthesized following the procedure reported in Scheme 2 of Example 2009. 5-Aminovalerate HCl and ethenesulfonamide were used as starting material instead of ethyl 2-aminoacetate and methanesulfonamide. LC-MS (Condition A), MS m/z 668.0 (M$^+$+H).

Example 2016

Preparation of Compound 2016

Compound 2016

The Compound 2016 was synthesized following the procedure reported in Scheme 2 of Example 2009. Ethyl 3-aminopropanoate and ethenesulfonamide were used as starting material instead of ethyl 2-aminoacetate and methanesulfonamide. LC-MS (Condition A), MS m/z 640.0 (M$^+$+H).

Example 2017

Preparation of Compound 2017

Compound 2017

The Compound 2017 was synthesized following the procedure reported in Scheme 2 of Example 2009. Ethyl 4-aminobutyrate and ethenesulfonamide were used as starting material instead of ethyl 2-aminoacetate and methanesulfonamide. LC-MS (Condition A), MS m/z 654.0 (M$^+$+H).

Example 2018

Preparation of Compound 2018

Compound 2018

The Compound 2018 was synthesized following the procedure reported in Scheme 2 of Example 2009. Ethyl 3-aminopropanoate was used as starting material instead of ethyl 2-aminoacetate. LC-MS (Condition A), MS m/z 628.0 (M⁺+H).

Example 2019

Preparation of Compound 2019

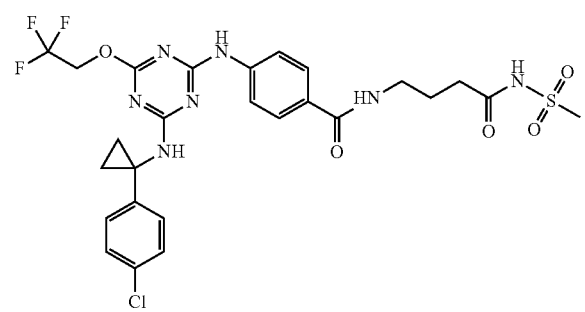

Compound 2019

The Compound 2019 was synthesized following the procedure reported in Scheme 2 of Example 2009. Ethyl 4-aminobutyrate were used as starting material instead of ethyl 2-aminoacetate. LC-MS (Condition A), MS m/z 642.0 (M⁺+H).

Example 2020

Preparation of Compound 2020

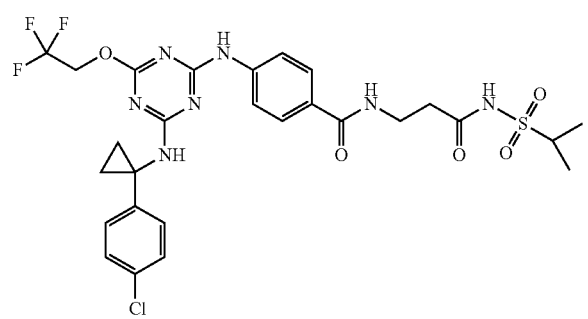

Compound 2020

The Compound 2020 was synthesized following the procedure reported in Scheme 2 of Example 2009. Ethyl 3-aminopropanoate and propane-2-sulfonamide were used as starting material instead of ethyl 2-aminoacetate and methanesulfonamide. LC-MS (Condition A), MS m/z 656.0 (M⁺+H).

Example 2021

Preparation of Compounds 2021

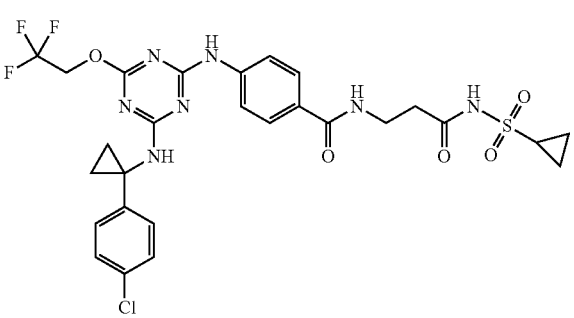

Compound 2021

The Compound 2021 was synthesized following the procedure reported in Scheme 2 of Example 2009. Ethyl 3-aminopropanoate and cyclopropanesulfonamide were used as starting material instead of ethyl 2-aminoacetate and methanesulfonamide. LC-MS (Condition A), MS m/z 654.0 (M⁺+H).

Example 2022

Preparation of Compounds 2022

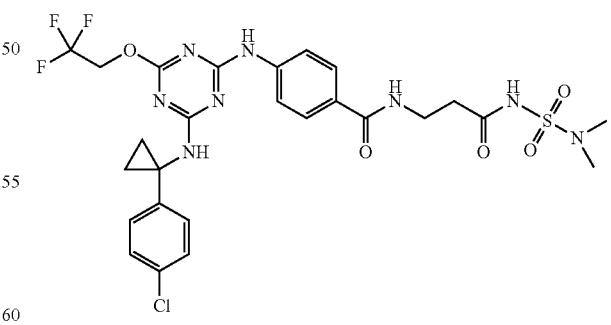

Compound 2022

The Compound 2022 was synthesized following the procedure reported in Scheme 2 of Example 2009. Ethyl 3-aminopropanoate and N,N-dimethylsulfamide were used as starting material instead of ethyl 2-aminoacetate and methanesulfonamide. LC-MS (Condition A), MS m/z 657.0 (M⁺+H).

Example 2023

Preparation of Compounds 2023

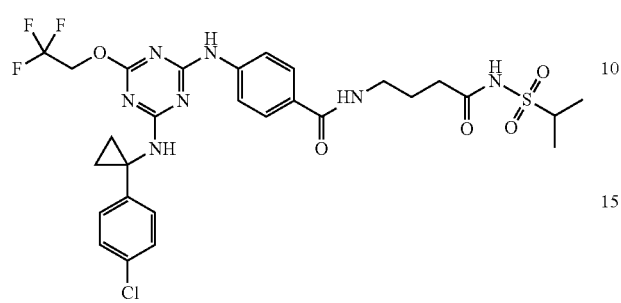

Compound 2023

The Compound 2023 was synthesized following the procedure reported in Scheme 2 of Example 2009. Ethyl 4-aminobutyrate and propane-2-sulfonamide were used as starting material instead of ethyl 2-aminoacetate and methanesulfonamide. LC-MS (Condition A), MS m/z 670.0 (M$^+$+H).

Example 2024

Preparation of Compound 2024

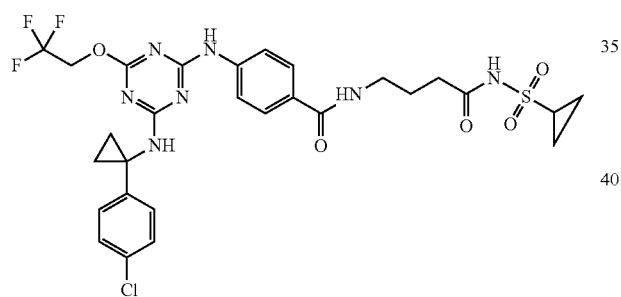

Compound 2024

The Compound 2024 was synthesized following the procedure reported in Scheme 2 of Example 2009. Ethyl 4-aminobutyrate and cyclopropanesulfonamide were used as starting material instead of ethyl 2-aminoacetate and methanesulfonamide. LC-MS (Condition A), MS m/z 668.0 (M$^+$+H).

Example 2025

Preparation of Compound 2025

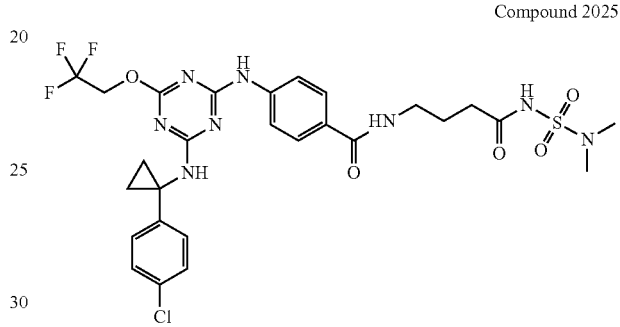

Compound 2025

The Compound 2025 was synthesized following the procedure reported in Scheme 2 of Example 2009. Ethyl 4-aminobutyrate and N,N-dimethylsulfamide were used as starting material instead of ethyl 2-aminoacetate and methanesulfonamide. LC-MS (Condition A), MS m/z 671.0 (M$^+$+H).

Example 026

Preparation of Compound 2026

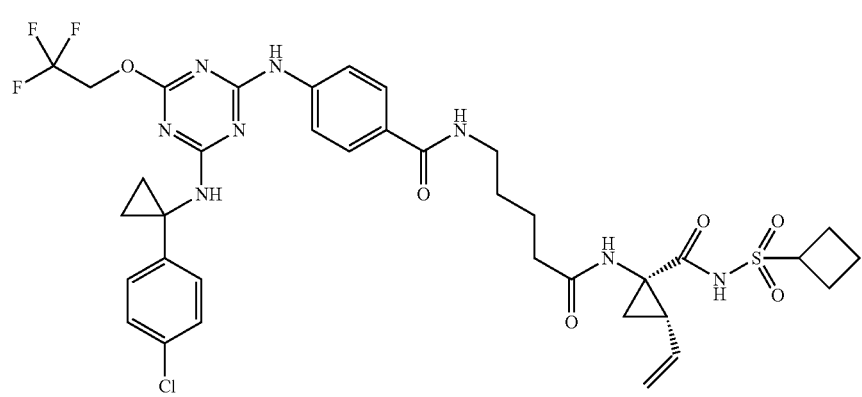

Compound 2026

The Compound 2026 was synthesized following the procedure reported in Scheme 2 of Example 2009. 5-Aminovalerate HCl and (1R,2S)-1-amino-N-(cyclobutylsulfonyl)-2-vinylcyclopropanecarboxamide, HCl were used as starting material instead of ethyl 2-aminoacetate and methanesulfonamide. LC-MS (Condition A), MS m/z 805.0 (M⁺+H).

Example 2027

Preparation of Compound 2027

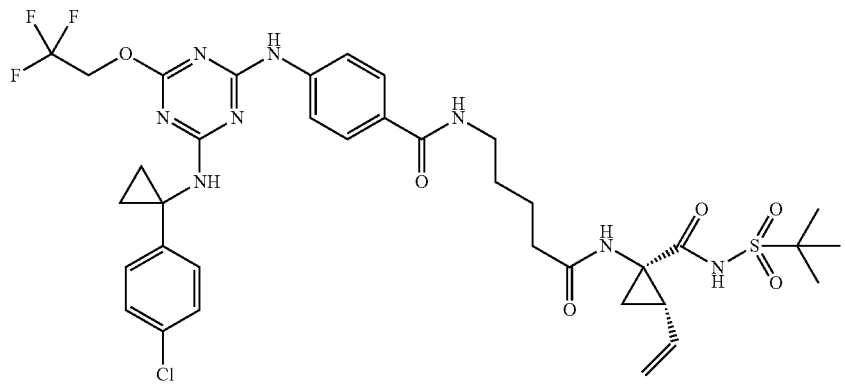

Compound 2027

The Compound 2027 was synthesized following the procedure reported in Scheme 2 of Example 2009. 5-Aminovalerate HCl and (1R,2S)-1-amino-N-(tert-butylsulfonyl)-2-vinylcyclopropanecarboxamide, HCl were used as starting material instead of ethyl 2-aminoacetate and methanesulfonamide. LC-MS (Condition A), MS m/z 807.1 (M⁺+H).

Example 2028

Preparation of Compound 2028

Compound 2028

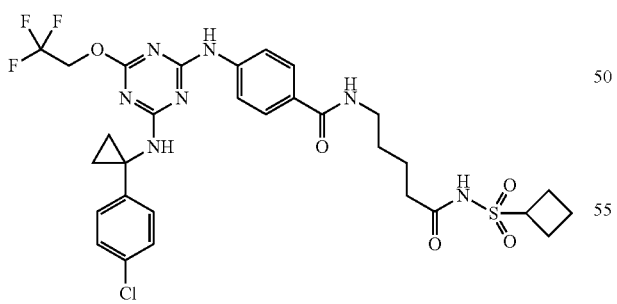

The Compound 2028 was synthesized following the procedure reported in Scheme 2 of Example 2009. 5-Aminovalerate HCl and cyclobutanesulfonamide were used as starting material instead of ethyl 2-aminoacetate and methanesulfonamide. LC-MS (Condition A), MS m/z 696.0 (M⁺+H).

Example 2029

Preparation of Compound 2029

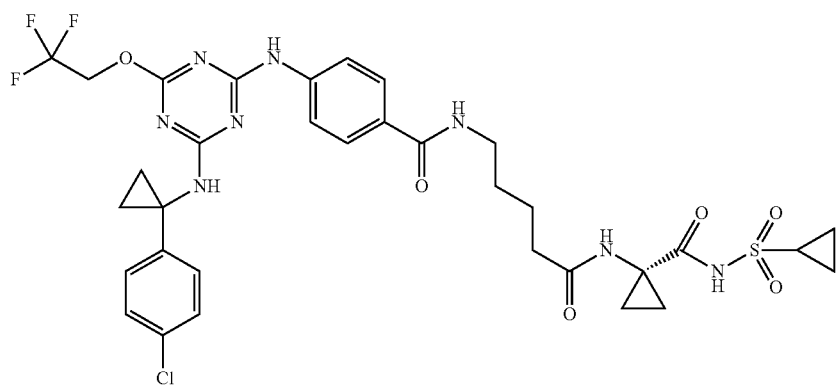

Compound 2029

The Compound 2029 was synthesized following the procedure reported in Scheme 2 of Example 2009. 5-Aminovalerate HCl and 1-amino-N-(cyclopropylsulfonyl)cyclopropanecarboxamide, HCl were used as starting material instead of ethyl 2-aminoacetate and methanesulfonamide. LC-MS (Condition A), MS m/z 765.0 (M$^+$+H).

Example 2030

Preparation of Compound 2030

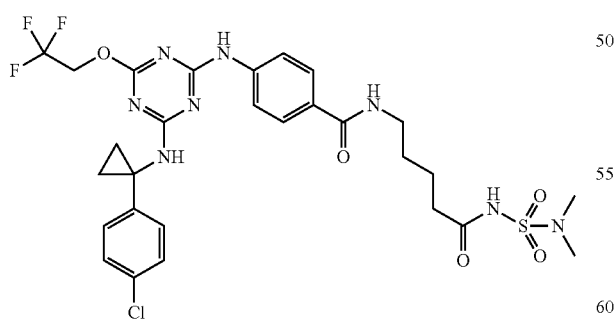

Compound 2030

The Compound 2030 was synthesized following the procedure reported in Scheme 2 of Example 2009. 5-Aminovalerate HCl and N,N-dimethylsulfamide were used as starting material instead of ethyl 2-aminoacetate and methanesulfonamide. LC-MS (Condition A), MS m/z 685.0 (M$^+$+H).

Example 2031

Preparation of Compound 2031

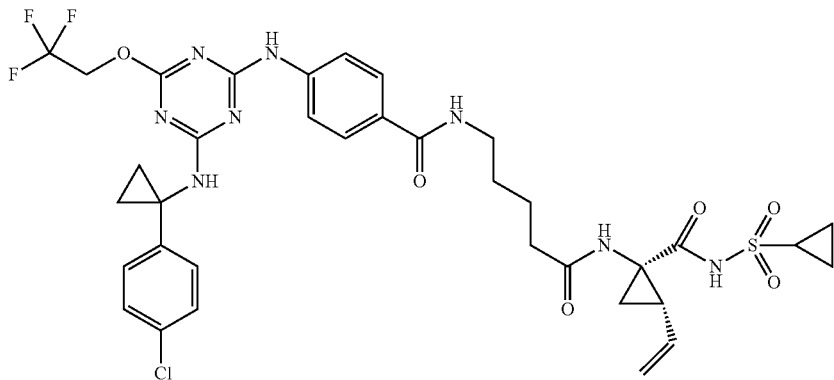

Compound 2031

The Compound 2031 was synthesized following the procedure reported in Scheme 2 of Example 2009. 5-Aminovalerate HCl and (1R,2S)-1-amino-N-(cyclopropylsulfonyl)-2-vinylcyclopropanecarboxamide, HCl were used as starting material instead of ethyl 2-aminoacetate and methanesulfonamide. LC-MS (Condition A), MS m/z 791.0 (M$^+$+H).

Example 2032

Preparation of Compound 2032

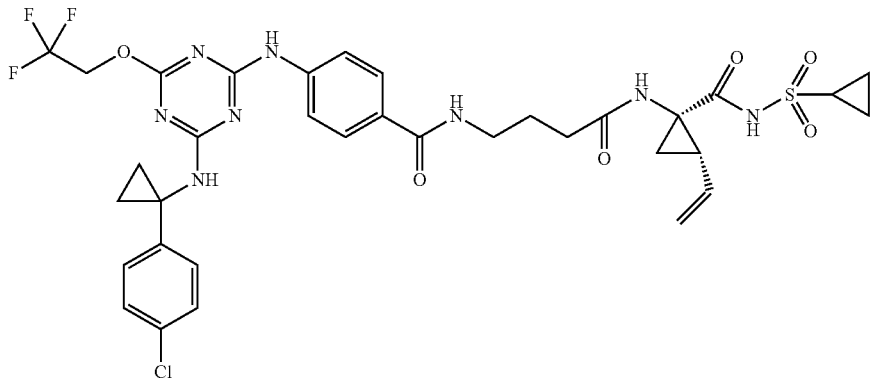

Compound 2032

The Compound 2032 was synthesized following the procedure reported in Scheme 2 of Example 2009. Ethyl 4-aminobutyrate and (1R,2S)-1-amino-N-(cyclobutylsulfonyl)-2-vinylcyclopropanecarboxamide, HCl were used as starting material instead of ethyl 2-aminoacetate and methanesulfonamide. LC-MS (Condition A), MS m/z 791.1 (M$^+$+H).

Example 2033

Preparation of Compound 2033

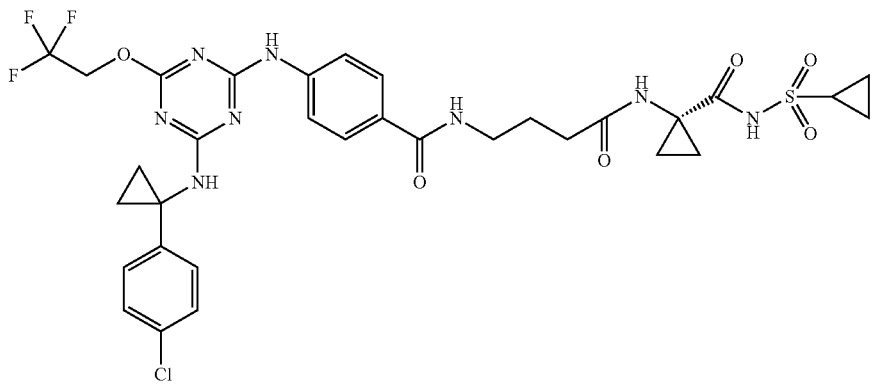

Compound 2033

The Compound 2033 was synthesized following the procedure reported in Scheme 2 of Example 2009. Ethyl 4-aminobutyrate and 1-amino-N-(cyclopropylsulfonyl)cyclopropanecarboxamide, HCl were used as starting material instead of ethyl 2-aminoacetate and methanesulfonamide. LC-MS (Condition A), MS m/z 751.0 (M$^+$+H).

Example 2034

Preparation of Compound 2034

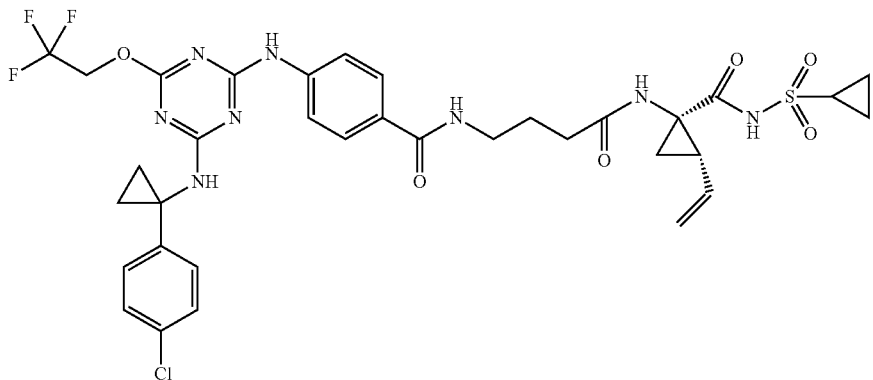

Compound 2034

The Compound 2034 was synthesized following the procedure reported in Scheme 2 of Example 2009. Ethyl 4-aminobutyrate and (1R,2S)-1-amino-N-(cyclopropylsulfonyl)-2-vinylcyclopropanecarboxamide, HCl were used as starting material instead of ethyl 2-aminoacetate and methanesulfonamide. LC-MS (Condition A), MS m/z 777.0 (M$^+$+H).

Example 2035

Preparation of Compound 2035

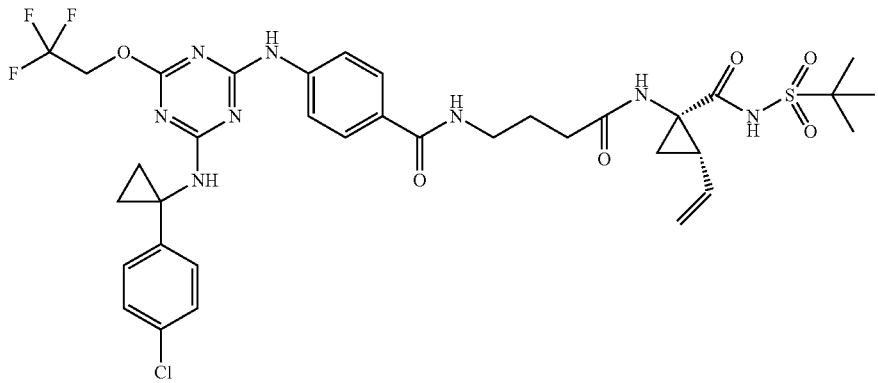

Compound 2035

The Compound 2035 was synthesized following the procedure reported in Scheme 2 of Example 2009. Ethyl 4-aminobutyrate and (1R,2S)-1-amino-N-(tert-butylsulfonyl)-2-vinylcyclopropanecarboxamide, HCl were used as starting material instead of ethyl 2-aminoacetate and methanesulfonamide. LC-MS (Condition A), MS m/z 793.0 (M$^+$+H).

Example 2036

Preparation of Compound 2036

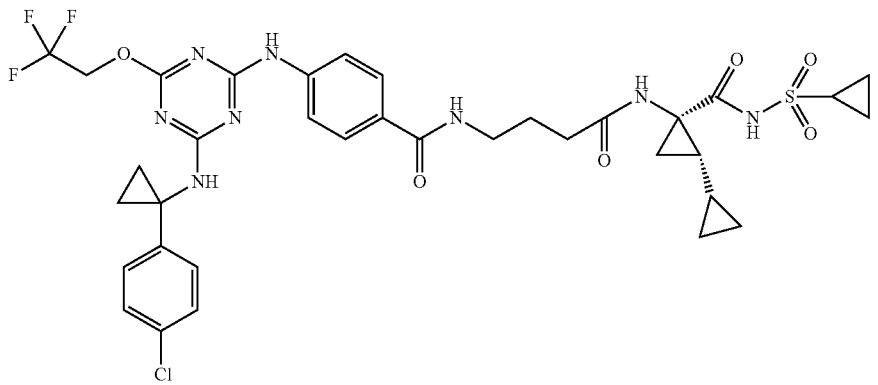

Compound 2036

The Compound 2036 was synthesized following the procedure reported in Scheme 2 of Example 2009. Ethyl 4-aminobutyrate and (1S,2R)-2-amino-N-(cyclopropylsulfonyl)bi(cyclopropane)-2-carboxamide, HCl were used as starting material instead of ethyl 2-aminoacetate and methanesulfonamide. LC-MS (Condition A), MS m/z 791.0 (M$^+$+H).

Example 2037

Preparation of Compound 2037

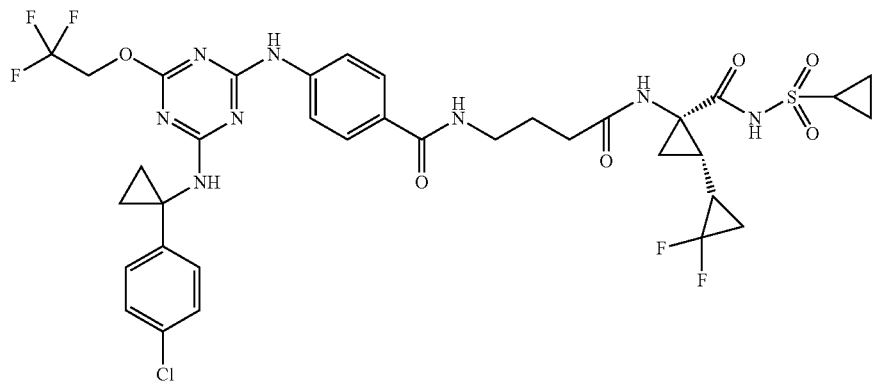

Compound 2037

The Compound 2037 was synthesized following the procedure reported in Scheme 2 of Example 2009. Ethyl 4-aminobutyrate and (1S,1'R,2R)-2-amino-N-(cyclopropylsulfonyl)-2',2'-difluorobi(cyclopropane)-2-carboxamide, Cl were used as starting material instead of ethyl 2-aminoacetate and methanesulfonamide. LC-MS (Condition A), MS m/z 827.0 ($M^+$+H).

Example 2038

Preparation of Compound 2038

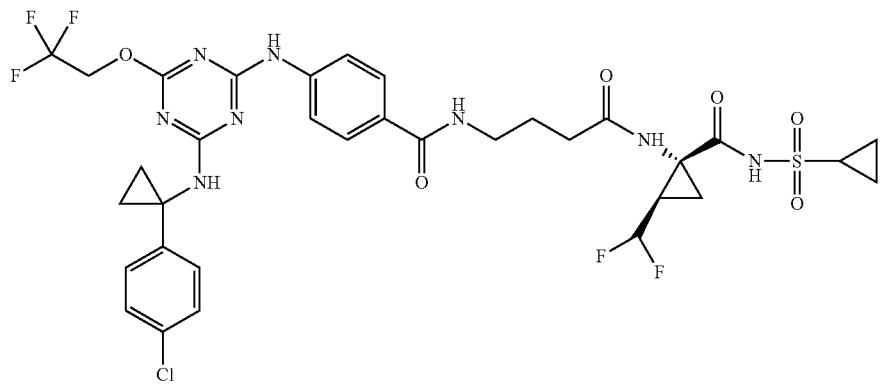

Compound 2038

The Compound 2038 was synthesized following the procedure reported in Scheme 2 of Example 2009. Ethyl 4-aminobutyrate and (1R,2R)-1-amino-N-(cyclopropylsulfonyl)-2-(difluoromethyl)cyclopropanecarboxamide, HCl were used as starting material instead of ethyl 2-aminoacetate and methanesulfonamide. LC-MS (Condition A), MS m/z 801.0 ($M^+$+H).

Example 2039
Preparation of Compound 2039
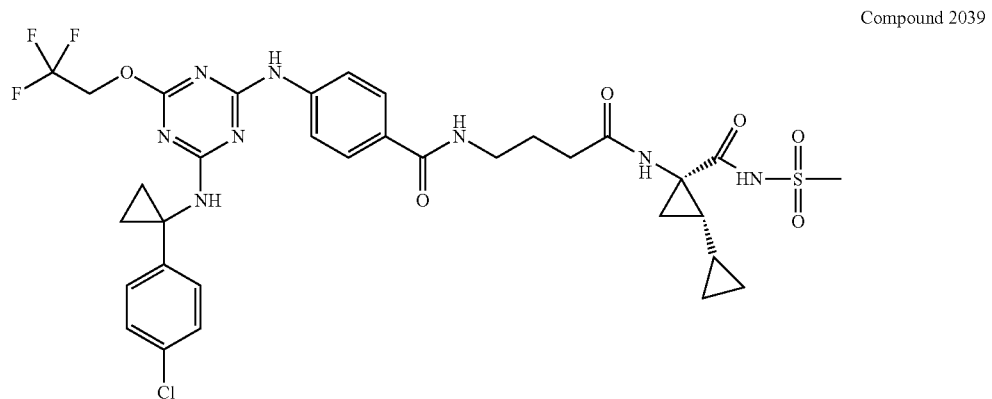 [SMILES: CS(=O)(=O)NC(=O)[C@@]1(NC(=O)CCCNC(=O)c2ccc(Nc3nc(NC4(c5ccc(Cl)cc5)CC4)nc(OCC(F)(F)F)n3)cc2)C[C@H]1C1CC1]
Compound 2039
Scheme 3
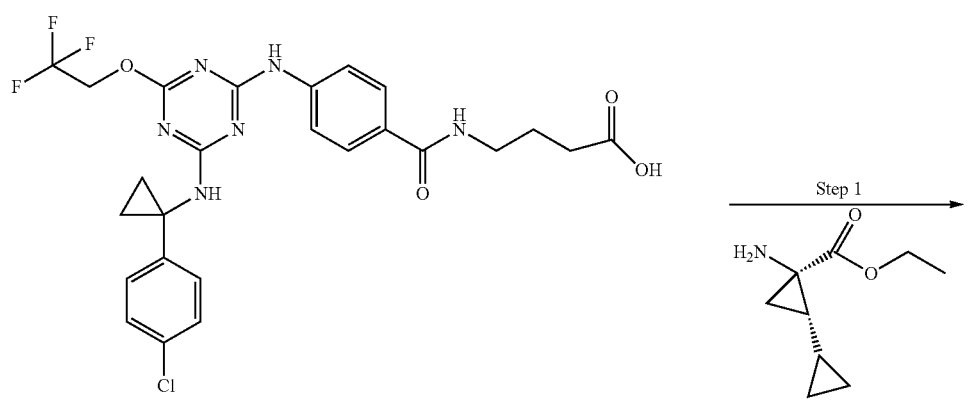
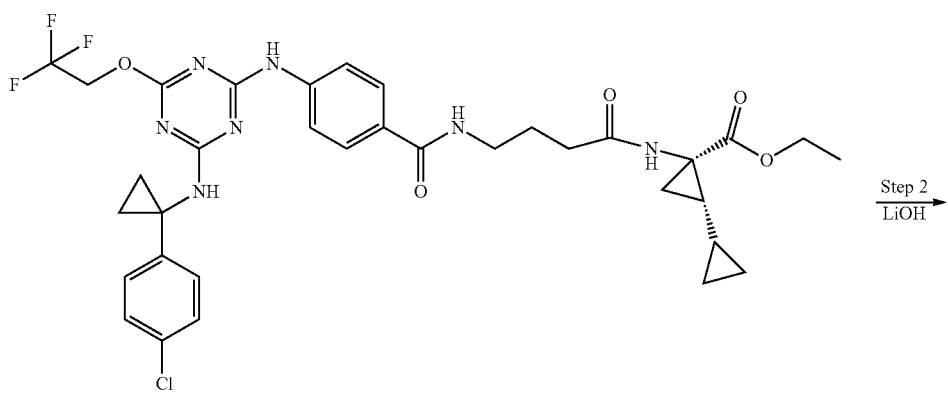

-continued

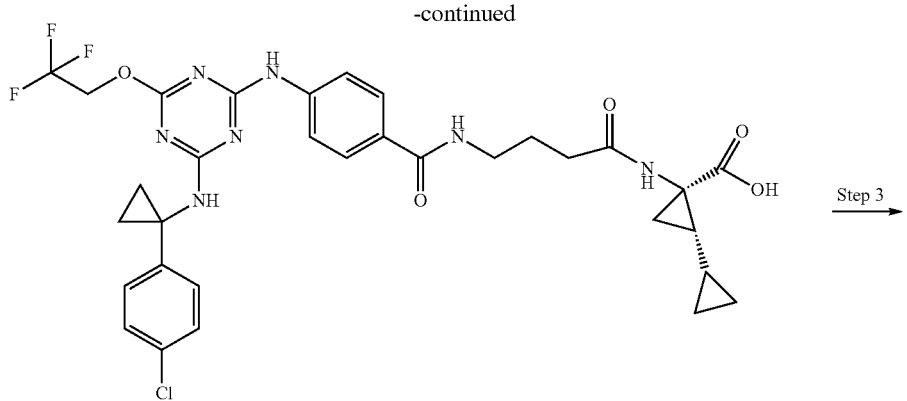

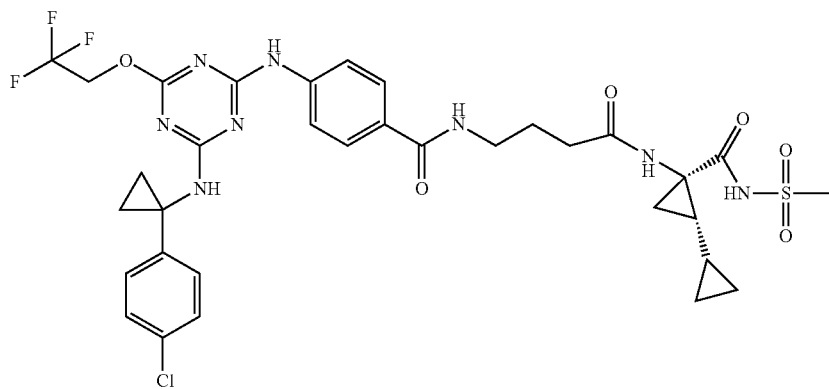

Step 1:
To a solution of 4-(4-(4-(1-(4-chlorophenyl)cyclopropylamino)-6-(2,2,2-trifluoroethoxy)-1,3,5-triazin-2-ylamino)benzamido)butanoic acid (300 mg, 0.53 mmol) in DCM (5 mL) was added (1S,2R)-ethyl 2-aminobi(cyclopropane)-2-carboxylate, HCl (131 mg, 0.64 mmol), HATU (303 mg, 0.80 mol) and iPr$_2$NEt (0.93 mL, 5.31 mmol). The mixture was stirred at r.t. for 16 hours before all the solvents were removed under vacuum. All solvents were removed under vacuum and the residue was purified by silica gel column (EtOAC/Hexanes=40% to 60%) to (1S,2R)-ethyl 2-(4-(4-(4-(1-(4-chlorophenyl)cyclopropylamino)-6-(O2,2,2-trifluoroethoxy)-1,3,5-triazin-2-ylamino)benzamido)butanamido)bi(cyclopropane)-2-carboxylate (370 mg, 97%) as a white solid. LC-MS (Condition A), MS m/z 685.0 (M$^+$+H).

Step 2:
To a suspension of 2-(4-(4-(4-(1-(4-chlorophenyl)cyclopropylamino)-6-(2,2,2-trifluoroethoxy)-1,3,5-triazin-2-ylamino)benzamido)butanamido)bi(cyclopropane)-2-carboxylate (370 mg, 0.52 mmol) in THF and water solution (6 mL, 1:1:1 ratio) was added LiOH (50 mg, 2.1 mmol). The mixture was heated at 65° C. for 16 hours. After cooling to room temperature, the reaction solution was acidified with 1N HCl. The product was extracted by EtOAc. The organic layer was washed with brine, dried over Na$_2$SO$_4$ and concentrated under vacuum. The crude product was used directly in the next step. LC-MS (Condition A), MS m/z 688.2 (M$^+$+H).

Step 3:
To a solution of (1S,2R)-2-(4-(4-(4-(1-(4-chlorophenyl)cyclopropylamino)-6-(2,2,2-trifluoroethoxy)-1,3,5-triazin-2-ylamino)benzamido)butanamido)bi(cyclopropane)-2-carboxylic acid (15 mg, 0.02 mmol) in THF solution was added CDI (7.0 mg, 0.04 mmol). The mixture was heated at 65° C. for 1 hour. After cooling to room temperature, methanesulfonamide (4.2 mg, 0.04 mmol) and DBU (9.9 ul, 0.07 mmol) were added to the mixture. The reaction mixture was stirred at r.t. for 16 hours. The solvent was evaporated and the residue was purified by preparative HPLC to afford 4-(4-(1-(4-chlorophenyl)cyclopropylamino)-6-(2,2,2-trifluoroethoxy)-1,3,5-triazin-2-ylamino)-N-(4-((1S,2R)-2-(methylsulfonylcarbamoyl)bi(cyclopropan-2-ylamino)-4-oxobutyl)benzamide (6.7 mg, 40%) as a white solid. 1H NMR (400 MHz, MeOD) δ ppm 0.34 (m, 2H), 0.57 (q, J=9.20 Hz, 2H), 0.71-0.80 (m, 1H), 1.08-1.13 (m, 1H), 1.18 (ddd, J=9.41, 7.53, 7.40 Hz, 1H), 1.34-1.45 (m, 4H), 1.77 (dd, J=7.53, 5.02 Hz, 1H), 1.85-1.97 (m, 1H), 2.26-2.36 (m, 2H), 2.37 (m, 2H), 3.26 (s, 3H), 3.41-3.51 (m, 1H), 4.00 (s, 2H), 7.23-7.33 (m, 4H), 7.60-7.75 (m, 3H), 7.85 (m, 1H); LC-MS (Condition A), MS m/z 765.1 (M$^+$+H).

Example 2040

Preparation of Compound 2040

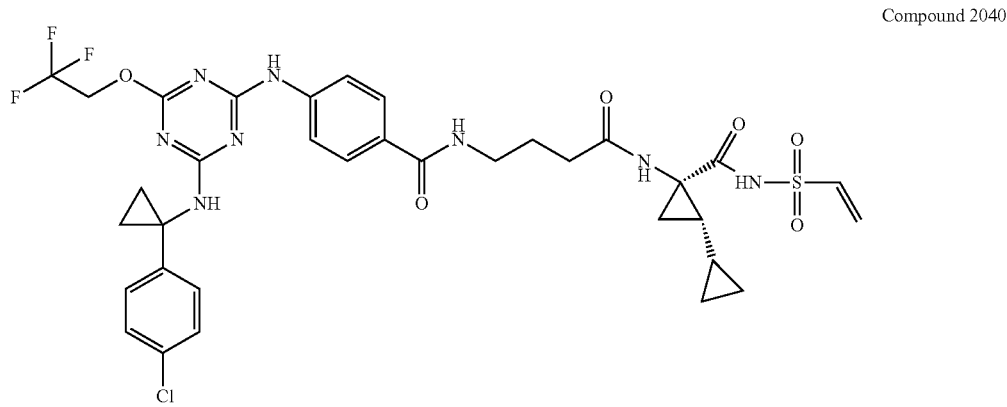 [SMILES: C=CS(=O)(=O)NC(=O)[C@@]1(NC(=O)CCCNC(=O)c2ccc(Nc3nc(NC4(c5ccc(Cl)cc5)CC4)nc(OCC(F)(F)F)n3)cc2)C[C@H]1C1CC1]

Compound 2040

The Compound 2040 was synthesized following the procedure reported in Scheme 3 of Example 2039. Ethenesulfonamide was used as starting material instead methanesulfonamide. $^1$H NMR (400 MHz, MeOD) δ ppm 0.32 (dd, J=4.64, 1.88 Hz, 2H), 0.50-0.56 (m, 2H), 0.70 (m, 1H), 1.10 (m, 2H), 1.34-1.44 (m, 4H), 1.73 (m 1H), 1.91 (m, 2H), 2.30 (d, J=6.53 Hz, 2H), 3.45 (m, 2H), 4.92 (s, 2H), 6.15 (d, J=9.79 Hz, 1H), 6.41 (d, J=16.56 Hz, 1H), 6.93 (dd, J=16.56, 10.04 Hz, 1H), 7.23-7.34 (m, 4H), 7.62-7.70 (m, 2H), 7.85 (m, 1H); LC-MS (Condition A), MS m/z 777.1 (M$^+$+H).

Example 2041

Preparation of Compound 2041

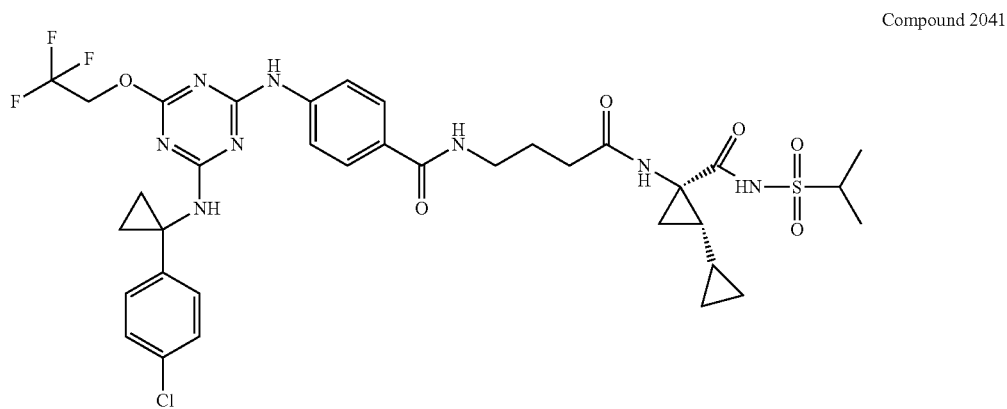 [SMILES: CN(C)S(=O)(=O)NC(=O)[C@@]1(NC(=O)CCCNC(=O)c2ccc(Nc3nc(NC4(c5ccc(Cl)cc5)CC4)nc(OCC(F)(F)F)n3)cc2)C[C@H]1C1CC1]

Compound 2041

The Compound 2041 was synthesized following the procedure reported in Scheme 3 of Example 2039. Propane-2-sulfonamide was used as starting material instead methanesulfonamide. $^1$H NMR (400 MHz, MeOD) δ ppm 0.34 (dd, J=4.89, 1.38 Hz, 2H), 0.50-0.61 (m, 2H), 0.75 (m, 1H), 1.08-1.19 (m, 2H), 1.38 (m, 10H), 1.77 (dd, J=7.40, 4.89 Hz, 1H), 1.87 (m, 1H), 1.95 (d, J=6.53 Hz, 1H), 2.25-2.35 (m, 2H), 3.46-3.55 (m, 2H), 3.72-3.82 (m, 1H), 4.91 (s, 2H), 7.29 (ddd, J=15.87, 6.59, 2.13 Hz, 4H), 7.61-7.76 (m, 3H), 7.85 (m, 1H); LC-MS (Condition A), MS m/z 793.1 (M$^+$+H).

Example 2042

Preparation of Compound 2042

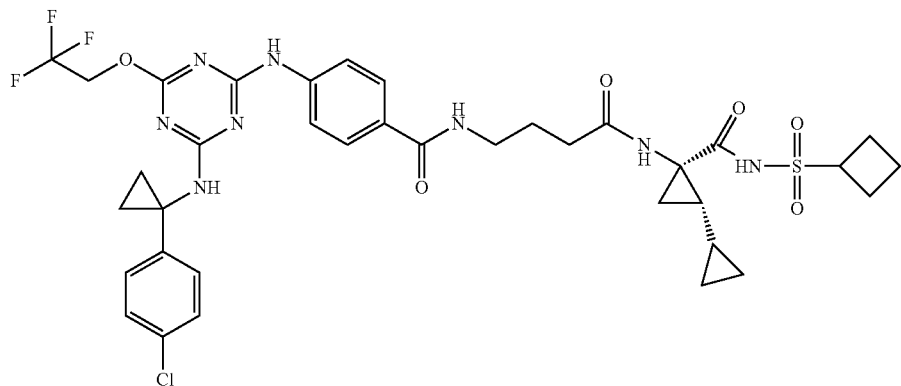

Compound 2042

The Compound 2042 was synthesized following the procedure reported in Scheme 3 of Example 2039. Cyclobutanesulfonamide was used as starting material instead methanesulfonamide. LC-MS (Condition A), MS m/z 805.1 ($M^+$+H).

Example 2043

Preparation of Compound 2043

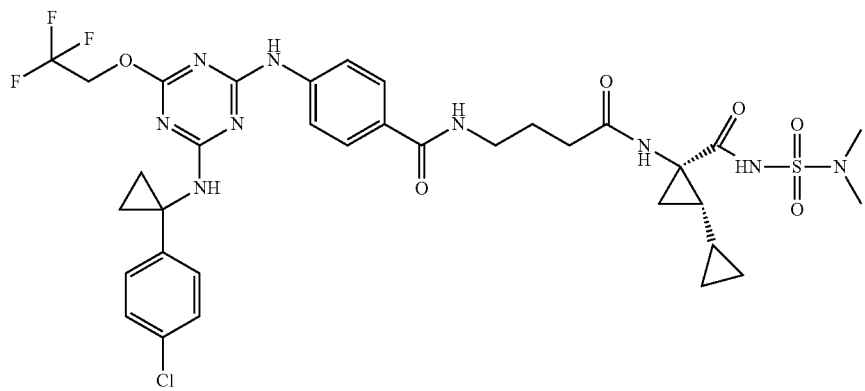

Compound 2043

The Compound 2043 was synthesized following the procedure reported in Scheme 3 of Example 2039. N,N-dimethylsulfamide was used as starting material instead methanesulfonamide. LC-MS (Condition A), MS m/z 794.1 ($M^+$+H).

Example 2044

Preparation of Compound 2044

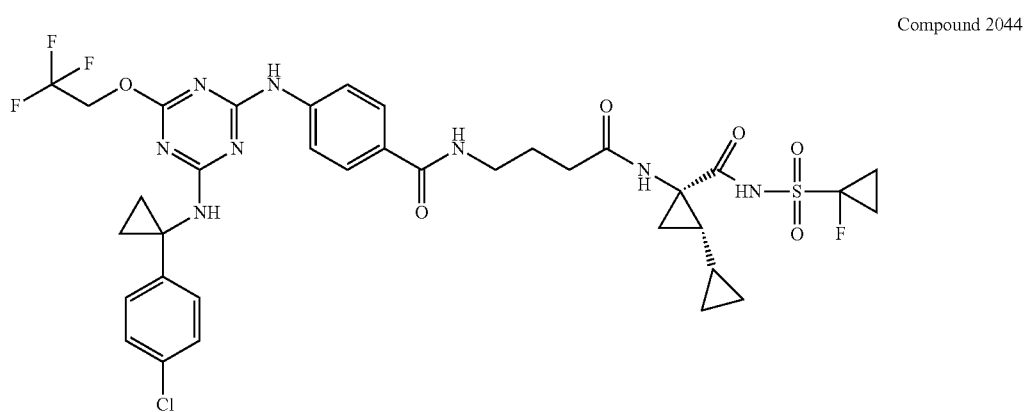 [SMILES: O=C(CCCNC(=O)c1ccc(Nc2nc(NC3(c4ccc(Cl)cc4)CC3)nc(OCC(F)(F)F)n2)cc1)N[C@]1(C(=O)NS(=O)(=O)C2(F)CC2)C[C@H]1C1CC1]

Compound 2044

The Compound 2044 was synthesized following the procedure reported in Scheme 3 of Example 2039. 1-Fluorocyclopropane-1-sulfonamide was used as starting material instead methanesulfonamide. LC-MS (Condition A), MS m/z 809.1 (M$^+$+H).

Example 2045

Preparation of Compound 2045

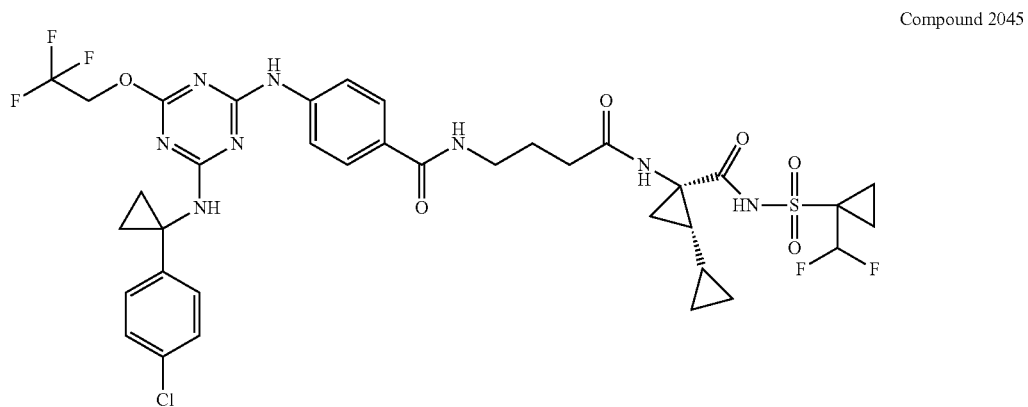 [SMILES: O=C(CCCNC(=O)c1ccc(Nc2nc(NC3(c4ccc(Cl)cc4)CC3)nc(OCC(F)(F)F)n2)cc1)N[C@]1(C(=O)NS(=O)(=O)C2(C(F)F)CC2)C[C@H]1C1CC1]

Compound 2045

The Compound 2045 was synthesized following the procedure reported in Scheme 3 of Example 2039. 1-(difluoromethyl)cyclopropane-1-sulfonamide was used as starting material instead methanesulfonamide. LC-MS (Condition A), MS m/z 841.1 (M$^+$+H).

Example 2046

Preparation of Compound 2046

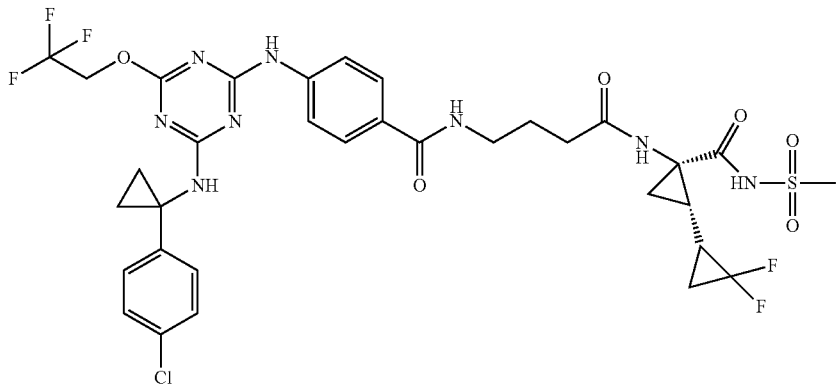

Compound 2046

The Compound 2046 was synthesized following the procedure reported in Scheme 3 of Example 2039. (1S,1'S,2R)-ethyl 2-amino-2',2'-difluorobi(cyclopropane)-2-carboxylate, HCl was used as starting material (1S,2R)-ethyl 2-aminobi(cyclopropane)-2-carboxylate, HCl. LC-MS (Condition A), MS m/z 801.1 (M$^+$+H).

Example 2047

Preparation of Compound 2047

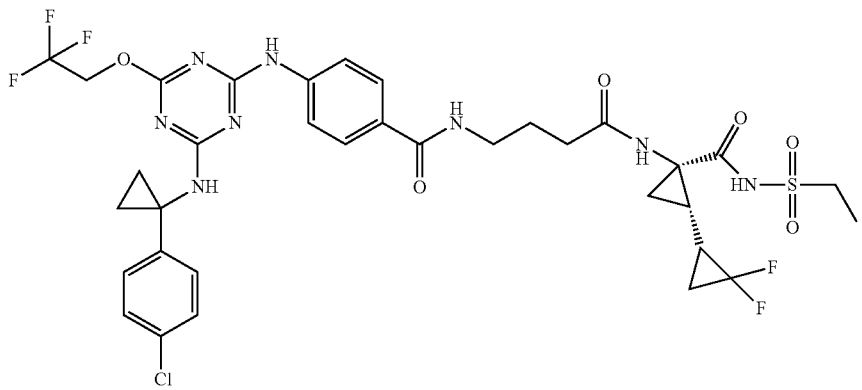

Compound 2047

The Compound 2047 was synthesized following the procedure reported in Scheme 3 of Example 2039. (1S,1'S,2R)-ethyl 2-amino-2',2'-difluorobi(cyclopropane)-2-carboxylate, HCl and ethanesulfonamide were used as starting material instead of (1S,2R)-ethyl 2-aminobi(cyclopropane)-2-carboxylate, HCl and methanesulfonamide. LC-MS (Condition A), MS m/z 816.1 (M$^+$+H).

Example 2048

Preparation of Compound 2048

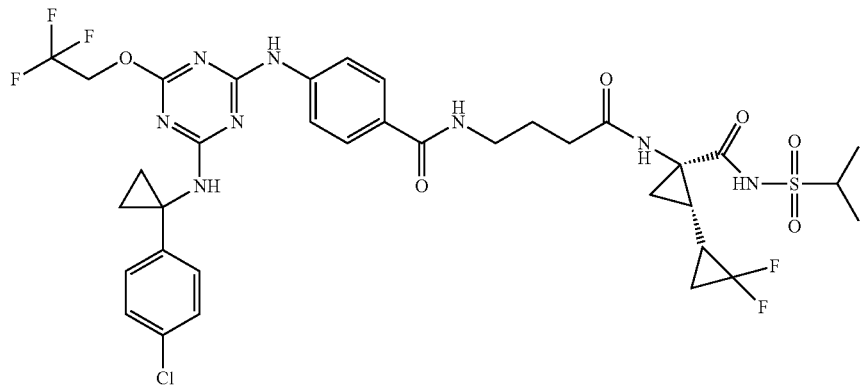

Compound 2048

The Compound 2048 was synthesized following the procedure reported in Scheme 3 of Example 2039. (1S,1'S,2R)-ethyl 2-amino-2',2'-difluorobi(cyclopropane)-2-carboxylate, HCl and Propane-2-sulfonamide were used as starting material instead of (1S,2R)-ethyl 2-aminobi(cyclopropane)-2-carboxylate, HCl and methanesulfonamide. LC-MS (Condition A), MS m/z 830.1 (M$^+$+H).

Example 2049

Preparation of Compound 2049

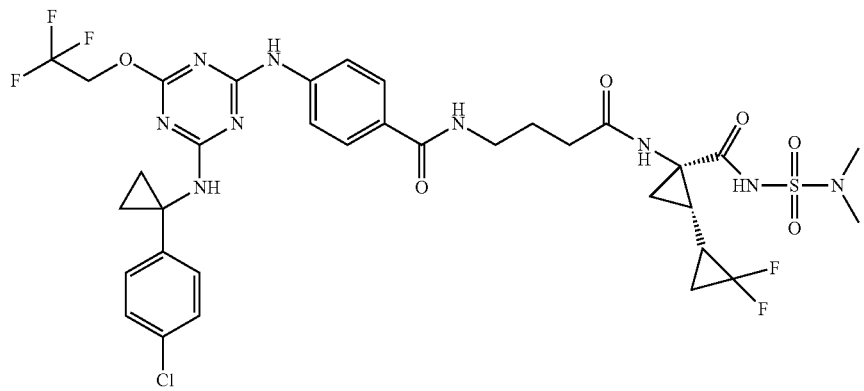

Compound 2049

The Compound 2049 was synthesized following the procedure reported in Scheme 3 of Example 2039. (1S,1'S,2R)-ethyl 2-amino-2',2'-difluorobi(cyclopropane)-2-carboxylate, HCl and N,N-dimethylsulfamide were used as starting material instead of (1S,2R)-ethyl 2-aminobi(cyclopropane)-2-carboxylate, HCl and methanesulfonamide. LC-MS (Condition A), MS m/z 811.1 (M$^+$+H).

Example 2050

Preparation of Compound 2050

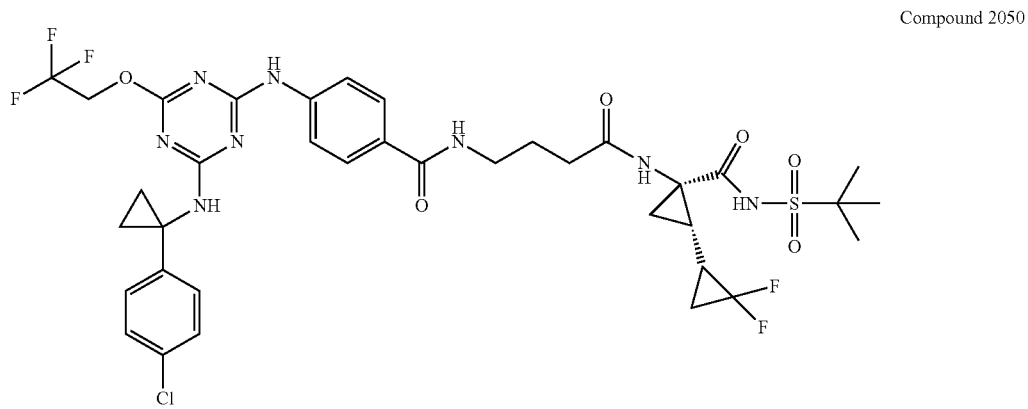 [SMILES: CC(C)(C)S(=O)(=O)NC(=O)[C@@]1(NC(=O)CCCNC(=O)c2ccc(Nc3nc(NC4(c5ccc(Cl)cc5)CC4)nc(OCC(F)(F)F)n3)cc2)C[C@H]1C1CC1(F)F]

Compound 2050

The Compound 2050 was synthesized following the procedure reported in Scheme 3 of Example 2039. (1S,1'S,2R)-ethyl 2-amino-2',2'-difluorobi(cyclopropane)-2-carboxylate, HCl and 2-methylpropane-2-sulfonamide were used as starting material instead of (1S,2R)-ethyl 2-aminobi(cyclopropane)-2-carboxylate, HCl and methanesulfonamide. LC-MS (Condition A), MS m/z 844.1 (M$^+$+H).

Example 2051

Preparation of Compound 2051

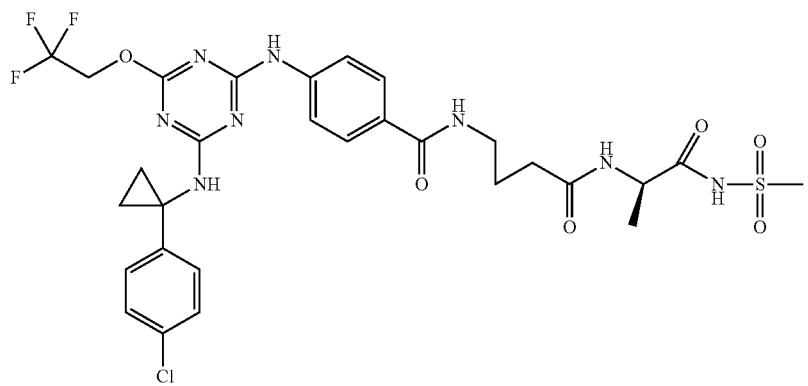

Compound 2051

Scheme 4
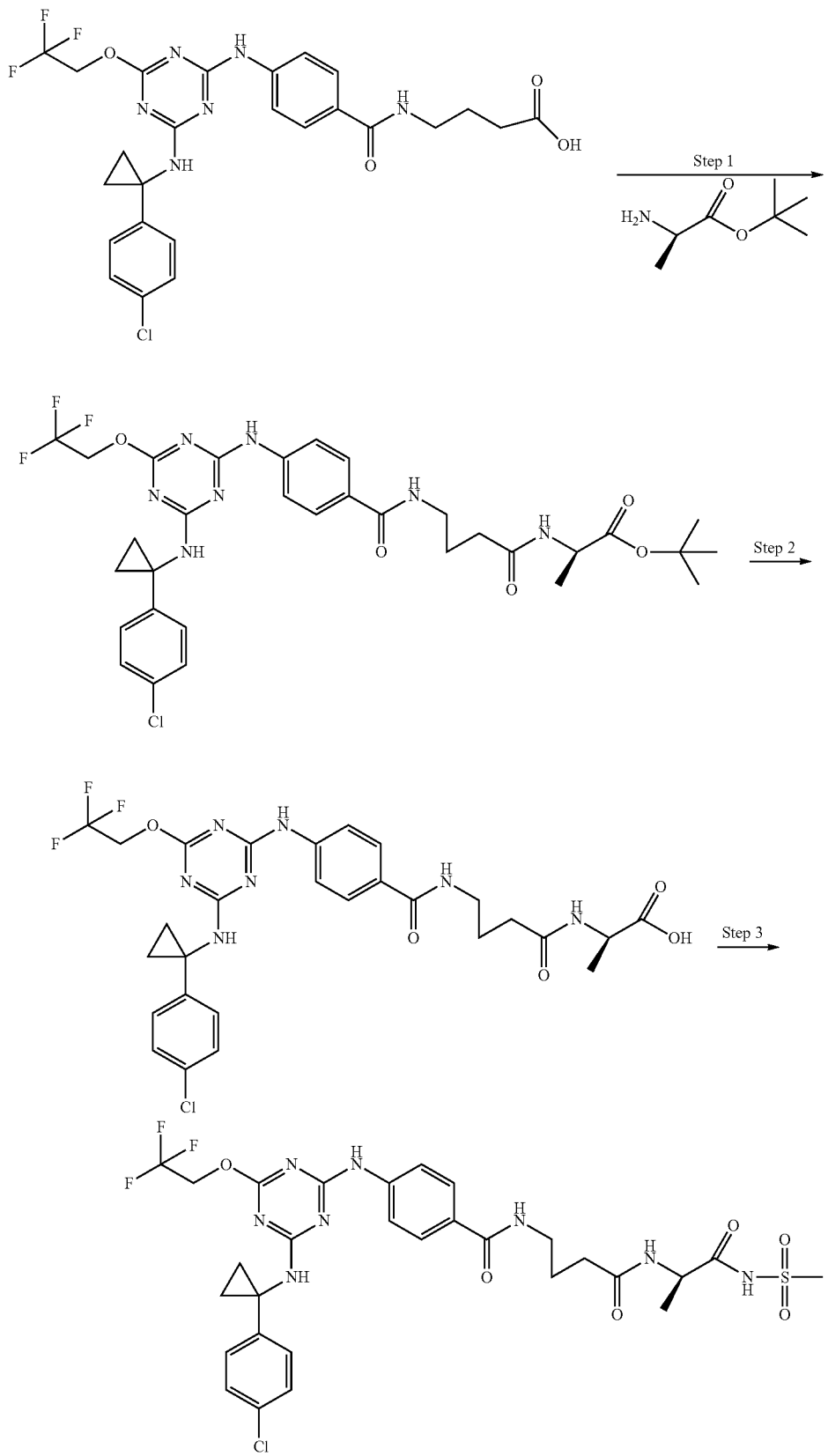

Step 1:

To a solution of 4-(4-(4-(1-(4-chlorophenyl)cyclopropylamino)-6-(2,2,2-trifluoroethoxy)-1,3,5-triazin-2-ylamino)benzamido)butanoic acid (300 mg, 0.53 mmol) in DCM (5 mL) was added (R)-tert-butyl 2-aminopropanoate, HCl (193 mg, 1.06 mmol), HATU (303 mg, 0.80 mol) and iPr$_2$NEt (0.93 mL, 5.31 mmol). The mixture was stirred at r.t. for 16 hours before all the solvents were removed under vacuum. All solvents were removed under vacuum and the residue was purified by silica gel column (EtOAC/Hexanes=40% to 100%) to give (R)-tert-butyl 2-(4-(4-(4-(1-(4-chlorophenyl)cyclopropylamino)-6-(2,2,2-trifluoroethoxy)-1,3,5-triazin-2-ylamino)benzamido)butanamido)propanoate (200 mg, 54%) as a white solid. LC-MS (Condition A), MS m/z 692.1 (M$^+$+H).

Step 2:

(R)-tert-butyl 2-(4-(4-(4-(1-(4-chlorophenyl)cyclopropylamino)-6-(2,2,2-trifluoroethoxy)-1,3,5-triazin-2-ylamino)benzamido)butanamido)propanoate (200 mg, 0.29 mmol) in 4 M HCl dioxane solution was stirred at r.t. for 3 hours. All solvents were removed under vacuum to give product. The crude product was used directly in the next step. LC-MS (Condition A), MS m/z 636.0 (M$^+$+H).

Step 3:

To a solution of (R)-2-(4-(4-(4-(1-(4-chlorophenyl)cyclopropylamino)-6-(2,2,2-trifluoroethoxy)-1,3,5-triazin-2-ylamino)benzamido)butanamido)propanoic acid, HCl (15 mg, 0.02 mmol) in THF solution was added CDI (7.0 mg, 0.04 mmol). The mixture was heated at 65° C. for 1 hour. After cooling to room temperature, methanesulfonamide (4.2 mg, 0.04 mmol) and DBU (9.9 ul, 0.07 mmol) were added to the mixture. The reaction mixture was stirred at r.t. for 16 hours. The solvent was evaporated and the residue was purified by preparative HPLC to afford (R)-4-(4-(1-(4-chlorophenyl)cyclopropylamino)-6-(2,2,2-trifluoroethoxy)-1,3,5-triazin-2-ylamino)-N-(4-(1-(methylsulfonamido)-1-oxopropan-2-ylamino)-4-oxobutyl)benzamide (5.9 mg, 33%) as a white solid. 1H NMR (400 MHz, MeOD) δ ppm 1.40 (m, 6H), 1.94 (m, 2H), 2.37 (m, 2H), 3.25 (s, 3H), 3.35 (s, 3H), 3.44 (dd, J=5.52, 2.76 Hz, 2H), 4.28 (m, 1H), 7.28 (m, 4H), 7.67 (m, 3H), 7.84 (m, 1H); LC-MS (Condition A), MS m/z 713.0 (M$^+$+H).

Example 2052

Preparation of Compound 2052

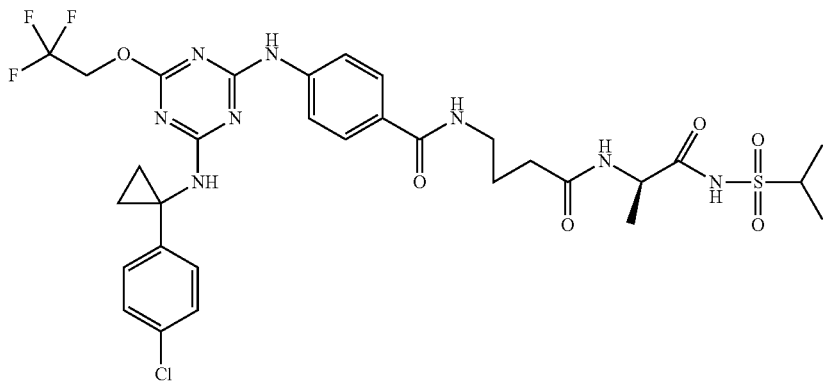

Compound 2052

The Compound 2052 was synthesized following the procedure reported in Scheme 4 of Example 2051. Propane-2-sulfonamide was used as starting material instead methanesulfonamide. 1H NMR (400 MHz, MeOD) δ ppm 1.34-1.43 (m, 10H), 1.88-1.98 (m, 2H), 2.29-2.40 (m, 2H), 3.40-3.51 (m, 2H), 3.65-3.75 (m, 1H), 4.28 (m, 1H), 4.92 (m, 2H), 7.23-7.33 (m, 4H), 7.61-7.72 (m, 3H), 7.80-7.91 (m, 1H); LC-MS (Condition A), MS m/z 741.1 (M$^+$+H).

Example 2053

Preparation of Compound 2053

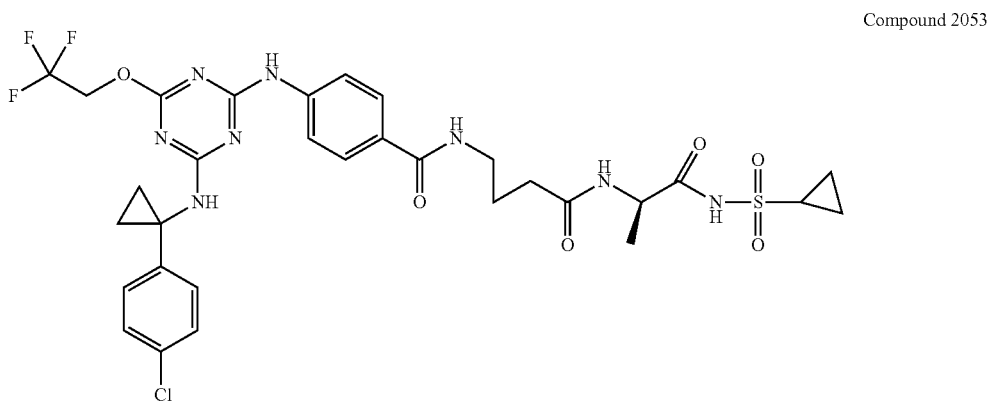 [SMILES: C[C@@H](NC(=O)CCCNC(=O)c1ccc(Nc2nc(NC3(c4ccc(Cl)cc4)CC3)nc(OCC(F)(F)F)n2)cc1)C(=O)NS(=O)(=O)C1CC1]

Compound 2053

The Compound 2053 was synthesized following the procedure reported in Scheme 4 of Example 2051. Cyclopropanesulfonamide was used as starting material instead methanesulfonamide. 1H NMR (400 MHz, MeOD) δ ppm 1.06-1.16 (m, 2H), 1.20-1.32 (m, 2H), 1.34-1.44 (m, 7H), 1.90-1.99 (m, 2H), 2.30-2.40 (m, 2H), 2.96 (m 1H), 3.38-3.47 (m, 2H), 4.32 (m, 1H), 4.92 (m, 2H), 7.24-7.33 (m, 4H), 7.62-7.72 (m, 3H), 7.83 (m, 1H); LC-MS (Condition A), MS m/z 739.1 ($M^+$+H).

Example 2054

Preparation of Compounds 2054

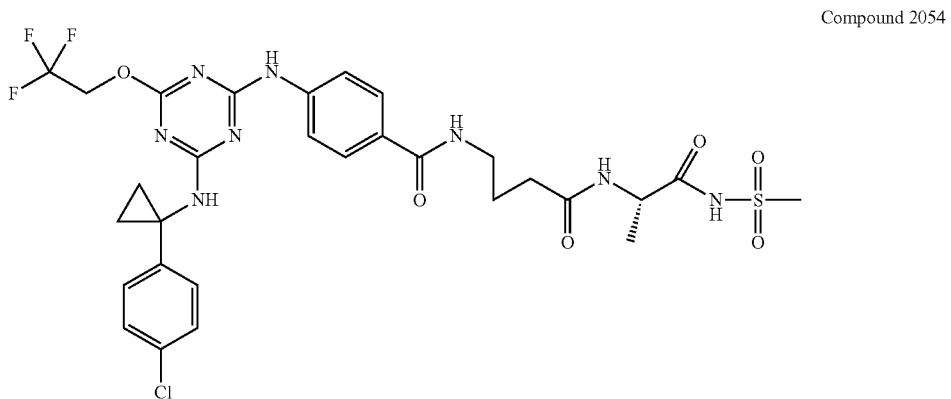 [SMILES: C[C@H](NC(=O)CCCNC(=O)c1ccc(Nc2nc(NC3(c4ccc(Cl)cc4)CC3)nc(OCC(F)(F)F)n2)cc1)C(=O)NS(C)(=O)=O]

Compound 2054

The Compound 2054 was synthesized following the procedure reported in Scheme 4 of Example 2051. (5)-tert-Butyl 2-aminopropanoate, HCl was used as starting material instead (R)-tert-butyl 2-aminopropanoate, HCl. LC-MS (Condition A), MS m/z 713.1 ($M^+$+H).

Example 2055

Preparation of Compound 2055

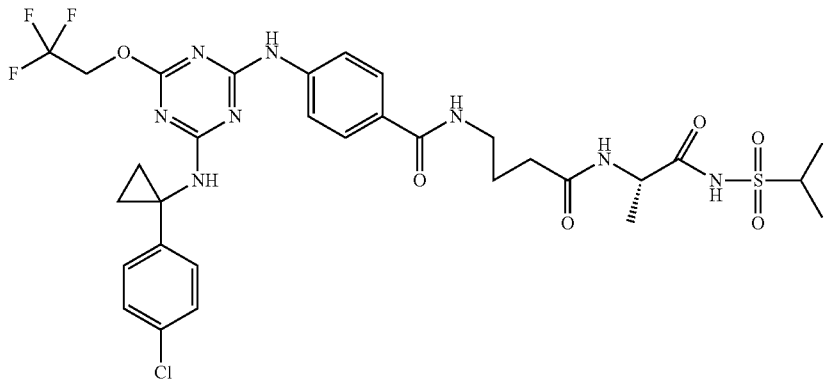

Compound 2055

The Compound 2055 was synthesized following the procedure reported in Scheme 4 of Example 2051. (S)-tert-butyl 2-aminopropanoate, HCl and propane-2-sulfonamide were used as starting material instead (R)-tert-butyl 2-aminopropanoate, HCl and methanesulfonamide. LC-MS (Condition A), MS m/z 741.1 ($M^+ +H$).

Example 2056

Preparation of Compound 2056

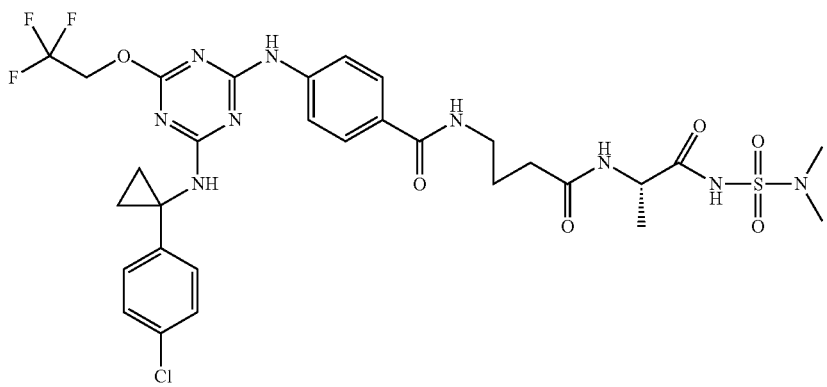

Compound 2056

The Compound 2056 was synthesized following the procedure reported in Scheme 4 of Example 2051. (S)-tert-butyl 2-aminopropanoate, HCl and N,N-dimethylsulfamide were used as starting material instead (R)-tert-butyl 2-aminopropanoate, HCl and methanesulfonamide. LC-MS (Condition A), MS m/z 742.1 ($M^+ +H$).

Example 2057

Preparation of Compounds 2057

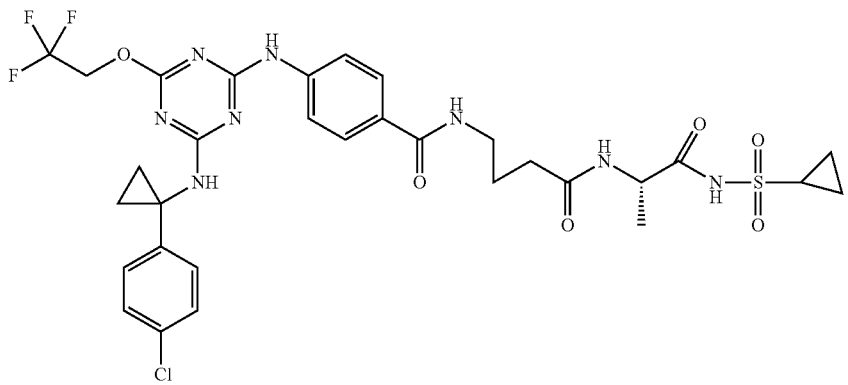

Compound 2057

The Compound 2057 was synthesized following the procedure reported in Scheme 4 of Example 2051. (5)-tert-butyl 2-aminopropanoate, HCl and cyclopropanesulfonamide were used as starting material instead (R)-tert-butyl 2-aminopropanoate, HCl and methanesulfonamide. LC-MS (Condition A), MS m/z 739.0 (M$^+$+H).

Example 2058

Preparation of Compound 2058

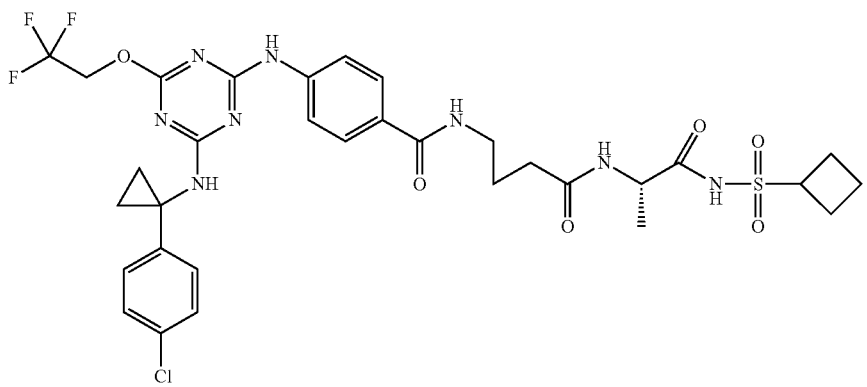

Compound 2058

The Compound 2058 was synthesized following the procedure reported in Scheme 4 of Example 2051. (5)-tert-butyl 2-aminopropanoate, HCl and cyclobutanesulfonamide were used as starting material instead (R)-tert-butyl 2-aminopropanoate, HCl and methanesulfonamide. LC-MS (Condition A), MS m/z 753.1 (M$^+$+H).

Example 2059

Preparation of Compound 2059

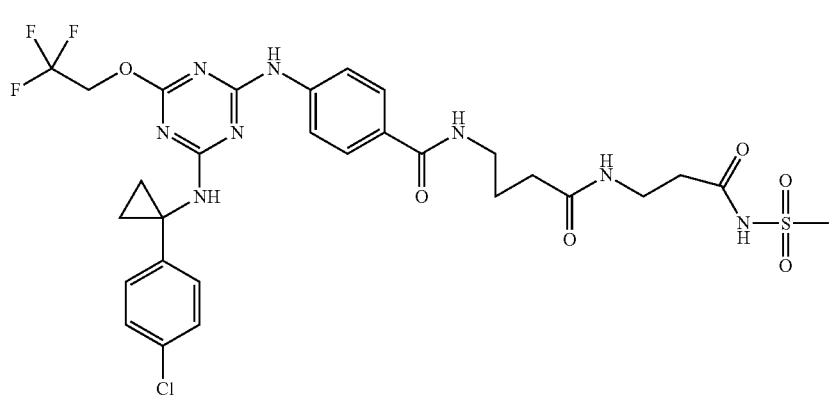

Compound 2059

The Compound 2059 was synthesized following the procedure reported in Scheme 4 of Example 2051. tert-Butyl 3-aminopropanoate was used as starting material instead (R)-tert-butyl 2-aminopropanoate, HCl. LC-MS (Condition A), MS m/z 713.3 ($M^+ +H$).

Example 2060

Preparation of Compounds 2060

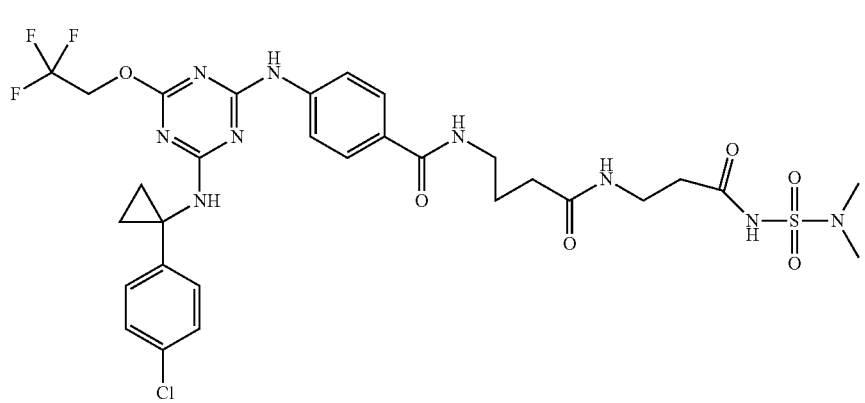

Compound 2060

The Compound 2060 was synthesized following the procedure reported in Scheme 4 of Example 2051. tert-Butyl 3-aminopropanoate and N,N-dimethylsulfamide were used as starting material instead (R)-tert-butyl 2-aminopropanoate, HCl and methanesulfonamide. LC-MS (Condition A), MS m/z 742.3 ($M^+ +H$).

Example 2061

Preparation of Compound 2061

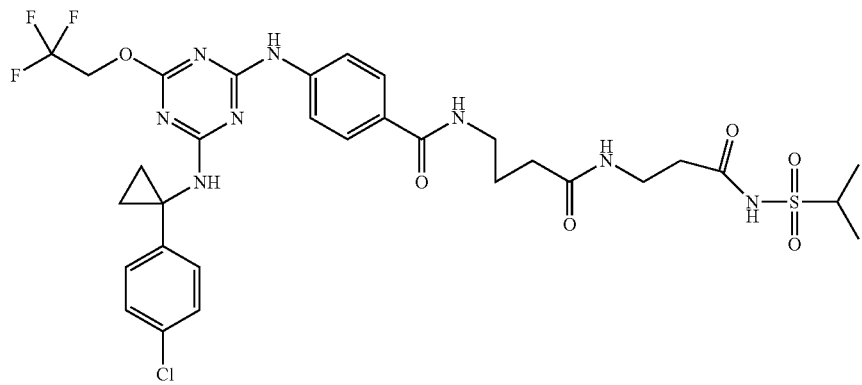

Compound 2061

The Compound 2061 was synthesized following the procedure reported in Scheme 4 of Example 2051. tert-Butyl 3-aminopropanoate and propane-2-sulfonamide were used as starting material instead (R)-tert-butyl 2-aminopropanoate, HCl and methanesulfonamide. LC-MS (Condition A), MS m/z 741.4 (M$^+$+H).

Example 2062

Preparation of Compound 2062

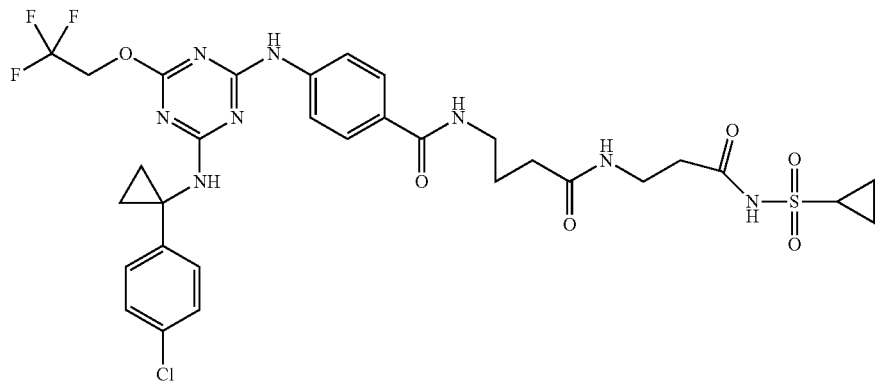

Compound 2062

The Compound 2062 was synthesized following the procedure reported in Scheme 4 of Example 2051. tert-Butyl 3-aminopropanoate and cyclopropanesulfonamide were used as starting material instead (R)-tert-butyl 2-aminopropanoate, HCl and methanesulfonamide. LC-MS, MS m/z 739.3 (M$^+$+H).

Example 1063

Preparation of Compound 2063

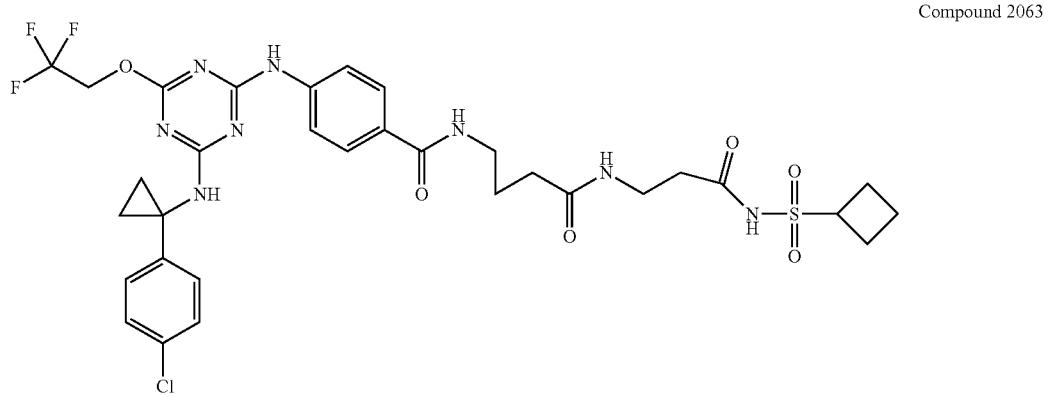 [SMILES: O=C(CCCNC(=O)c1ccc(Nc2nc(NC3(c4ccc(Cl)cc4)CC3)nc(OCC(F)(F)F)n2)cc1)NCCC(=O)NS(=O)(=O)C1CCC1]

Compound 2063

The Compound 2063 was synthesized following the procedure reported in Scheme 4 of Example 2051. tert-Butyl 3-aminopropanoate and cyclobutanesulfonamide were used as starting material instead (R)-tert-butyl 2-aminopropanoate, HCl and methanesulfonamide. LC-MS (Condition A), MS m/z 753.4 (M$^+$+H).

Example 2064

Preparation of Compound 2064

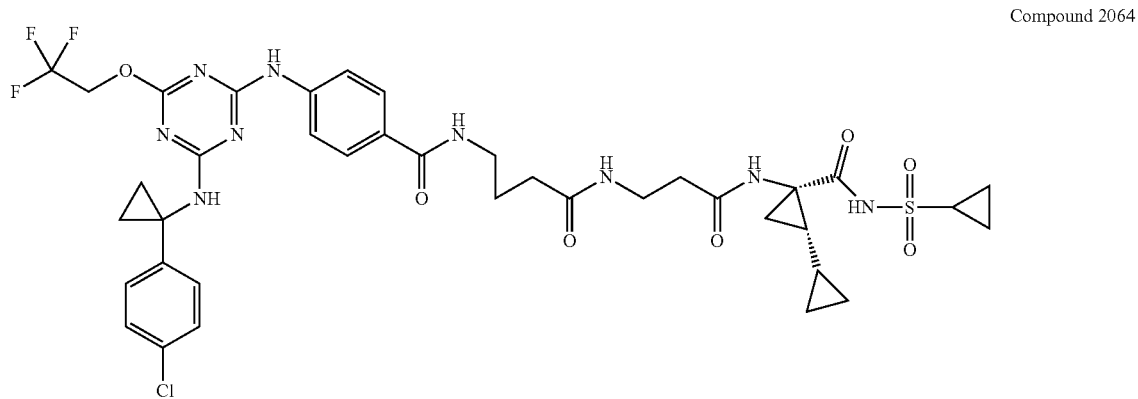 [SMILES: O=C(CCCNC(=O)c1ccc(Nc2nc(NC3(c4ccc(Cl)cc4)CC3)nc(OCC(F)(F)F)n2)cc1)NCCC(=O)N[C@]1(C(=O)NS(=O)(=O)C2CC2)C[C@H]1C1CC1]

Compound 2064

The Compound 1064 was synthesized following the procedure reported in Scheme 4 of Example 2051. tert-Butyl 3-aminopropanoate and (1S,2R)-2-amino-N-(cyclopropylsulfonyl)bi(cyclopropane)-2-carboxamide were used as starting material instead (R)-tert-butyl 2-aminopropanoate, HCl and methanesulfonamide. LC-MS (Condition A), MS m/z 862.4 (M$^+$+H).

Example 2065

Preparation of Compound 2065

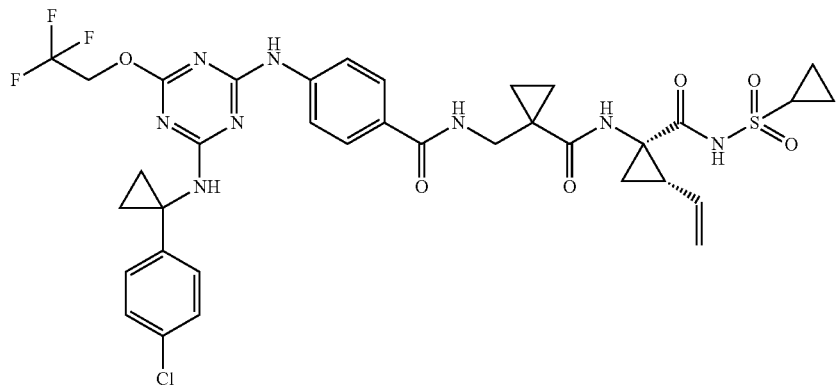

Compound 2065

The Compound 2065 was synthesized following the procedure reported in Scheme 2 of Example 2009. Methyl 1-(aminomethyl)cyclopropanecarboxylate, HCl and (1R, 2S)-1-amino-N-(cyclopropylsulfonyl)-2-vinylcyclopropanecarboxamide, HCl were used as starting material instead of ethyl 2-aminoacetate and methanesulfonamide in Steps 1 and 3, respectively, to give 20 mg (46%) of compound 2065. LC-MS (Condition A), MS m/z 789.23 (M$^+$+H).

Example 2066

Preparation of Compound 2066

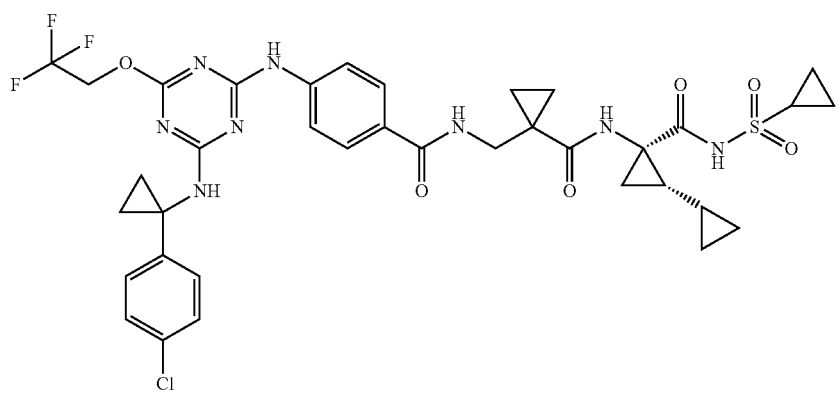

Compound 2066

The Compound 2066 was synthesized following the procedure reported in Scheme 2 of Example 2009. Methyl 1-(aminomethyl)cyclopropanecarboxylate, HCl and (1S, 2R)-2-amino-N-(cyclopropylsulfonyl)bi(cyclopropane)-2-carboxamide, HCl were used as starting material instead of ethyl 2-aminoacetate and methanesulfonamide in Steps 1 and 3, respectively, to give 26 mg of compound 2066. LC-MS (Condition A), MS m/z 803.23 (M$^+$+H).

Example 2067

Preparation of Compound 2067

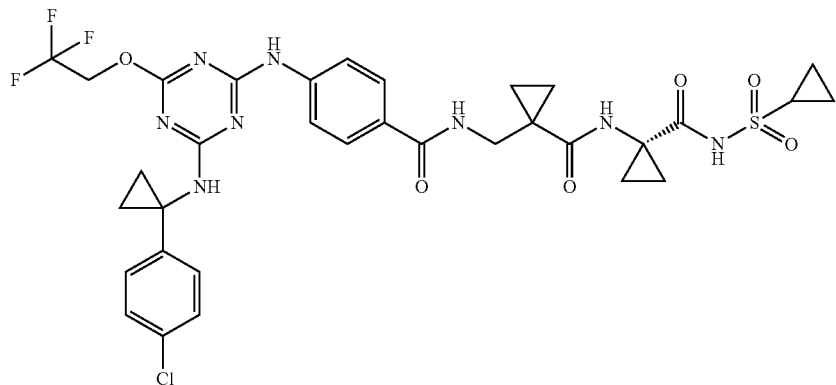

Compound 2067

The Compound 2067 was synthesized following the procedure reported in Scheme 2 of Example 2009. Methyl 1-(aminomethyl)cyclopropanecarboxylate, HCl and 1-amino-N-(cyclopropylsulfonyl)cyclopropanecarboxamide, HCl were used as starting material instead of ethyl 2-aminoacetate and methanesulfonamide in Steps 1 and 3, respectively, to give 17 mg of compound 2067. LC-MS (Condition B), MS m/z 763.22 ($M^++H$).

Example 2068

Preparation of Compound 2068

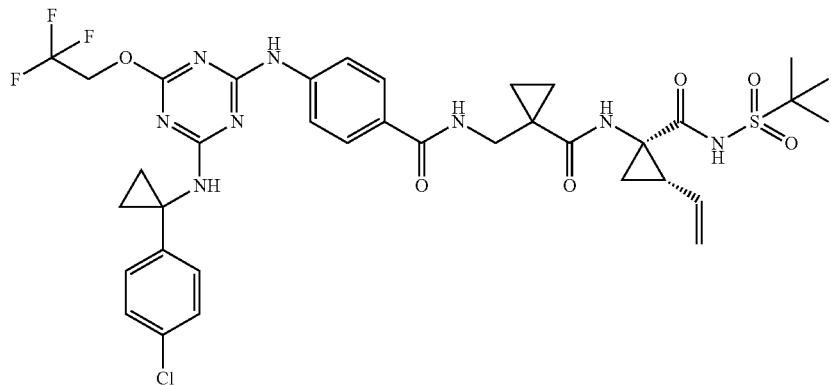

Compound 2068

The Compound 2068 was synthesized following the procedure reported in Scheme 2 of Example 2009. Methyl 1-(aminomethyl)cyclopropanecarboxylate, HCl and (1R, 2S)-1-amino-N-(tert-butylsulfonyl)-2-vinylcyclopropanecarboxamide, HCl were used as starting material instead of ethyl 2-aminoacetate and methanesulfonamide in Steps 1 and 3, respectively, to give 20 mg of compound 2068. LC-MS (Condition B), MS m/z 805.24 ($M^++H$).

Example 2069

Preparation of Compound 2069

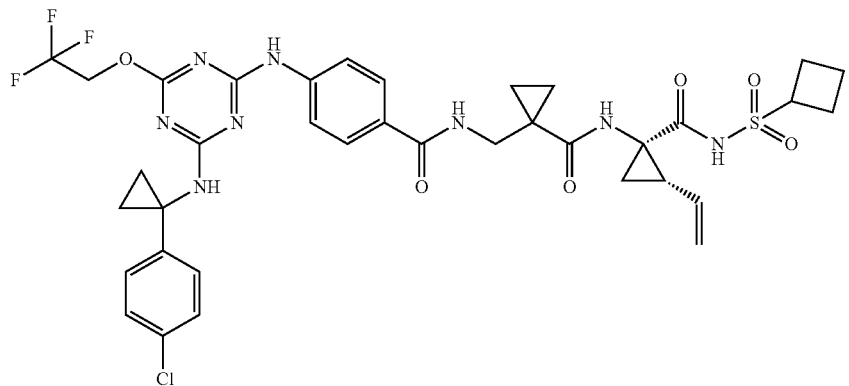

Compound 2069

The Compound 2069 was synthesized following the procedure reported in Scheme 2 of Example 2009. Methyl 1-(aminomethyl)cyclopropanecarboxylate, HCl and (1R, 2S)-1-amino-N-(cyclobutylsulfonyl)-2-vinylcyclopropanecarboxamide, HCl were used as starting material instead of ethyl 2-aminoacetate and methanesulfonamide in Steps 1 and 3, respectively, to give 33 mg of compound 2069. LC-MS (Condition B), MS m/z 803.27 (M$^+$+H).

Example 2070

Preparation of Compound 2070

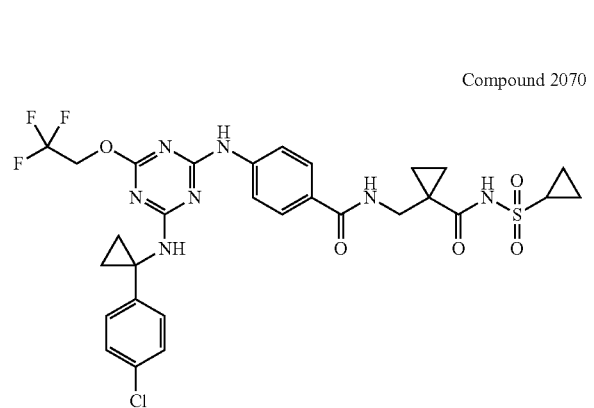 [SMILES: O=C(NCC1(C(=O)NS(=O)(=O)C2CC2)CC1)c1ccc(Nc2nc(NC3(c4ccc(Cl)cc4)CC3)nc(OCC(F)(F)F)n2)cc1]

Compound 2070

The Compound 2070 was synthesized following the procedure reported in Scheme 2 of Example 2009. Methyl 1-(aminomethyl)cyclopropanecarboxylate, HCl and cyclopropanesulfonamide were used as starting material instead of ethyl 2-aminoacetate and methanesulfonamide in Steps 1 and 3, respectively, to give 26 mg of compound 2070. LC-MS (Condition B), MS m/z 680.17 (M$^+$+H).

Example 2071

Preparation of Compound 2071

Compound 2071

The Compound 2071 was synthesized following the procedure reported in Scheme 2 of Example 2009. Methyl 1-(aminomethyl)cyclopropanecarboxylate, HCl and was used as starting material instead of ethyl 2-aminoacetate and Example 2072

Preparation of Compound 2072

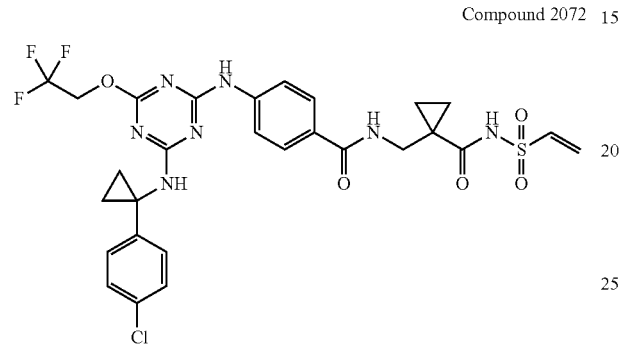

Compound 2072

The Compound 2072 was synthesized following the procedure reported in Scheme 2 of Example 2009. Methyl 1-(aminomethyl)cyclopropanecarboxylate, HCl and ethenesulfonamide were used as starting material instead of ethyl 2-aminoacetate and methanesulfonamide in Steps 1 and 3, respectively, to give 6 mg of compound 2072. LC-MS (Condition B), MS m/z 666.21 (M$^+$+H).

Example 2073

Preparation of Compound 2073

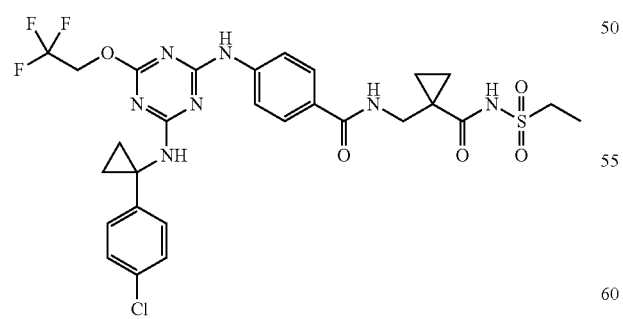

Compound 2073

The Compound 2073 was synthesized following the procedure reported in Scheme 2 of Example 2009. Methyl 1-(aminomethyl)cyclopropanecarboxylate, HCl and ethanesulfonamide were used as starting material instead of ethyl 2-aminoacetate and methanesulfonamide in Steps 1 and 3, respectively, to give 7 mg of compound 2073. LC-MS (Condition B), MS m/z 668.18 (M$^+$+H).

Example 2074

Preparation of Compound 2074

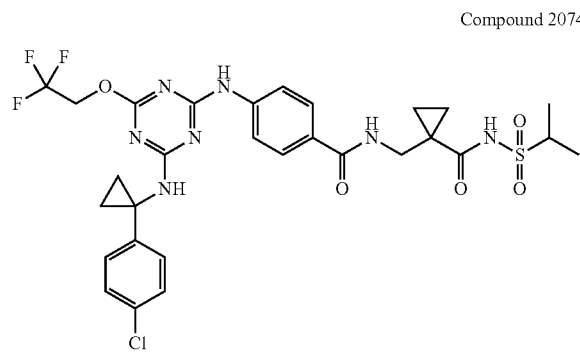

Compound 2074

The Compound 2074 was synthesized following the procedure reported in Scheme 2 of Example 2009. Methyl 1-(aminomethyl)cyclopropanecarboxylate, HCl and propane-2-sulfonamide were used as starting material instead of ethyl 2-aminoacetate and methanesulfonamide in Steps 1 and 3, respectively, to give 20 mg of compound 2074. LC-MS (Condition B), MS m/z 682.20 (M$^+$+H).

Example 2075

Preparation of Compound 2075

Compound 2075

The Compound 2075 was synthesized following the procedure reported in Scheme 2 of Example 2009. Methyl 1-(aminomethyl)cyclopropanecarboxylate, HCl and 2-methylpropane-2-sulfonamide were used as starting material instead of ethyl 2-aminoacetate and methanesulfonamide in

Example 2076

Preparation of Compound 2076

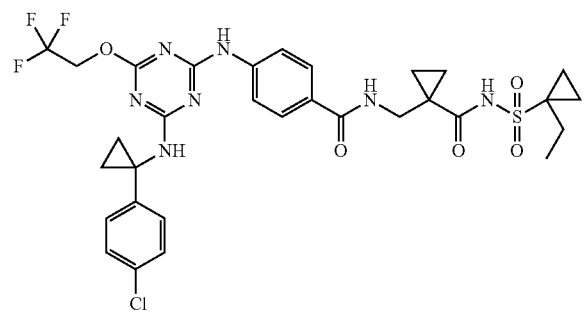

Compound 2076

The Compound 2076 was synthesized following the procedure reported in Scheme 2 of Example 2009. Methyl 1-(aminomethyl)cyclopropanecarboxylate, HCl and 2-1-1-ethylcyclopropane-1-sulfonamide were used as starting material instead of ethyl 2-aminoacetate and methanesulfonamide in Steps 1 and 3, respectively, to give 19 mg of compound 2076. LC-MS (Condition B), MS m/z 708.27 ($M^{+}+H$).

Example 2077

Preparation of Compound 2077

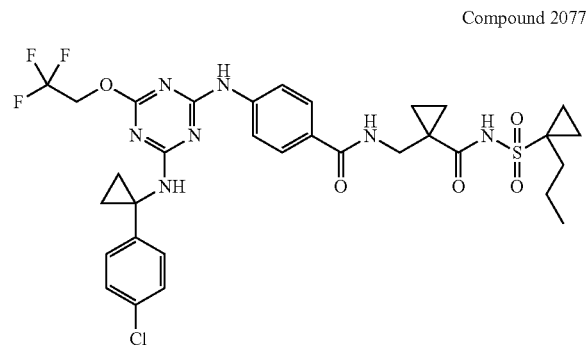 [SMILES: CCCC1(S(=O)(=O)NC(=O)C2(CNC(=O)c3ccc(Nc4nc(NC5(c6ccc(Cl)cc6)CC5)nc(OCC(F)(F)F)n4)cc3)CC2)CC1]

Compound 2077

The Compound 2077 was synthesized following the procedure reported in Scheme 2 of Example 2009. Methyl 1-(aminomethyl)cyclopropanecarboxylate, HCl and 2-1-1-propylcyclopropane-1-sulfonamide were used as starting material instead of ethyl 2-aminoacetate and methanesulfonamide in Steps 1 and 3, respectively, to give 20 mg of compound 2077. LC-MS (Condition B), MS m/z 722.30 ($M^{+}+H$).

Example 2078

Preparation of Compound 2078

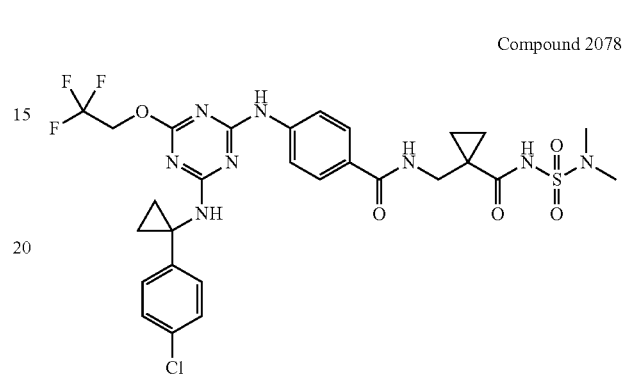

Compound 2078

The Compound 2078 was synthesized following the procedure reported in Scheme 2 of Example 2009. Methyl 1-(aminomethyl)cyclopropanecarboxylate, HCl and N,N-dimethylsulfonamide were used as starting material instead of ethyl 2-aminoacetate and methanesulfonamide in Steps 1 and 3, respectively, to give 18 mg of compound 2078. LC-MS (Condition B), MS m/z 683.25 ($M^{+}+H$).

Example 2079

Preparation of Compound 2079

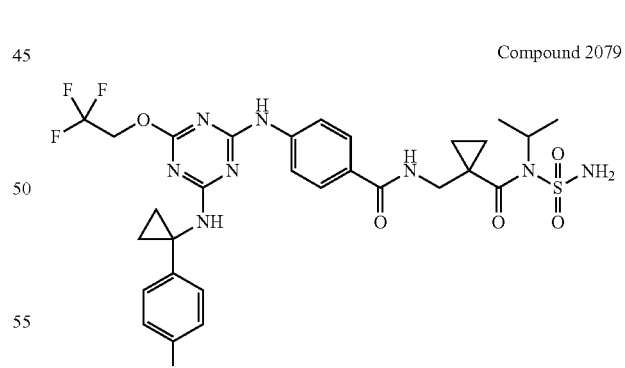

Compound 2079

The Compound 2079 was synthesized following the procedure reported in Scheme 2 of Example 2009. Methyl 1-(aminomethyl)cyclopropanecarboxylate, HCl and tert-butyl N-isopropylsulfamoylcarbamate were used as starting material instead of ethyl 2-aminoacetate and methanesulfonamide in Steps 1 and 3, respectively, to give 8 mg of compound 2079. LC-MS (Condition B), MS m/z 697.28 ($M^{+}+H$).

Example 2080

Preparation of Compound 2080

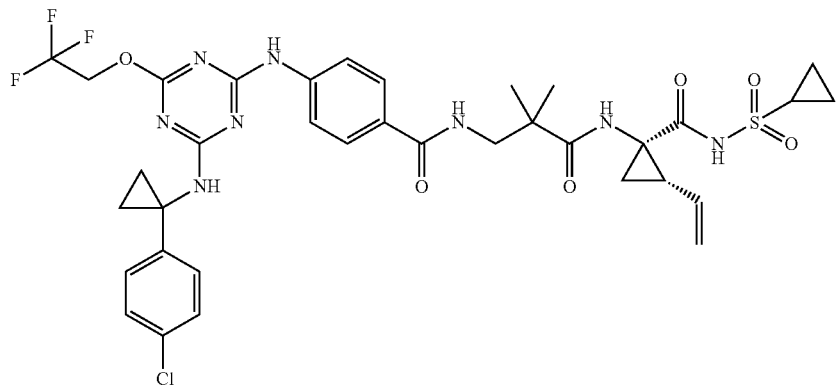

Compound 2080

The Compound 2080 was synthesized following the procedure reported in Scheme 2 of Example 2009. Methyl 3-amino-2,2-dimethylpropanoate, HCl and (1R,2S)-1-amino-N-(cyclopropylsulfonyl)-2-vinylcyclopropanecarboxamide, HCl were used as starting material instead of ethyl 2-aminoacetate and methanesulfonamide in Steps 1 and 3, respectively, to give 20 mg of compound 2080. LC-MS (Condition B), MS m/z 791.27 ($M^+$+H).

Example 2081

Preparation of Compound 2081

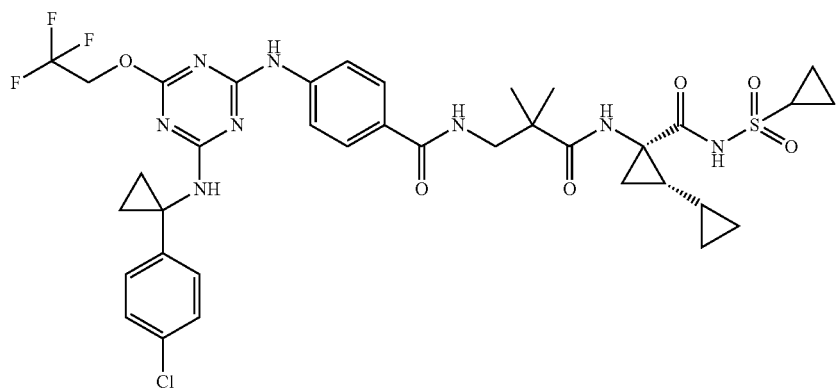

Compound 2081

The Compound 2081 was synthesized following the procedure reported in Scheme 2 of Example 2009. Methyl 3-amino-2,2-dimethylpropanoate, HCl and (1S,2R)-2-amino-N-(cyclopropylsulfonyl)bi(cyclopropane)-2-carboxamide, HCl were used as starting material instead of ethyl 2-aminoacetate and methanesulfonamide in Steps 1 and 3, respectively, to give 21 mg of compound 2081. LC-MS (Condition B), MS m/z 805.26 ($M^+$+H).

Example 2082

Preparation of Compound 2082

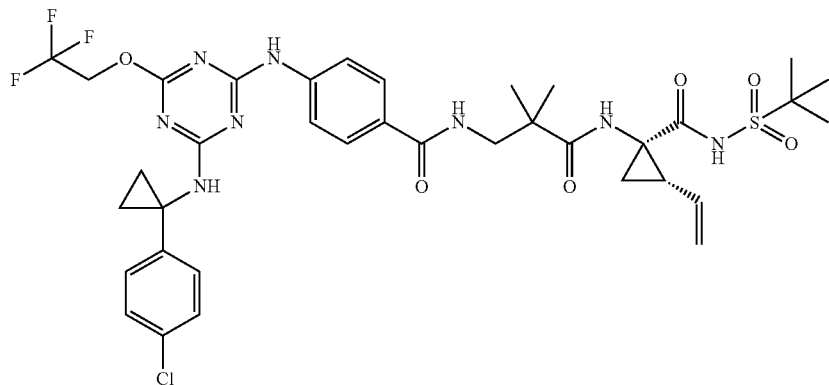

Compound 2082

The Compound 2082 was synthesized following the procedure reported in Scheme 2 of Example 2009. Methyl 3-amino-2,2-dimethylpropanoate, HCl and (1R,2S)-1-amino-N-(tert-butylsulfonyl)-2-vinylcyclopropanecarboxamide, HCl were used as starting material instead of ethyl 2-aminoacetate and methanesulfonamide in Steps 1 and 3, respectively, to give 12 mg of compound 2082. LC-MS (Condition B), MS m/z 807.31 ($M^+$+H).

Example 2083

Preparation of Compound 2083

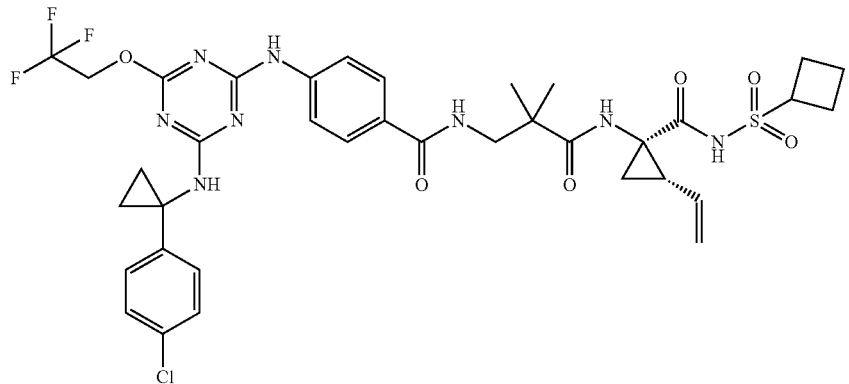

Compound 2083

The Compound 2083 was synthesized following the procedure reported in Scheme 2 of Example 2009. Methyl 3-amino-2,2-dimethylpropanoate, HCl and (1R,2S)-1-amino-N-(cyclobutylsulfonyl)-2-vinylcyclopropanecarboxamide, HCl were used as starting material instead of ethyl 2-aminoacetate and methanesulfonamide in Steps 1 and 3, Example 2084

Preparation of Compound 2084

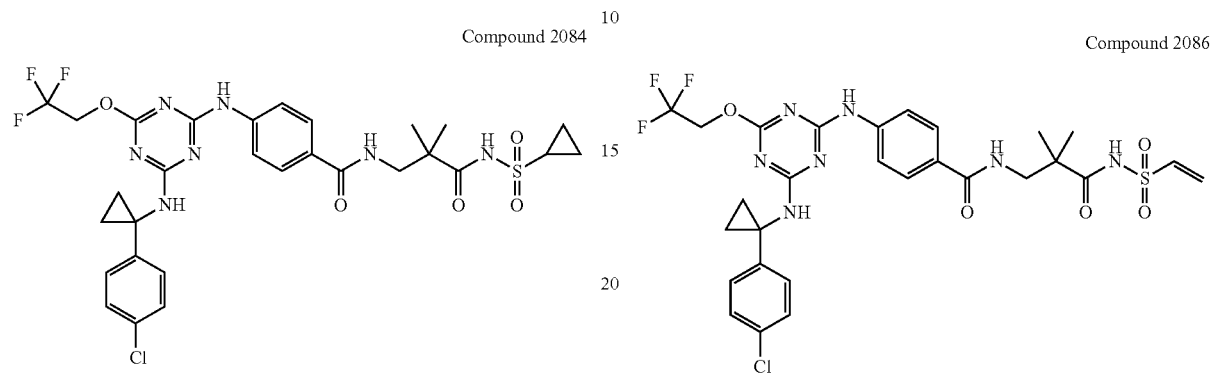
Compound 2084

The Compound 2084 was synthesized following the procedure reported in Scheme 2 of Example 2009. Methyl 3-amino-2,2-dimethylpropanoate, HCl and cyclopropanesulfonamide were used as starting material instead of ethyl 2-aminoacetate and methanesulfonamide in Steps 1 and 3, respectively, to give 20 mg of compound 2084. LC-MS (Condition B), MS m/z 682.20 (M$^+$+H).

Example 2085

Preparation of Compound 2085

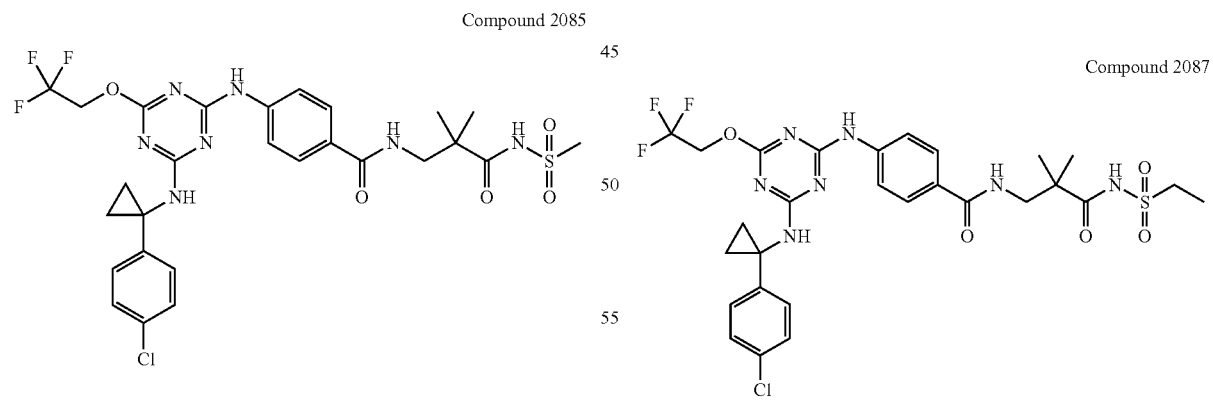
Compound 2085

The Compound 2085 was synthesized following the procedure reported in Scheme 2 of Example 2009. Methyl 3-amino-2,2-dimethylpropanoate, HCl and was used as starting material instead of ethyl 2-aminoacetate and methanesulfonamide in Step 1 to give 19 mg of compound 2085. LC-MS (Condition B), MS m/z 656.17 (M$^+$+H).

Example 2086

Preparation of Compound 2086

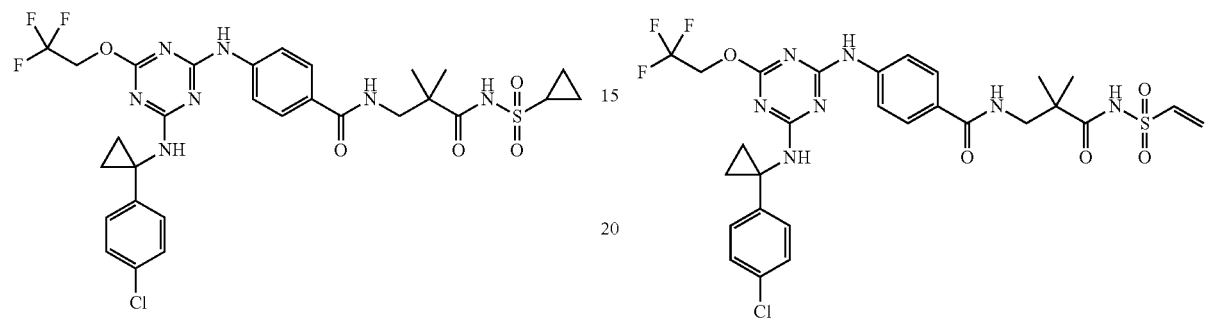
Compound 2086

The Compound 2086 was synthesized following the procedure reported in Scheme 2 of Example 2009. Methyl 3-amino-2,2-dimethylpropanoate, HCl and ethenesulfonamide were used as starting material instead of ethyl 2-aminoacetate and methanesulfonamide in Steps 1 and 3, respectively, to give 18 mg of compound 2086. LC-MS (Condition B), MS m/z 668.18 (M$^+$+H).

Example 2087

Preparation of Compound 2087

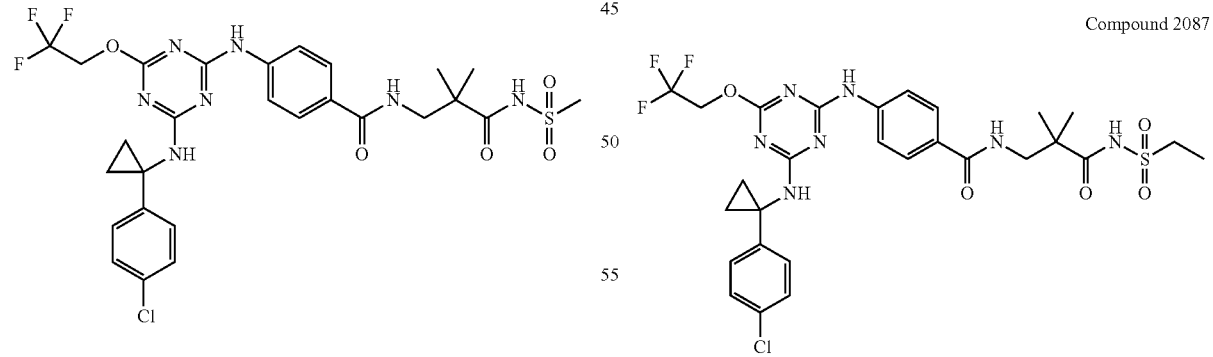
Compound 2087

The Compound 2087 was synthesized following the procedure reported in Scheme 2 of Example 2009. Methyl 3-amino-2,2-dimethylpropanoate, HCl and ethanesulfonamide were used as starting material instead of ethyl 2-aminoacetate and methanesulfonamide in Steps 1 and 3, respectively, to give 19 mg of compound 2087. LC-MS (Condition B), MS m/z 670.19 (M⁺+H).

Example 2088

Preparation of Compound 2088

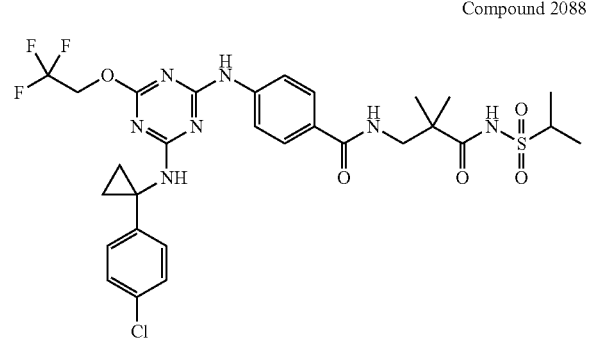 [SMILES: CC(C)S(=O)(=O)NC(=O)C(C)(C)CNC(=O)c1ccc(Nc2nc(NC3(c4ccc(Cl)cc4)CC3)nc(OCC(F)(F)F)n2)cc1]

Compound 2088

The Compound 2088 was synthesized following the procedure reported in Scheme 2 of Example 2009. Methyl 3-amino-2,2-dimethylpropanoate, HCl and propane-2-sulfonamide were used as starting material instead of ethyl 2-aminoacetate and methanesulfonamide in Steps 1 and 3, respectively, to give 18 mg of compound 2088. LC-MS (Condition B), MS m/z 684.21 (M⁺+H).

Example 2089

Preparation of Compound 2089

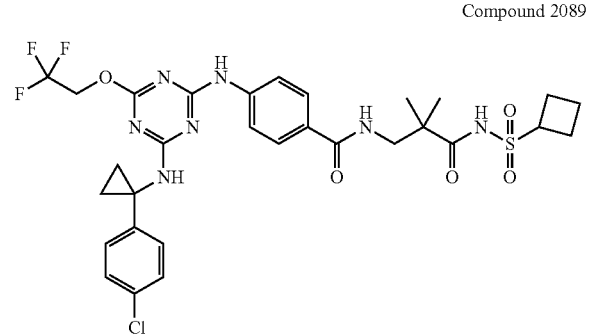 [SMILES: CC(C)(CNC(=O)c1ccc(Nc2nc(NC3(c4ccc(Cl)cc4)CC3)nc(OCC(F)(F)F)n2)cc1)C(=O)NS(=O)(=O)C1CCC1]

Compound 2089

The Compound 2089 was synthesized following the procedure reported in Scheme 2 of Example 2009. Methyl 3-amino-2,2-dimethylpropanoate, HCl and cyclobutanesulfonamide were used as starting material instead of ethyl 2-aminoacetate and methanesulfonamide in Steps 1 and 3, respectively, to give 18 mg of compound 2089. LC-MS (Condition B), MS m/z 696.22 (M⁺+H).

Example 2090

Preparation of Compound 2090

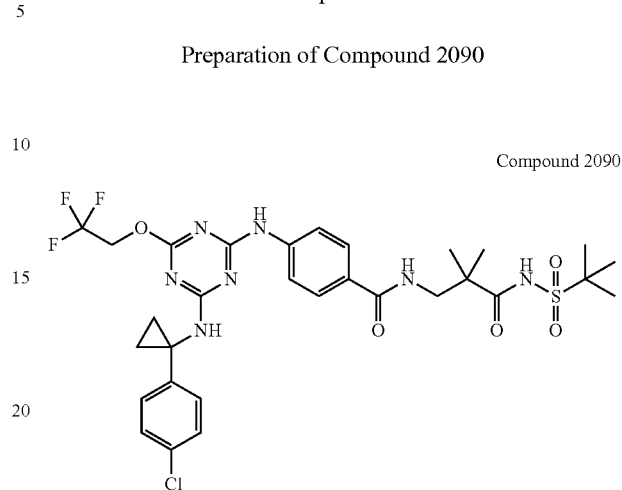

Compound 2090

The Compound 2090 was synthesized following the procedure reported in Scheme 2 of Example 2009. Methyl 3-amino-2,2-dimethylpropanoate, HCl and 2-methylpropane-2-sulfonamide were used as starting material instead of ethyl 2-aminoacetate and methanesulfonamide in Steps 1 and 3, respectively, to give 7 mg of compound 2090. LC-MS (Condition B), MS m/z 698.25 (M⁺+H).

Example 2091

Preparation of Compound 2091

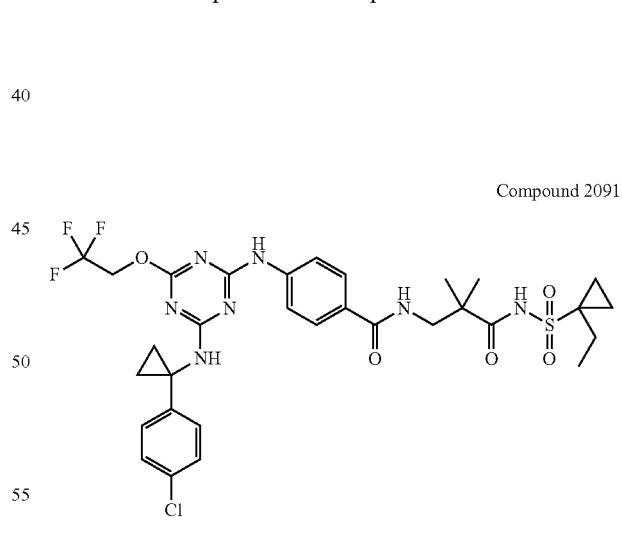

Compound 2091

The Compound 2091 was synthesized following the procedure reported in Scheme 2 of Example 2009. Methyl 3-amino-2,2-dimethylpropanoate, HCl and 2-1-ethylcyclopropane-1-sulfonamide were used as starting material instead of ethyl 2-aminoacetate and methanesulfonamide in Steps 1 and 3, respectively, to give 10 mg of compound 2091. LC-MS (Condition B), MS m/z 710.25 (M⁺+H).

Example 2092

Preparation of Compound 2092

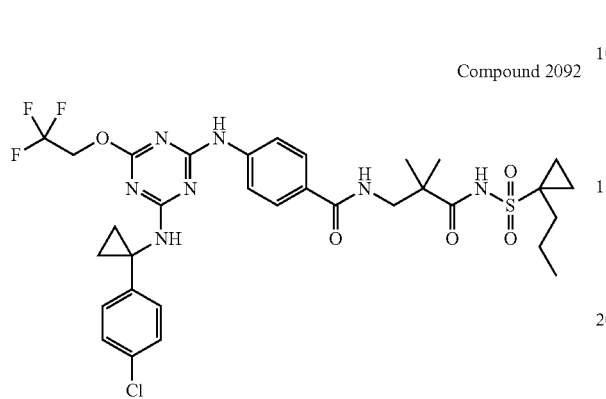

Compound 2092

The Compound 2092 was synthesized following the procedure reported in Scheme 2 of Example 2009. Methyl 3-amino-2,2-dimethylpropanoate, HCl and 2-1-1-propylcyclopropane-1-sulfonamide were used as starting material instead of ethyl 2-aminoacetate and methanesulfonamide in Steps 1 and 3, respectively, to give 8 mg of compound 2092. LC-MS (Condition B), MS m/z 724.27 (M⁺+H).

Example 2093

Preparation of Compound 2093

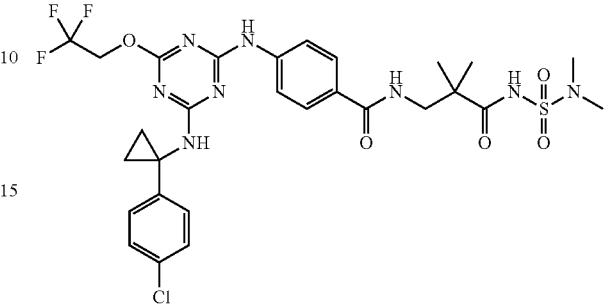

Compound 2093

The Compound 2093 was synthesized following the procedure reported in Scheme 2 of Example 2009. Methyl 3-amino-2,2-dimethylpropanoate, HCl and N,N-dimethylsulfonamide were used as starting material instead of ethyl 2-aminoacetate and methanesulfonamide in Steps 1 and 3, respectively, to give 19 mg of compound 2093. LC-MS (Condition B), MS m/z 685.21 (M⁺+H).

Example 2094

Preparation of Compound 2094

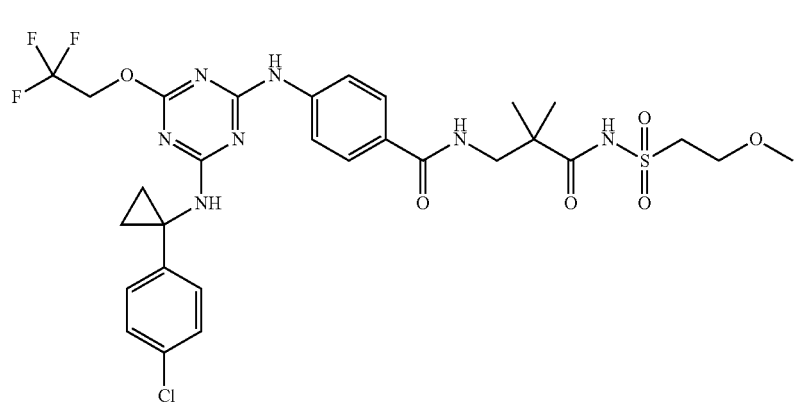

Compound 2094

The Compound 2094 was synthesized following the procedure reported in Scheme 2 of Example 2009. Methyl 3-amino-2,2-dimethylpropanoate, HCl and t2-methoxyethanesulfonamide were used as starting material instead of ethyl 2-aminoacetate and methanesulfonamide in Steps 1 and 3, respectively, to give 22 mg of compound 2094. LC-MS (Condition B), MS m/z 697.28 (M⁺+H).

Example 2095

Preparation of Compound 2095

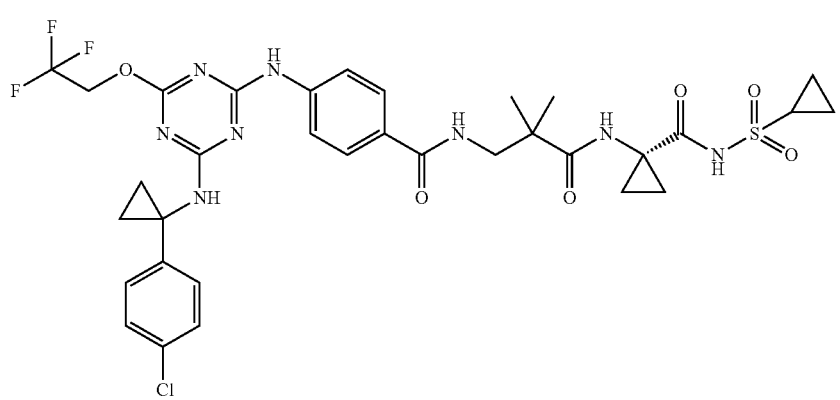

Compound 2095

The Compound 2095 was synthesized following the procedure reported in Scheme 2 of Example 2009. Methyl 3-amino-2,2-dimethylpropanoate, HCl and 1-amino-N-(cyclopropylsulfonyl)cyclopropanecarboxamide, HCl were used as starting material instead of ethyl 2-aminoacetate and methanesulfonamide in Steps 1 and 3, respectively, to give 24 mg of compound 2095. LC-MS (Condition B), MS m/z 76.23 ($M^+ + H$).

Example 2096

Preparation of Compound 2096

Compound 2096

The Compound 2096 was synthesized following the procedure reported in Scheme 2 of Example 2009 with following new conditions:

Modified Step 1:

To a solution of 4-(4-(1-(4-chlorophenyl)cyclopropylamino)-6-(2,2,2-trifluoroethoxy)-1,3,5-triazin-2-ylamino)benzoic acid (50 mg) in DMF (2 mL) was added O-(benzotriazol-1-yl-N,N,N',N'-tetramethyluronium tetrafluoroborate (23.82 mg) and (S)-methyl 2-amino-3-(tert-butoxycarbonylamino)propanoate hydrochloride (18.90 mg) and iPr2NEt (0.052 ml). After stirring at rt for 4 h, the mixture was purified by preparative HPLC to give (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate.

Modified Step 2:

A suspension of (S)-methyl 3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoate (25 mg) and K2CO3 (25.4 mg) in acetone and water (1:1, 4 mL) was stirred at room temperature for 16 hours. The mixture was acidified to pH1. Solvents were removed under vacuum and the residue was purified by preparative HPLC to give (S)-3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoic acid (15.6 mg) and (S)-3-amino-2-(4-(4-(1-(4-chlorophenyl)cyclopropylamino)-6-(2,2,2-trifluoroethoxy)-1,3,5-triazin-2-ylamino)benzamido)propanoic acid (3.9 mg).

Modified Step 3:

To a solution of (S)-3-(tert-butoxycarbonylamino)-2-(4-(4-(1-(4-chlorophenyl)cyclopropylamino)-6-(2,2,2-trifluoroethoxy)-1,3,5-triazin-2-ylamino)benzamido)propanoic acid (10 mg) in CH2CL2 (5 mL) was added cyclopropanesulfonamide (3.64 mg), EDC (4.32 mg) and DMAP (5.50 mg). The resulting mixture was stirred at room temperature for 16 hours. Solvents were removed under vacuum and the residue was purified by preparative HPLC to give 1 mg of compound 2096. LC-MS (Condition D), MS m/z 769.3 (M⁺+H).

Example 3001

Preparation of Compound 3001

Compound 3001

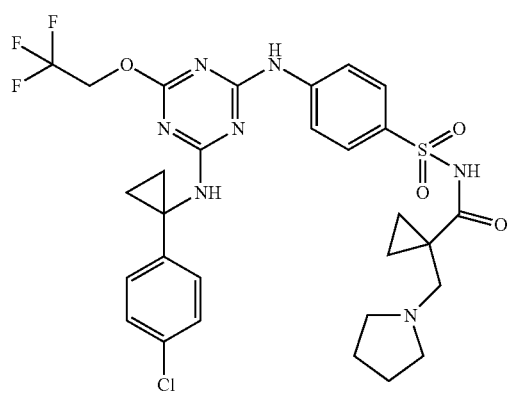

Scheme 1

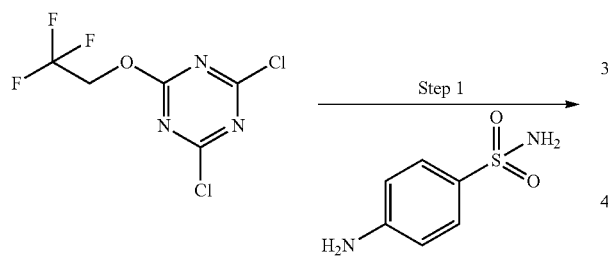

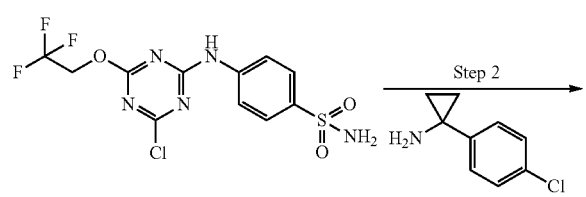

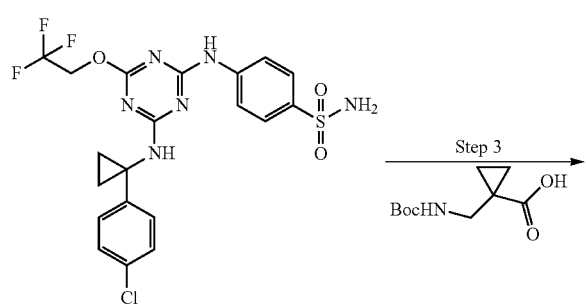

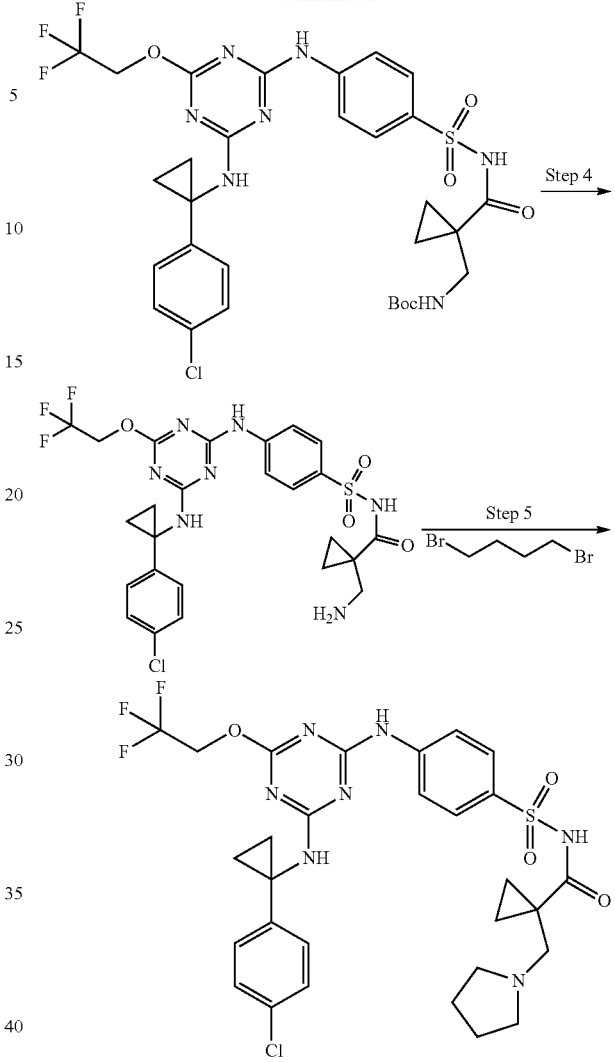

Step 1:
To a suspension of 2,4-dichloro-6-(2,2,2-trifluoroethoxy)-1,3,5-triazine (2 g, 8.06 mmol) in THF (25 mL) was added sulfanilamide (1.39 g, 8.06 mmol) and iPr₂NEt (4.23 mL, 24.2 mmol). The mixture was stirred at room temperature for 16 hours. The solvent was removed under vacuum. The crude product 4-(4-chloro-6-(2,2,2-trifluoroethoxy)-1,3,5-triazin-2-ylamino)benzenesulfonamide was used directly in the next step without further purification. LC-MS (Condition A), MS m/z 383.9 (M⁺+H).

Step 2:
To a suspension of 4-(4-chloro-6-(2,2,2-trifluoroethoxy)-1,3,5-triazin-2-ylamino)benzenesulfonamide from step 1 (1 g, 2.61 mmol) in THF (20 mL) was added 1-(4-chlorophenyl)cyclopropanamine, HCl (0.53 g, 2.61 mmol) and iPr₂NEt (1.35 mL, 10.4 mmol). The mixture was heated at reflux condition for 16 hours. The solvent was removed under vacuum. The crude product 4-(4-(1-(4-chlorophenyl)cyclopropylamino)-6-(2,2,2-trifluoroethoxy)-1,3,5-triazin-2-ylamino)benzenesulfonamide was used directly in the next step without further purification. LC-MS (Condition A), MS m/z 514.9 (M⁺+H).

Step 3:
To a solution of 4-(4-(1-(4-chlorophenyl)cyclopropylamino)-6-(2,2,2-trifluoroethoxy)-1,3,5-triazin-2-ylamino)

benzenesulfonamide (1 g, 1.94 mmol) in DCM (10 mL) solution were added PyBOP (1.21 g, 2.33 mmol), 1-((tert-butoxycarbonylamino)methyl)cyclopropanecarboxylic acid (0.46 g, 2.14 mmol) and DIEA (1.36 mL, 7.77 mmol). The mixture was stirred at room temperature for 16 hs. All solvents were removed under vacuum and the residue was purified by silica gel column (MeOH/hexane: 5%) to give tert-butyl (1-(4-(4-(1-(4-chlorophenyl)cyclopropylamino)-6-(2,2,2-trifluoroethoxy)-1,3,5-triazin-2-ylamino)phenylsulfonylcarbamoyl)cyclopropyl)methylcarbamate (1.38 g, 100%) as a brown solid. LC-MS (Condition A), MS m/z 712.0 (M$^+$+H).

Step 4:

tert-butyl (1-(4-(4-(1-(4-chlorophenyl)cyclopropylamino)-6-(2,2,2-trifluoroethoxy)-1,3,5-triazin-2-ylamino)phenylsulfonylcarbamoyl)cyclopropyl)methylcarbamate (1.38 g, 1.94 mmol) in 4 M HCl dioxane solution was stirred at r.t. for 3 hours. All solvents were removed under vacuum to give product. The crude product was used directly in the next step. LC-MS, MS m/z 612.0 (M$^+$+H).

Step 5:

To a solution of 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol) in Acetonitrile (2 mL) was added 1,4-dibromobutane (10.6 mg, 0.05 mmol) and potassium carbonate (34 mg, 0.25 mmol). The mixture was heated to 65° C. for 16 h. After cooling to r.t, the solvent was evaporated and the residue was purified by preparative HPLC to afford 3.7 mg (11%) white solid as desired product. $^1$H NMR (400 MHz, MeOD) δ ppm 1.15 (m, 2H), 1.39 (m, 6H), 1.86 (m, 2H), 2.03 (m, 4H), 3.14 (m, 2H), 3.31 (m, 2H), 4.88 (m, 2H), 7.27 (m, 4H), 7.73 (m, 3H), 7.93 (m, 1H); LC-MS (Condition A), MS m/z 666.0 (M$^+$+H).

Example 3002

Preparation of Compound 3002

Compound 3002

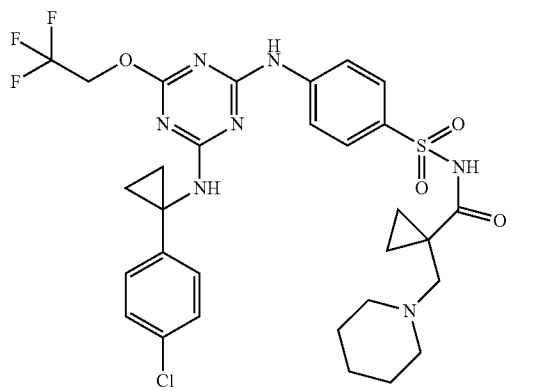

The compound 3002 was synthesized following the procedure reported in Scheme 1 of Example 3001. 1,5-Diiodopentane was used as starting material in step 5 instead of 1,4-dibromobutane. LC-MS (Condition A), MS m/z 680.0 (M$^+$+H).

Example 3003

Preparation of Compound 3003

Compound 3003

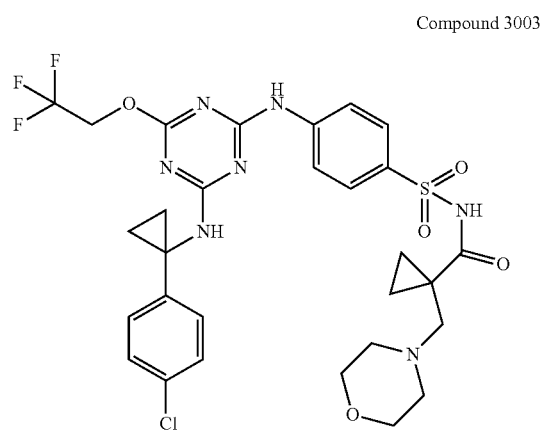 [SMILES: O=C(NS(=O)(=O)c1ccc(Nc2nc(NC3(c4ccc(Cl)cc4)CC3)nc(OCC(F)(F)F)n2)cc1)C1(CN2CCCCC2)CC1]

The compound 3003 was synthesized following the procedure reported in Scheme 5 of Example 3001. 1-Iodo-2-(2-iodoethoxy)ethane was used as starting material in step 5 instead of 1,4-dibromobutane. $^1$H NMR (400 MHz, MeOD) δ ppm 1.10-1.20 (m, 2H), 1.33-1.40 (m, 4H), 1.43-1.47 (m, 2H), 3.15 (d, J=3.76 Hz, 2H), 3.22-3.33 (m, 2H), 3.34-3.36 (m, 2H), 3.85 (m, 4H), 4.88 (m, 2H), 7.22-7.31 (m, 4H), 7.71 (t, J=9.54 Hz, 3H), 7.90-7.98 (m, 1H); LC-MS (Condition A), MS m/z 681.9 (M$^+$+H).

Example 3004

Preparation of Compound 3004

Compound 3004

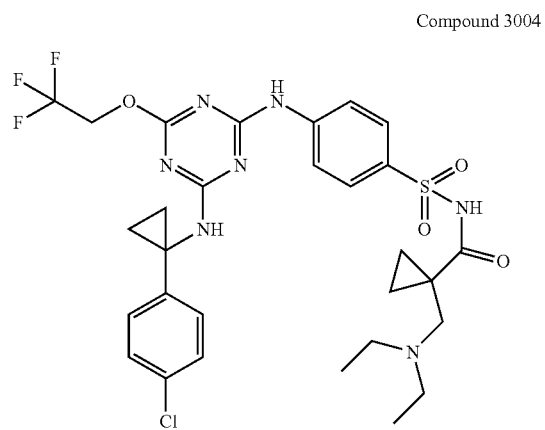 [SMILES: CCN(CC)CC1(C(=O)NS(=O)(=O)c2ccc(Nc3nc(NC4(c5ccc(Cl)cc5)CC4)nc(OCC(F)(F)F)n3)cc2)CC1]

The compound 3004 was prepared by modification of Step 5 of Example 3001. 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol), acetaldehyde (10.8 mg, 0.25 mmol), AcOH (2.81 nl, 0.05 mmol), were dissolved in DCM (2 mL) and sodium triacetoxyborohydride (52 mg, 0.25 mmol) was added to the solution. The reaction was stirred for 4 h. The solvent was removed under vacuum and the crude product was purified by rev. phase HPLC to give compound 3004 (5.6 mg, 16%) as a white solid. LC-MS (Condition A), MS m/z 668.0 (M$^+$+H).

Example 3005

Preparation of Compounds 3005

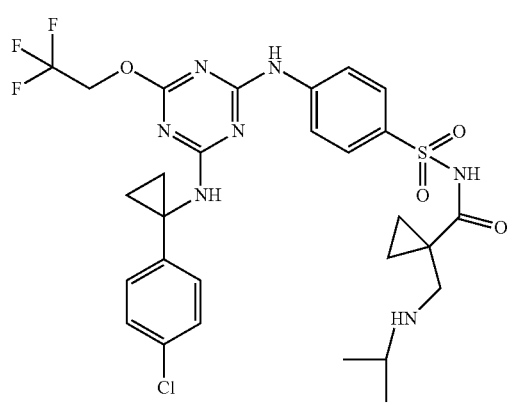

Compound 3005

The compound 3005 was prepared by modification of Step 5 of Example 3001. 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol), propan-2-one (3.4 mg, 0.06 mmol), titanium(IV) isopropoxide (30 µl, 0.10 mmol), were dissolved in DCM (2 mL). The reaction was stirred for 16 h. Sodium triacetoxyborohydride (21 mg, 0.10 mmol) was added to the solution. The reaction was stirred for 4 h. The solvent was removed under vacuum and the crude product was purified by rev. phase HPLC to give compound 3005 (4.1 mg, 12.2%) as a white solid. $^1$H NMR (400 MHz, MeOD) δ ppm 0.90 (m, 2H), 1.31-1.44 (m, 10H), 1.87 (m, 1H), 3.17 (m, 4H), 4.92 (m, 2H), 7.29 (m 4H), 7.75 (m 3H), 7.95 (m 1H). LC-MS (Condition A), MS m/z 654.0 (M$^+$+H).

Example 3006

Preparation of Compound 3006

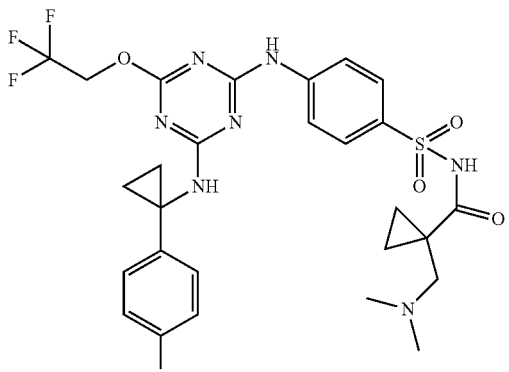

Compound 3006

The compound 3006 was prepared by modification of Step 5 of Example 3001. 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol), formaldehyde (7.4 mg, 0.25 mmol), Et3N (14 µl, 0.25 mmol), were dissolved in DCM (2 mL) and sodium triacetoxyborohydride (52 mg, 0.25 mmol) was added to the solution. The reaction was stirred for 4 h. The solvent was removed under vacuum and the crude product was purified by rev. phase HPLC to give compound 3006 (2.0 mg, 6%) as a white solid. LC-MS (Condition A), MS m/z 640.0 (M$^+$+H).

Example 3007

Preparation of Compound 3007

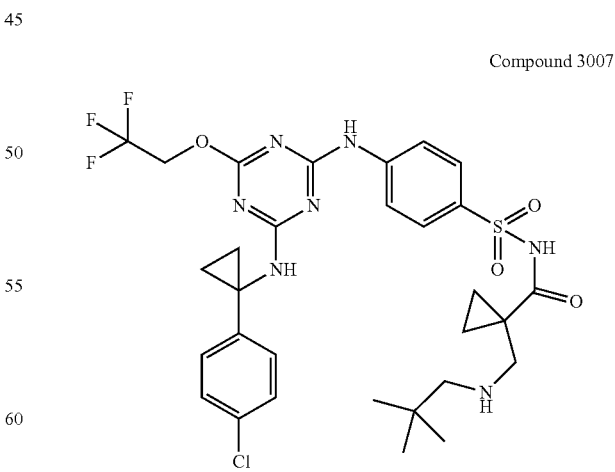

Compound 3007

The compound 3007 was prepared by modification of Step 5 of Example 3001. 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol), pivalaldehyde (4.2 mg, 0.05 mmol), AcOH (2.81 µl, 0.05 mmol), were dissolved in DCM (2 mL) and sodium triacetoxyborohydride (52 mg, 0.25 mmol) was added to the solution. The reaction was stirred for 4 h. The solvent was removed under vacuum and the crude product was purified by rev. phase HPLC to give compound 3007 (2.3 mg, 6.5%) as a white solid. LC-MS (Condition A), MS m/z 682.0 (M⁺+H).

HPLC to give compound 3008 (3.7 mg, 10%) as a white solid. LC-MS (Condition A), MS m/z 737.0 (M⁺+H).

Example 3009

Preparation of Compound 3009

Compound 3009

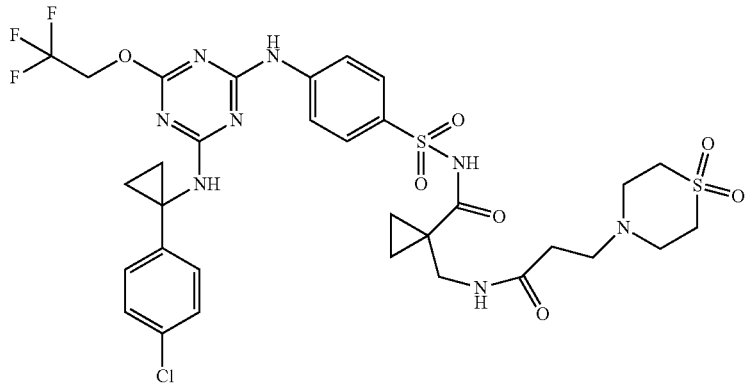

Example 3008

Preparation of Compound 3008

Compound 3008

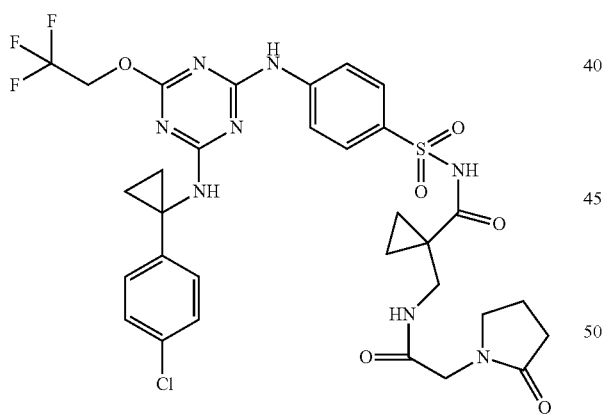

The compound 3008 was prepared by modification of Step 5 of Example 3001. To a solution of 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol) in DCM (5 mL) solution were added ethyl 2-(2-oxopyrrolidin-1-yl)acetic acid (14 mg, 0.10 mmol), HATU (28 mg, 0.07 mmol) and iPr₂NEt (43 ul, 0.25 mmol). The mixture was stirred at room temperature for 16 hs. The solvent was removed under vacuum and the crude product was purified by rev. phase The Compound 3009 was prepared by modification of Step 5 of Example 3001. To a solution of 1-(aminomethyl)-N-(4-(4-(1-(4-chlorophenyl)cyclopropylamino)-6-(2,2,2-trifluoroethoxy)-1,3,5-triazin-2-ylamino)phenylsulfonyl)cyclopropanecarboxamide, HCl (30 mg, 0.05 mmol) in DCM (5 mL) solution were added 1-dioxide-4-thiomorpholinepropanolic acid (10.2 mg, 0.05 mmol), HATU (28 mg, 0.07 mmol) and iPr₂NEt (43 ul, 0.25 mmol). The mixture was stirred at room temperature for 16 hs. The solvent was removed under vacuum and the crude product was purified by rev. phase HPLC to give Compound 3009 (1.8 mg, 4.4%) as a white solid. LC-MS (Condition A), MS m/z 801.0 (M⁺+H).

Example 4000

Preparation of Compounds 4000

Compound 4000

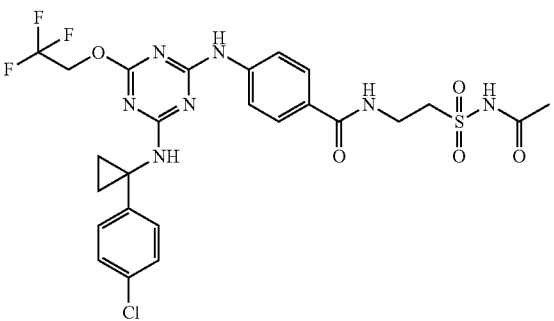

Scheme 2

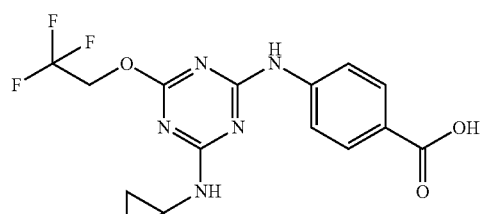

Step 1

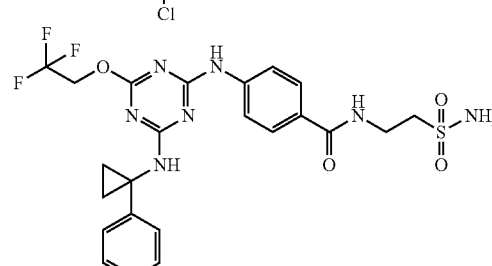

Step 2

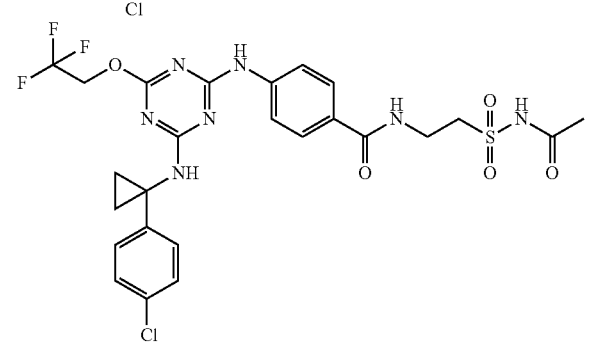

Step 1:
4-(4-(1-(4-chlorophenyl)cyclopropylamino)-6-(2,2,2-trifluoroethoxy)-1,3,5-triazin-2-ylamino)benzoic acid (500 mg, 1.042 mmol), 2-aminoethanesulfonamide (142 mg, 1.146 mmol), HATU (594 mg, 1.563 mmol), and Hunig's Base (0.910 mL, 5.21 mmol) were stirred in DCM (Volume: 5 mL) for 16 h. The solvent was removed and the crude material was purified by silica gel chromatography using EtOAc to give 4-(4-(1-(4-chlorophenyl)cyclopropylamino)-6-(2,2,2-trifluoroethoxy)-1,3,5-triazin-2-ylamino)-N-(2-sulfamoylethyl)benzamide (150 mg). 1H NMR (400 MHz, MeOD) δ ppm 1.31-1.42 (m, 4H), 3.34-3.40 (m, 2H), 3.79-3.89 (m, 2H), 4.86-4.92 (m, 2H), 7.20-7.33 (m, 4H), 7.58-7.71 (m, 3H), 7.76-7.89 (m, 1H); LC-MS (Condition A), MS m/z (M$^+$+H) 585.9.

Step 2:
4-(4-(1-(4-chlorophenyl)cyclopropylamino)-6-(2,2,2-trifluoroethoxy)-1,3,5-triazin-2-ylamino)-N-(2-sulfamoylethyl)benzamide (20 mg, 0.034 mmol), acetic acid (3.07 mg, 0.051 mmol), PyBOP (26.6 mg, 0.051 mmol), and Hunig's Base (0.030 mL, 0.171 mmol) were stirred in DCM (Volume: 3 mL) for 16 h. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier to give compound 4000 (15 mg). 1H NMR (400 MHz, DMSO-d$_6$) δ ppm 1.24-1.41 (m, 4H), 1.98 (s, 3H), 3.49-3.75 (m, 4H), 4.99 (q, J=9.0 Hz, 2H), 7.14-7.42 (m, 4H), 7.55-7.73 (m, 3H), 7.73-7.92 (m, 1H), 8.48 (br. s., 1H), 8.79 (br. s., 1H), 9.96 (br. s., 1H), 11.73 (s, 1H); LC-MS (Condition A), MS m/z (M$^+$+H) 627.9.

Example 401

Preparation of Compound 4001

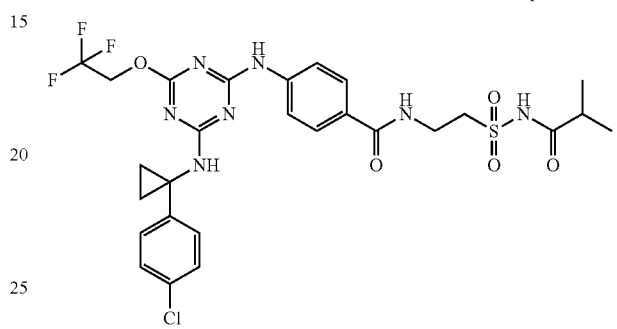

Compound 4001

Compound 4001 was prepared by the same method as Compound 4000 with the following modifications: isobutyric acid instead of acetic acid in Step 3 was used as a starting material to give compound 4001 (14 mg). 1H NMR (400 MHz, DMSO-d$_6$) δ ppm 1.03 (d, J=6.8 Hz, 6H), 1.26-1.42 (m, 4H), 2.44-2.57 (m, 1H), 3.63 (s, 4H), 4.99 (q, J=9.0 Hz, 2H), 7.16-7.41 (m, 4H), 7.59-7.93 (m, 4H), 8.51 (br. s., 1H), 8.79 (br. s., 1H), 9.95 (br. s., 1H), 11.68 (s, 1H); LC-MS (Condition A), MS m/z (M$^+$+H) 656.0.

Example 4002

Preparation of Compounds 4002

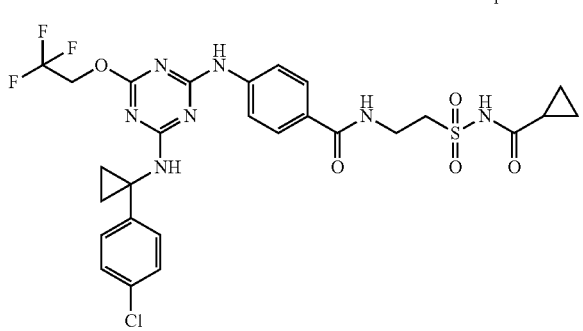

Compound 4002

Compound 4002 was prepared by the same method as Compound 4000 with the following modifications: cyclopropanecarboxylic acid instead of acetic acid in Step 3 was used as a starting material to give compound 4002 (12 mg). 1H NMR (400 MHz, MeOD) δ ppm 0.78-1.02 (m, 4H), 1.27-1.46 (m, 4H), 1.55-1.69 (m, 1H), 3.67-3.77 (m, 2H), 3.80-3.90 (m, 2H), 4.86-4.95 (m, 2H), 7.19-7.36 (m, 4H), 7.58-7.73 (m, 3H), 7.78-7.92 (m, 1H); LC-MS (Condition A), MS m/z (M$^+$+H) 654.0.

Example 4003

Preparation of Compounds 4003

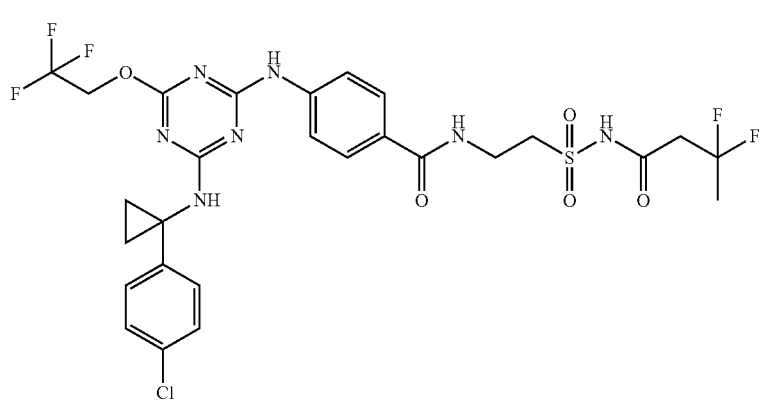

Compound 4003

Compound 4003 was prepared by the same method as compound 4000 with the following modifications: 3,3,3-trifluoropropanoic acid instead of acetic acid in Step 3 was used as a starting material to give compound 4003 (12 mg). 1H NMR (400 MHz, DMSO-$d_6$) δ ppm 1.18-1.45 (m, 4H), 3.56 (q, J=10.8 Hz, 2H), 3.62-3.75 (m, 4H), 4.99 (q, J=9.2 Hz, 2H), 7.14-7.43 (m, 4H), 7.56-7.93 (m, 4H), 8.44-8.62 (m, 1H), 8.80 (br. s., 1H), 9.96 (br. s., 1H), 12.23 (br. s., 1H); LC-MS (Condition A), MS m/z (M$^+$+H) 696.0.

Example 4004

Preparation of Compound 4004

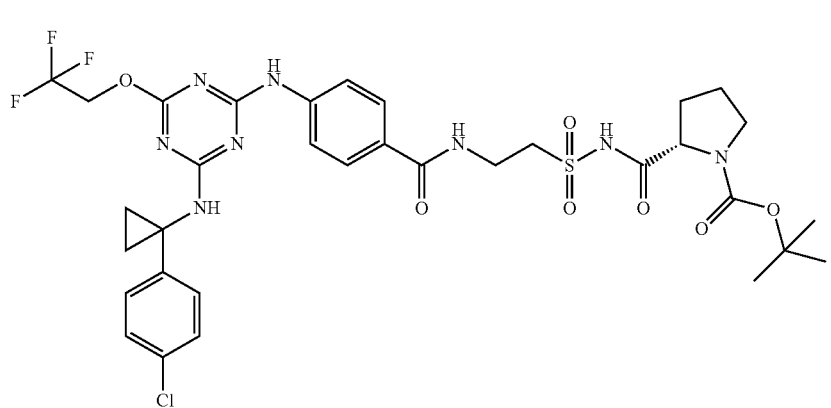

Compound 4004

Compound 4004 was prepared by the same method as Compound 4000 with the following modifications: (S)-1-(tert-butoxycarbonyl)pyrrolidine-2-carboxylic acid instead of acetic acid in Step 3 was used as a starting material. After HPLC, the product fractions were diluted with EtOAc and washed with water 2×, followed by brine. The organic layer was collected, dried over sodium sulfate, and concentrated under vacuum to give compound 4004 (14 mg). 1H NMR (400 MHz, DMSO-$d_6$) δ ppm 1.22-1.46 (m, 13H), 1.69-1.96 (m, 3H), 2.07-2.22 (m, 1H), 3.23-3.43 (m, 2H), 3.55-3.75 (m, 4H), 4.14 (dd, J=8.8, 4.5 Hz, 1H), 4.99 (q, J=9.0 Hz, 2H), 7.15-7.41 (m, 4H), 7.59-7.93 (m, 4H), 8.42-8.64 (m, 1H), 8.79 (br. s., 1H), 9.95 (br. s., 1H), 11.99 (s, 1H); LC-MS (Condition A), MS m/z (M$^+$+H) 783.0.

Example 4005

Preparation of Compounds 4005

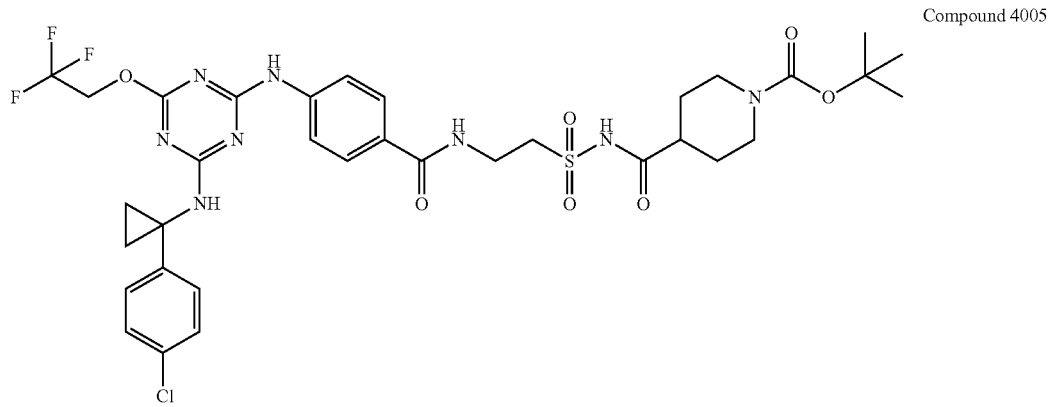 [SMILES: CC(C)(C)OC(=O)N1CCC(C(=O)NS(=O)(=O)CCNC(=O)c2ccc(Nc3nc(NC4(c5ccc(Cl)cc5)CC4)nc(OCC(F)(F)F)n3)cc2)CC1]
Compound 4005

Compound 4005 was prepared by the same method as compound 4000 with the following modifications: 1-(tert-butoxycarbonyl)piperidine-4-carboxylic acid instead of acetic acid in Step 3 was used as a starting material. After HPLC, the product fractions were diluted with EtOAc and washed with water 2×, followed by brine. The organic layer was collected, dried over sodium sulfate, and concentrated under vacuum to give compound 4005 (17 mg). 1H NMR (400 MHz, DMSO-$d_6$) δ ppm 1.23-1.46 (m, 15H), 1.61-1.76 (m, 2H), 2.36-2.44 (m, 1H), 2.59-2.77 (m, 2H), 3.56-3.70 (m, 4H), 3.80-3.97 (m, 2H), 4.99 (q, J=9.0 Hz, 2H), 7.19-7.42 (m, 4H), 7.57-7.95 (m, 4H), 8.38-8.60 (m, 1H), 8.80 (br. s., 1H), 9.96 (br. s., 1H), 11.74 (s, 1H); LC-MS (Condition A), MS m/z (M$^+$+H) 797.0.

Example 5000

Preparation of Compounds 5000

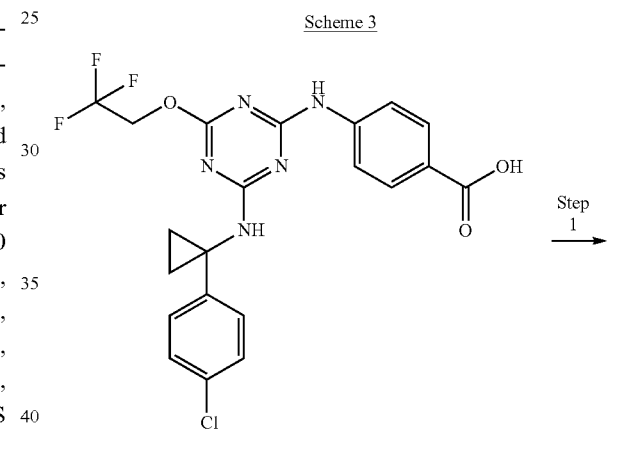
Compound 5000

Scheme 3

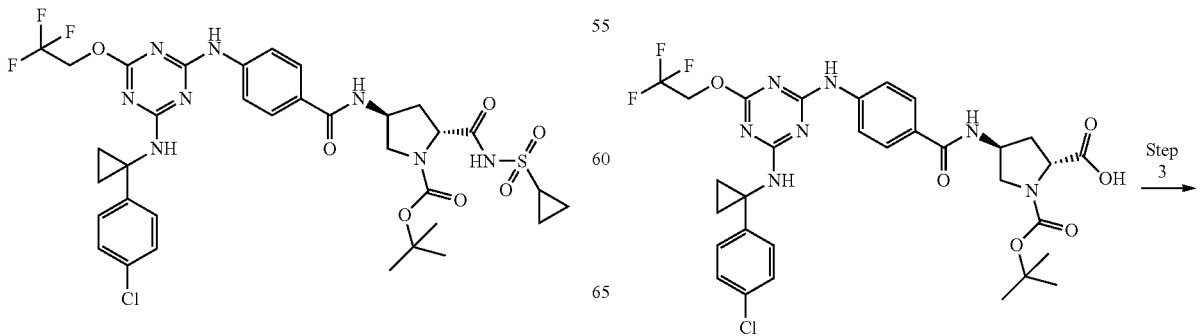

149

-continued

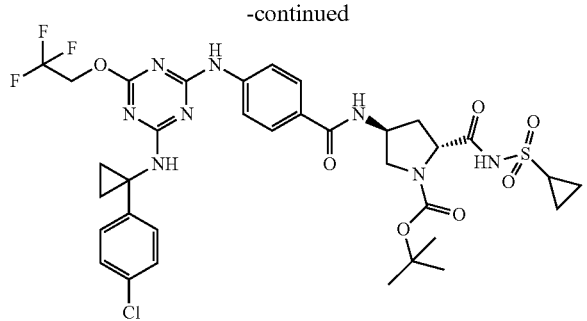

Step 1:

4-(4-(1-(4-chlorophenyl)cyclopropylamino)-6-(2,2,2-trifluoroethoxy)-1,3,5-triazin-2-ylamino)benzoic acid (400 mg, 0.834 mmol), (2S,4R)-1-tert-butyl 2-methyl 4-aminopyrrolidine-1,2-dicarboxylate (224 mg, 0.917 mmol), PyBOP (651 mg, 1.250 mmol), and Hunig's Base (0.728 mL, 4.17 mmol) were stirred in DCM (Volume: 10 mL) for 3 days. The solvent was removed and the crude material was purified by silica gel chromatography using 60% EtOAc/hexanes to give (2R,4S)-1-tert-butyl 2-methyl 4-(4-(4-(1-(4-chlorophenyl)cyclopropylamino)-6-(2,2,2-trifluoroethoxy)-1,3,5-triazin-2-ylamino)benzamido)pyrrolidine-1,2-dicarboxylate (500 mg). 1H NMR (400 MHz, MeOD) δ ppm 1.33-1.41 (m, 4H), 1.43 (s, 9H), 2.25-2.48 (m, 2H), 3.39-3.47 (m, 1H), 3.78 (s, 3H), 3.81-3.90 (m, 1H), 4.46 (td, J=7.7, 4.8 Hz, 1H), 4.64 (qd, J=5.8, 5.6 Hz, 1H), 4.85-4.93 (m, 2H), 7.20-7.32 (m, 4H), 7.58-7.71 (m, 3H), 7.76-7.92 (m, 1H); LC-MS (Condition A), MS m/z (M$^+$+H) 706.1.

Step 2:

(2S,4R)-1-tert-butyl 2-methyl 4-(4-(4-(1-(4-chlorophenyl)cyclopropylamino)-6-(2,2,2-trifluoroethoxy)-1,3,5-triazin-2-ylamino)benzamido)pyrrolidine-1,2-dicarboxylate (500 mg, 0.708 mmol), was dissolved in THF (Ratio: 1.000, Volume: 4 mL) followed by the addition of LiOH (85 mg, 3.54 mmol) and Water (Ratio: 1.000, Volume: 4). The reaction was heated to 65° C. for 2 h. The reaction was diluted with EtOAc and acidified with 1N HCl. The organic layer was collected, washed with brine, dried over sodium sulfate, and concen-

150 trated under vacuum to give (2R,4S)-1-(tert-butoxycarbonyl)-4-(4-(4-(1-(4-chlorophenyl)cyclopropylamino)-6-(2,2,2-trifluoroethoxy)-1,3,5-triazin-2-ylamino)benzamido)pyrrolidine-2-carboxylic acid (490 mg) which was used in the next step without further purification. 1H NMR (400 MHz, MeOD) δ ppm 1.33-1.41 (m, 4H), 1.45 (s, 9H), 2.28-2.49 (m, 2H), 3.40-3.47 (m, 1H), 3.85 (dd, J=10.7, 6.9 Hz, 1H), 4.33-4.47 (m, 1H), 4.60-4.72 (m, 1H), 4.86-4.93 (m, 2H), 7.20-7.32 (m, 4H), 7.59-7.71 (m, 3H), 7.77-7.89 (m, 1H); LC-MS (Condition A), MS m/z (M$^+$+H) 692.0.

Step 3:

(2R,4S)-1-(tert-butoxycarbonyl)-4-(4-(4-(1-(4-chlorophenyl)cyclopropylamino)-6-(2,2,2-trifluoroethoxy)-1,3,5-triazin-2-ylamino)benzamido)pyrrolidine-2-carboxylic acid (20 mg, 0.029 mmol), cyclopropanesulfonamide (4.20 mg, 0.035 mmol), PyBOP (22.56 mg, 0.043 mmol), and Hunig's Base (0.025 mL, 0.144 mmol) were stirred in DCM (Volume: 2 mL) for 16 h. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier. The product fractions were diluted with EtOAc and washed with water 2×, followed by brine. The organic layer was collected, dried over sodium sulfate, and concentrated under vacuum to give compound 5000 (14 mg). 1H NMR (500 MHz, MeOD) δ ppm 1.07-1.44 (m, 9H), 1.48 (s, 9H), 2.26-2.51 (m, 2H), 3.38-3.49 (m, 1H), 3.84-3.96 (m, 1H), 4.30-4.45 (m, 1H), 4.58-4.73 (m, 1H), 4.81-4.85 (m, 2H), 7.18-7.36 (m, 4H), 7.58-7.73 (m, 3H), 7.76-7.90 (m, 1H); LC-MS (Condition A), MS m/z (M$^+$+H) 795.0.

Example 5001

Preparation of Compound 5001

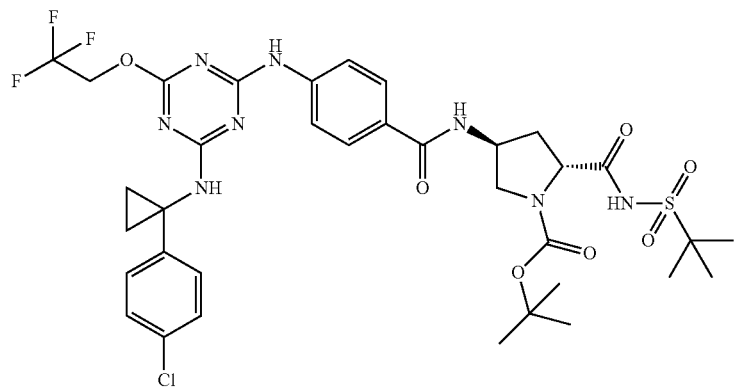

Compound 5001

Compound 5001 was prepared by the same method as Compound 5000 with the following modifications: 2-methylpropane-2-sulfonamide instead of cyclopropyl sulfonamide in Step 3 was used as a starting material to give Compound 1301 (6 mg). LC-MS (Condition A), MS m/z (M$^+$+H) 811.1.

Example 5002

Preparation of Compound 5002

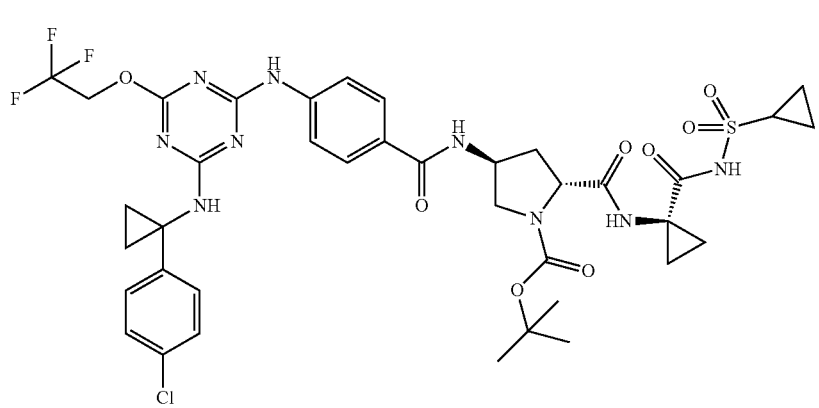

Compound 5002

Compound 5002w as prepared by modification of Step 3 of the method to prepare compound 1300. (2R,4S)-1-(tert-butoxycarbonyl)-4-(4-(4-(1-(4-chlorophenyl)cyclopropylamino)-6-(2,2,2-trifluoroethoxy)-1,3,5-triazin-2-ylamino)benzamido)pyrrolidine-2-carboxylic acid (20 mg, 0.029 mmol), (1S,2R)-2-amino-N-(cyclopropylsulfonyl)bi(cyclopropane)-2-carboxamide (8.47 mg, 0.035 mmol), PyBOP (22.56 mg, 0.043 mmol), and Hunig's Base (0.025 mL, 0.144 mmol) were stirred in DCM (Volume: 2 mL) for 16 h. The solvent was removed under vacuum and the crude product was purified by rev. phase preparative HPLC (Column: Sunfire prep C18 OBO 5 uM, 30×100 mm by Waters Corp) using a gradient of 30-100% ACN/water w/0.1% TFA modifier. The product fractions were diluted with EtOAc and washed with water 2×, followed by brine. The organic layer was collected, dried over sodium sulfate, and concentrated under vacuum to give Compound 5002 (14 mg). LC-MS (Condition A), MS m/z (M$^+$+H) 918.2.

Example 6000

Preparation of Compound 6000

Compound 6000

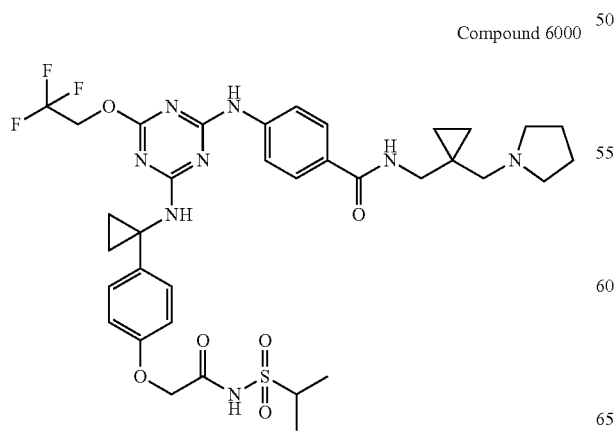

Scheme 1
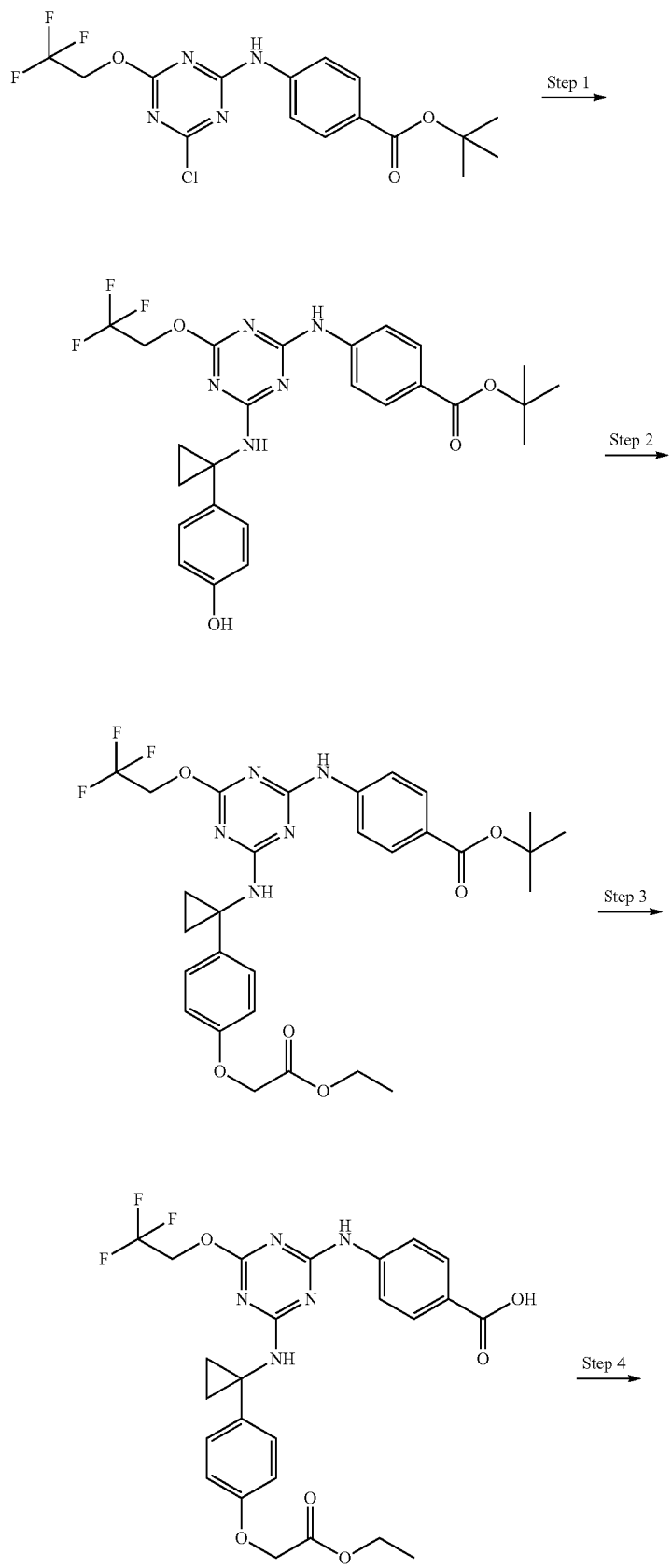

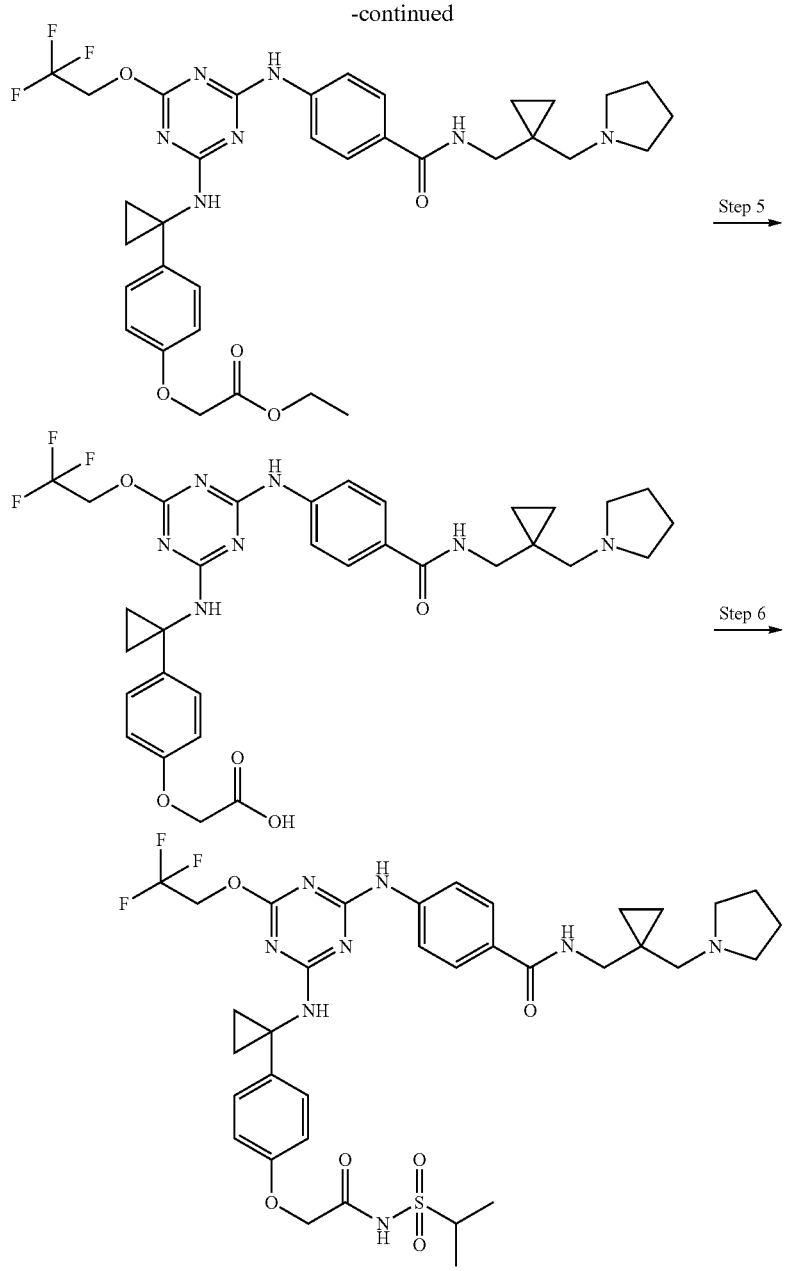

Step 1:

To a solution of tert-butyl 4-(4-chloro-6-(2,2,2-trifluoroethoxy)-1,3,5-triazin-2-ylamino)benzoate (2 g, 4.94 mmol) in THF (30 mL) was added 4-(1-aminocyclopropyl)phenol (0.811 g, 5.44 mmol) and Hunig's Base (3.45 mL, 19.76 mmol). The resulting mixture was stirred for 16 h. The reaction was then warmed to 65° C. for 2 h at which point the reaction became a homogeneous solution. The reaction was cooled and diluted with DCM and washed with water and brine. The organic layer was collected, dried over sodium sulfate, and concentrated under vacuum to give an oily residue. The residue was purified by silica gel chromatography using 20-40% EtOAc/Hexanes to give tert-butyl 4-(4-(1-(4-hydroxyphenyl)cyclopropylamino)-6-(2,2,2-trifluoroethoxy)-1,3,5-triazin-2-ylamino)benzoate (2 g). 1H NMR (400 MHz, CHLOROFORM-d) δ ppm 1.30-1.37 (m, 4H), 1.60 (s, 9H), 4.67-4.77 (m, 2H), 4.85 (br. s., 1H), 6.04 (br. s., 1H), 6.70-6.81 (m, 2H), 7.11-7.22 (m, 2H), 7.47-7.66 (m, 2H), 7.79-8.01 (m, 2H); LC-MS (Condition A), MS m/z (M⁺+H) 518.0.

Step 2:

To a solution of tert-butyl 4-(4-(1-(4-hydroxyphenyl)cyclopropylamino)-6-(2,2,2-trifluoroethoxy)-1,3,5-triazin-2-ylamino)benzoate (300 mg, 0.580 mmol) in DMF (Volume: 4 mL) was added ethyl 2-bromoacetate (0.067 mL, 0.609 mmol) and POTASSIUM CARBONATE (401 mg, 2.90 mmol). The mixture was at rt for 16 h. After cooling to rt, the mixture was diluted with EtOAc, washed with water, and brine. The organic layer was dried over MgSO4 and concentrated. The residue was purified by silica gel chromatography using 40% EtOAc/Hexanes to give tert-butyl 4-(4-(1-(4-(2-ethoxy-2-oxoethoxy)phenyl)cyclopropylamino)-6-(2,2,2- trifluoroethoxy)-1,3,5-triazin-2-ylamino)benzoate (350 mg). LC-MS (Condition C), MS m/z (M⁺+H) 576.4.

Step 3:

tert-butyl 4-(4-(1-(4-(2-ethoxy-2-oxoethoxy)phenyl)cyclopropylamino)-6-(2,2,2-trifluoroethoxy)-1,3,5-triazin-2-ylamino)benzoate (350 mg, 0.580 mmol) and 4 N HCl in Dioxane (2 mL, 8.00 mmol) were stirred for 1 h then concentrated under vacuum to give 4-(4-(1-(4-(2-ethoxy-2-oxoethoxy)phenyl)cyclopropylamino)-6-(2,2,2-trifluoroethoxy)-1,3,5-triazin-2-ylamino)benzoic acid (330 mg) which was used in the next step without purification. LC-MS (Condition A), MS m/z (M⁺+H) 548.0.

Step 4:

4-(4-(1-(4-(2-ethoxy-2-oxoethoxy)phenyl)cyclopropylamino)-6-(2,2,2-trifluoroethoxy)-1,3,5-triazin-2-ylamino)benzoic acid (330 mg, 0.603 mmol), (1-(pyrrolidin-1-ylmethyl)cyclopropyl)methanamine (112 mg, 0.723 mmol), HATU (344 mg, 0.904 mmol), and Hunig's Base (0.526 mL, 3.01 mmol) were stirred in DCM (Volume: 5 mL) for 16 h. The solvent was removed and the crude material was purified by silica gel chromatography using EtOAc then 5% DCM/MeOH to give ethyl 2-(4-(1-(4-(4-((1-(pyrrolidin-1-ylmethyl)cyclopropyl)methylcarbamoyl)phenylamino)-6-(2,2,2-trifluoroethoxy)-1,3,5-triazin-2-ylamino)cyclopropyl)phenoxy)acetate (268 mg). LC-MS (Condition A), MS m/z (M⁺+H) 684.1.

Step 5:

ethyl 2-(4-(1-(4-(4-((1-(pyrrolidin-1-ylmethyl)cyclopropyl)methylcarbamoyl)phenylamino)-6-(2,2,2-trifluoroethoxy)-1,3,5-triazin-2-ylamino)cyclopropyl)phenoxy)acetate (268 mg, 0.392 mmol) was dissolved in THF (Ratio: 1.000, Volume: 2 mL) then LiOH (46.9 mg, 1.960 mmol) and Water (Ratio: 1.000, Volume: 2 mL) were added and the reaction was heated to 65° C. for 2 h. The solvent was removed under vacuum and water was added back to the flask and the pH adjusted to ~7 with 1N HCl. A solid precipitated out of solution and this was collected, washed with water, and dried to give 2-(4-(1-(4-(4-((1-(pyrrolidin-1-ylmethyl)cyclopropyl)methylcarbamoyl)phenylamino)-6-(2,2,2-trifluoroethoxy)-1,3,5-triazin-2-ylamino)cyclopropyl)phenoxy)acetic acid (130 mg). 1H NMR (400 MHz, MeOD) δ ppm 0.62-0.70 (m, 2H), 0.94-1.02 (m, 2H), 1.15-1.34 (m, 4H), 2.10 (br. s., 4H), 3.08 (br. s., 2H), 3.30-3.33 (m, 4H), 3.49 (s, 2H), 4.51 (s, 2H), 4.86-4.93 (m, 2H), 6.85-6.94 (m, 2H), 7.08-7.16 (m, 2H), 7.16-7.25 (m, 2H), 7.42-7.54 (m, 2H); LC-MS (Condition A), MS m/z (M⁺+H) 656.1.

Step 6:

2-(4-(1-(4-(4-((1-(pyrrolidin-1-ylmethyl)cyclopropyl)methylcarbamoyl)phenylamino)-6-(2,2,2-trifluoroethoxy)-1,3,5-triazin-2-ylamino)cyclopropyl)phenoxy)acetic acid (20 mg, 0.031 mmol), propane-2-sulfonamide (4.88 mg, 0.040 mmol), PyBOP (23.81 mg, 0.046 mmol), and Hunig's Base (0.027 mL, 0.153 mmol) were stirred in DCM (Volume: 3 mL) for 3 days. The solvent was removed and the crude material was purified by Prep-HPLC (Column: Sunfire prep C18 OBO 5 uM, 30×100 mm by Waters Corp) using a gradient of 10-60% ACN/water w/0.1% TFA modifier to give 4-(4-(1-(4-(2-(1-methylethylsulfonamido)-2-oxoethoxy)phenyl)cyclopropylamino)-6-(2,2,2-trifluoroethoxy)-1,3,5-triazin-2-ylamino)-N-((1-(pyrrolidin-1-ylmethyl)cyclopropyl)methyl)benzamide (5 mg). 1H NMR (500 MHz, MeOD) δ ppm 0.75 (s, 2H), 0.83 (s, 2H), 1.14-1.42 (m, 10H), 2.12-2.26 (m, 4H), 3.06-3.43 (m, 7H), 3.77-3.88 (m, 2H), 4.64 (s, 2H), 4.81-4.92 (m, 2H), 6.86-7.00 (m, 2H), 7.21-7.32 (m, 2H), 7.64-7.76 (m, 3H), 7.89 (s, 1H); LC-MS (Condition A), MS m/z (M⁺+H) 761.2.

Example 7001

Preparation of Compounds 7001

Compound 7001

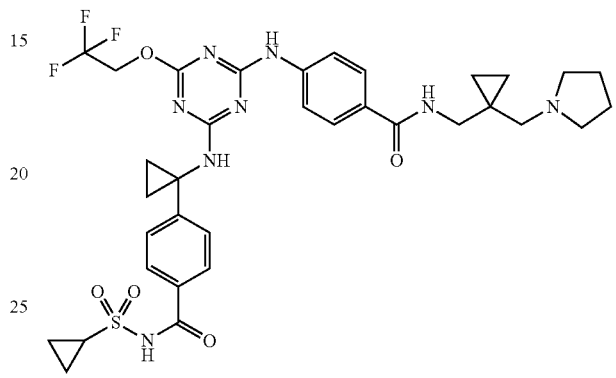

Scheme 1

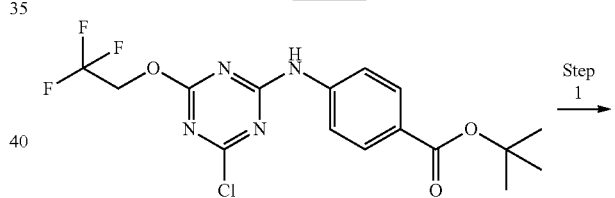

Step 1

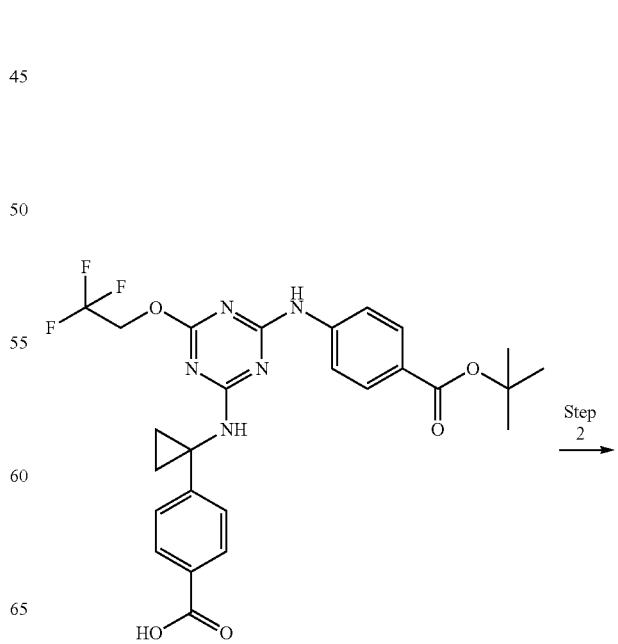

Step 2

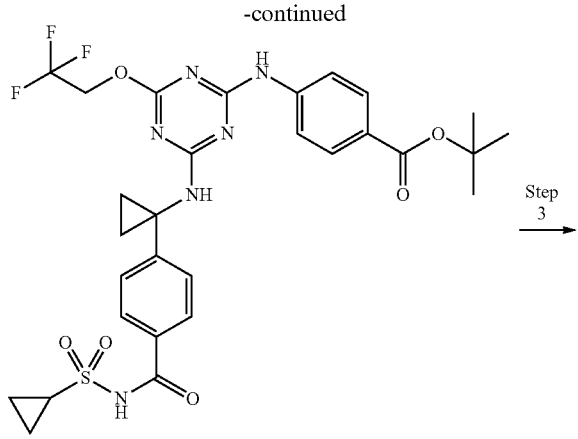

Step 3 →

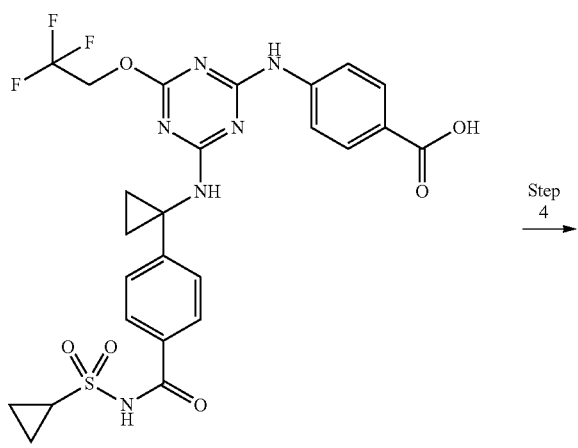

Step 4 → zoic acid was prepared by the same method as Example 1001 step 3 with the following modifications: 4-(1-aminocyclopropyl)benzoic acid instead of 1-(4-chlorophenyl)cyclopropanamine was used as a starting material to give 4-(1-(4-(4-(tert-butoxycarbonyl)phenylamino)-6-(2,2,2-trifluoroethoxy)-1,3,5-triazin-2-ylamino)cyclopropyl)benzoic acid (70 mg). LC-MS (Condition A), MS m/z (M$^+$+H) 546.1.

Step 2:

tert-butyl 4-(4-(1-(4-(cyclopropylsulfonylcarbamoyl)phenyl)cyclopropylamino)-6-(2,2,2-trifluoroethoxy)-1,3,5-triazin-2-ylamino)benzoate was prepared by the same method as Example 1001 step 4 to give tert-butyl 4-(4-(1-(4-(cyclopropylsulfonylcarbamoyl)phenyl)cyclopropylamino)-6-(2,2,2-trifluoroethoxy)-1,3,5-triazin-2-ylamino)benzoate (24 mg). LC-MS (Condition A), MS m/z (M$^+$+H) 649.2.

Step 3:

4-(4-(1-(4-(cyclopropylsulfonylcarbamoyl)phenyl)cyclopropylamino)-6-(2,2,2-trifluoroethoxy)-1,3,5-triazin-2-ylamino)benzoic acid was prepared by the same method as Example 6000 step 3 to give 4-(4-(1-(4-(cyclopropylsulfonylcarbamoyl)phenyl)cyclopropylamino)-6-(2,2,2-trifluoroethoxy)-1,3,5-triazin-2-ylamino)benzoic acid (20 mg). LC-MS (Condition A), MS m/z (M$^+$+H) 593.0.

Step 4:

N-(cyclopropylsulfonyl)-4-(1-(4-(4-((1-(pyrrolidin-1-ylmethyl)cyclopropyl)methylcarbamoyl)phenylamino)-6-(2,2,2-trifluoroethoxy)-1,3,5-triazin-2-ylamino)cyclopropyl)benzamide was prepared by the same method as Example 6000 step 4 to give Compound 7001 (6 mg) as the TFA salt. LC-MS (Condition A), MS m/z (M$^+$+H) 729.2.

Example 7002

Preparation of Compounds 7002

Compound 7002

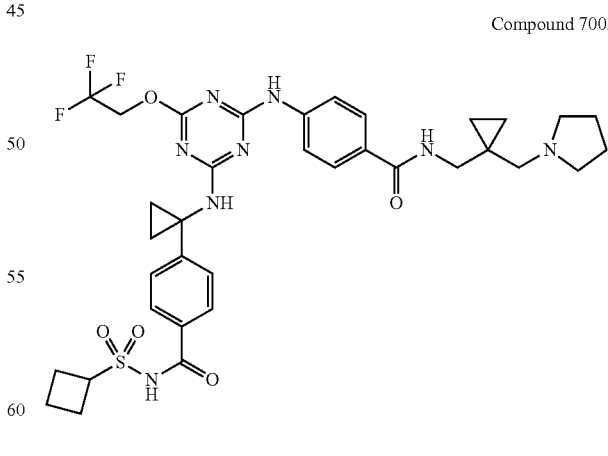

Step 1:

4-(1-(4-(4-(tert-butoxycarbonyl)phenylamino)-6-(2,2,2-trifluoroethoxy)-1,3,5-triazin-2-ylamino)cyclopropyl)ben- Compound 7002 was prepared by the same method as Compound 7002 with the following modifications: cyclobutane sulfonamide instead of cyclopropanesulfonamide in Step 2 was used as a starting material to give Compound 7002 (2.5 mg) as the TFA salt. LC-MS (Condition A), MS m/z (M$^+$+H) 743.2.

Example 7003

Preparation of Compounds 7003

Compound 7003

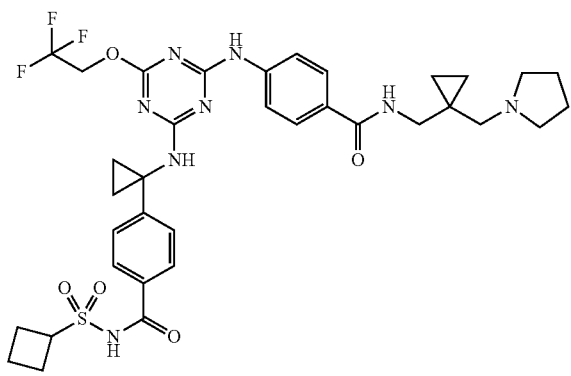

Compound 7003 was prepared by the same method as Compound 7001 with the following modifications: benzene sulfonamide instead of cyclopropanesulfonamide in Step 2 was used as a starting material to give Compound 7003 (5 mg) as the TFA salt. LC-MS (Condition A), MS m/z (M$^+$+H) 765.2.

Procedures for the Synthesis of 8000 Series Examples in Table 3.

Compounds in table 3 can be prepared similarly by either following method or above described methods.

Scheme 1

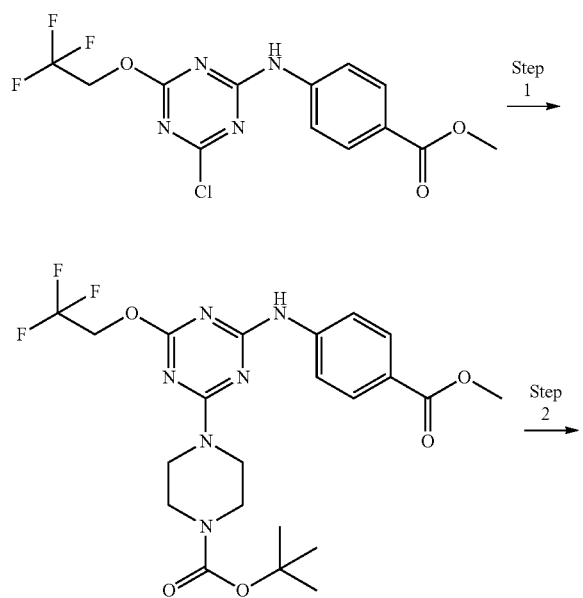

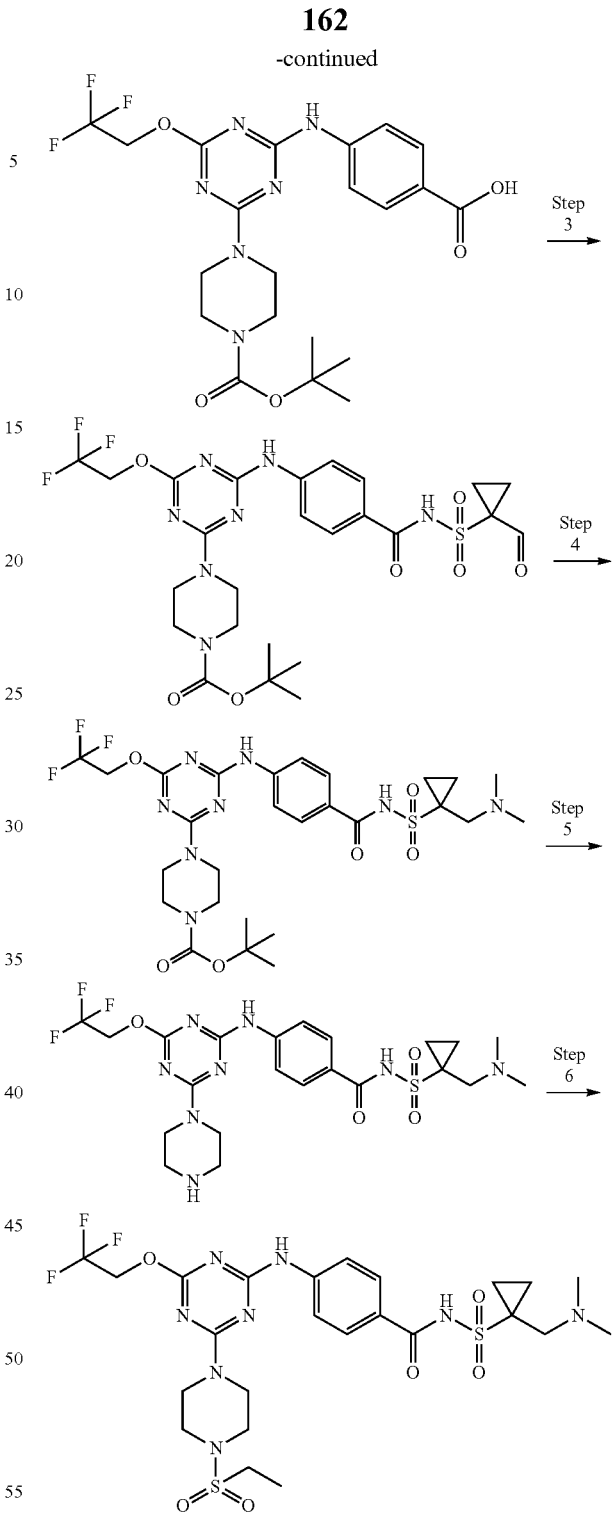

Step 1:

To a slurry of methyl 4-(4-chloro-6-(2,2,2-trifluoroethoxy)-1,3,5-triazin-2-ylamino)benzoate (1.813 g, 5 mmol) and tert-butyl piperazine-1-carboxylate (1.024 g, 5.50 mmol) in THF (50 mL) was stirred at rt for 5 h. After concentration, the white solid was collected through a plug washing with water to give 2.51 g of the desired product after drying in house vacuum. LC-MS (Condition B), MS m/z (M$^+$+H) 512.10.

Step 2:

A mixture of tert-butyl 4-(4-(4-(methoxycarbonyl)phenylamino)-6-(2,2,2-trifluoroethoxy)-1,3,5-triazin-2-yl)piperazine-1-carboxylate (2.5 g, 4.88 mmol) and NaOH (0.780 g, 19.51 mmol) in THF (20 mL) and water (10.00 mL) was refluxed for 6 h. The reaction was diluted with water and extracted with ether (50 mL×2) to remove unreacted staring material, the inorganic layer was acidified with 1 N HCl, extracted with ethyl acetate, dried over MgSO4, concentrated to give 1.2 g of a crude product, which will be used in the next step as it is. LC-MS (Condition B), MS m/z (M$^+$+H) 499.08.

Step 3:

To a solution of 4-(4-(4-(tert-butoxycarbonyl)piperazin-1-yl)-6-(2,2,2-trifluoroethoxy)-1,3,5-triazin-2-ylamino)benzoic acid (0.648 g, 1.3 mmol), 1-formylcyclopropane-1-sulfonamide (0.223 g, 1.495 mmol), and Hunig's Base (1.135 mL, 6.50 mmol) in CH$_2$Cl$_2$ (10 mL) was added PyBOP (0.812 g, 1.560 mmol) and then stirred for 16 h. After concentration, the residue was purified by Biotage eluting with ethyl acetate and then 10% MeOH in CH$_2$Cl$_2$ to give g of a crude product that containing some impurity, which will be used in next step as it is. LC-MS (Condition M), MS m/z (M$^+$+H) 630.10.

Step 4:

A stirred solution of tert-butyl 4-(4-(4-(1-formylcyclopropylsulfonylcarbamoyl)phenylamino)-6-(2,2,2-trifluoroethoxy)-1,3,5-triazin-2-yl)piperazine-1-carboxylate (400 mg, 0.635 mmol) in DCE (10 mL) was treated with dimethylamine, 2 M in THF (0.635 mL, 1.271 mmol) followed by NaBH(OAc)$_3$ (404 mg, 1.906 mmol). After stirring at rt for 2 h, the reaction was diluted with CH$_2$Cl$_2$ and quenched with water, dried over Na$_2$SO$_4$, concentrated to give 400 mg that will be used as it is. LC-MS (Condition B), MS m/z (M$^+$+H) 659.18.

Step 5:

A solution of tert-butyl 4-(4-(4-(1-((dimethylamino)methyl)cyclopropylsulfonylcarbamoyl)phenylamino)-6-(2,2,2-trifluoroethoxy)-1,3,5-triazin-2-yl)piperazine-1-carboxylate (470 mg, 0.714 mmol) in TFA (Volume: 10 mL) was stirred for 2 h. Concentration gave 561 mg of a crude product as TFA salt that will be used in the next step as it is. LC-MS (Condition B), MS m/z (M$^+$+H) 559.10.

Step 6:

To a solution of N-(1-((dimethylamino)methyl)cyclopropylsulfonyl)-4-(4-(piperazin-1-yl)-6-(2,2,2-trifluoroethoxy)-1,3,5-triazin-2-ylamino)benzamide, 2 TFA (15 mg, 0.019 mmol) and Hunig's Base (0.033 mL, 0.191 mmol) in CH$_2$Cl$_2$ (1 mL) was added ethanesulfonyl chloride (7.36 mg, 0.057 mmol) and then stirred for 10 min. After quenching with water and concentration, the residue was purified by prep HPLC to give 10 mg (65%) of the Example 8023 in Table 1 as a TFA salt. 1H NMR (400 MHz, MeOD) δ ppm 1.28-1.36 (m, 5H), 1.73-1.80 (m, 2H), 3.05-3.10 (m, 8H), 3.33-3.39 (m, 4H), 3.72 (s, 2H), 3.98 (s, 4H), 4.82-4.92 (m, 2H), 7.82-7.87 (m, 2H), 7.93-7.98 (m, 2H); LC-MS (Condition B), MS m/z (M$^+$+H) 651.19.

TABLE 3

| Examples | Structure | MW | LM/MS, MS m/z (M+ +H) Condition B |
|---|---|---|---|
| 8001 | Chiral | 555.54 | 556.23 |
| 8002 | 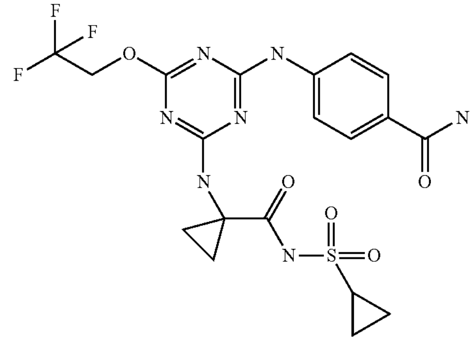 [SMILES: NC(=O)c1ccc(Nc2nc(NC3(C(=O)NS(=O)(=O)C4CC4)CC3)nc(OCC(F)(F)F)n2)cc1] | 515.47 | 516.16 |

TABLE 3-continued

| Examples | Structure | MW | LM/MS, MS m/z (M+ +H) Condition B |
|---|---|---|---|
| 8003 | 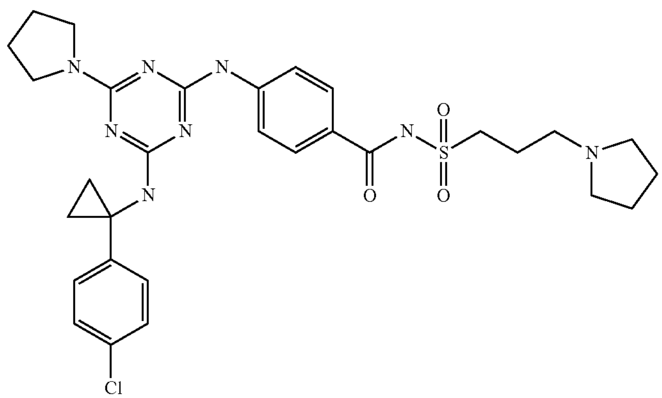 [SMILES: O=C(NS(=O)(=O)CCCN1CCCC1)c1ccc(Nc2nc(NC3(c4ccc(Cl)cc4)CC3)nc(N3CCCC3)n2)cc1] | 625.19 | 625.20 |
| 8004 | 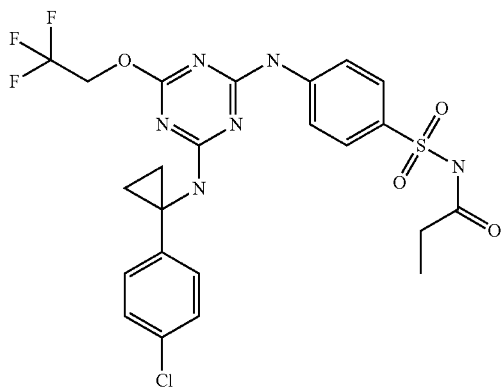 [SMILES: CCC(=O)NS(=O)(=O)c1ccc(Nc2nc(NC3(c4ccc(Cl)cc4)CC3)nc(OCC(F)(F)F)n2)cc1] | 570.98 | 571.06 |
| 8005 | 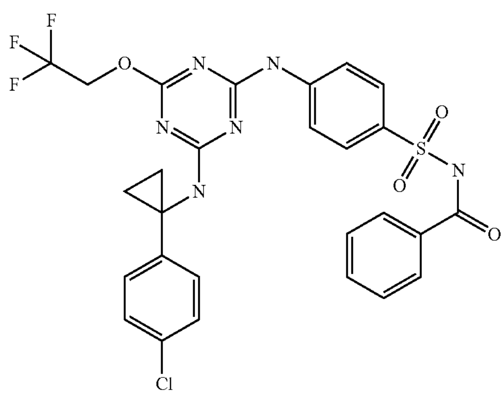 [SMILES: O=C(NS(=O)(=O)c1ccc(Nc2nc(NC3(c4ccc(Cl)cc4)CC3)nc(OCC(F)(F)F)n2)cc1)c1ccccc1] | 619.02 | 619.10 |
| 8006 | 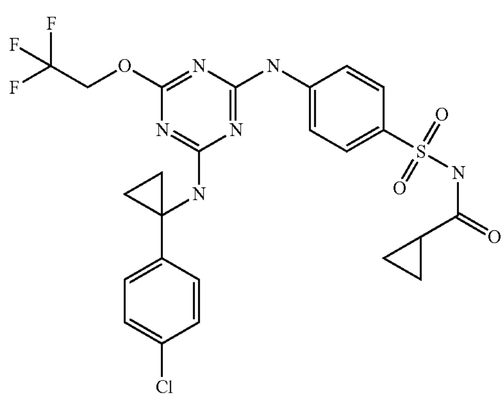 [SMILES: O=C(NS(=O)(=O)c1ccc(Nc2nc(NC3(c4ccc(Cl)cc4)CC3)nc(OCC(F)(F)F)n2)cc1)C1CC1] | 582.99 | 583.08 |

TABLE 3-continued

| Examples | Structure | MW | LM/MS, MS m/z (M+ +H) Condition B |
|---|---|---|---|
| 8007 | 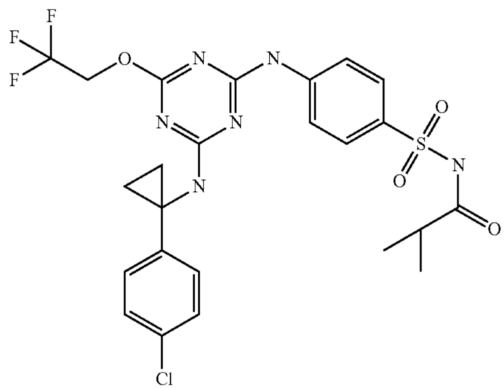 [SMILES: CC(C)C(=O)NS(=O)(=O)c1ccc(Nc2nc(NC3(c4ccc(Cl)cc4)CC3)nc(OCC(F)(F)F)n2)cc1] | 585.01 | 585.09 |
| 8008 | 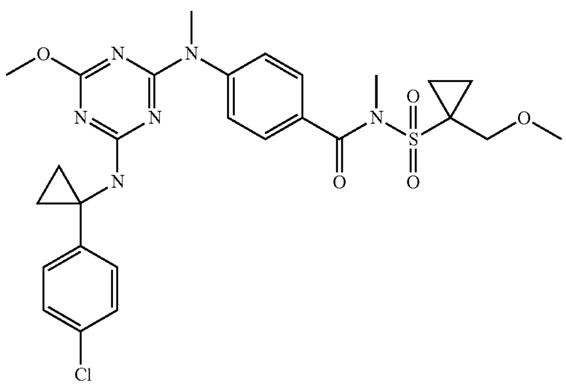 | 587.10 | 587.18 |
| 8009 | 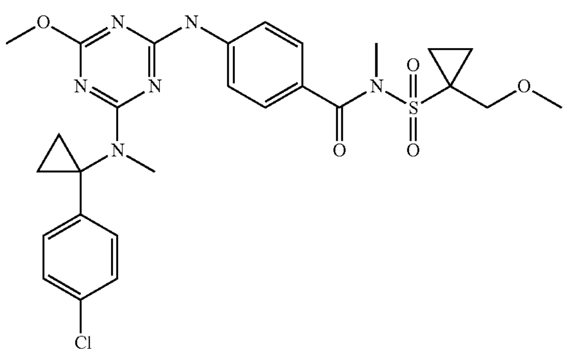 | 587.10 | 587.16 |
| 8010 | 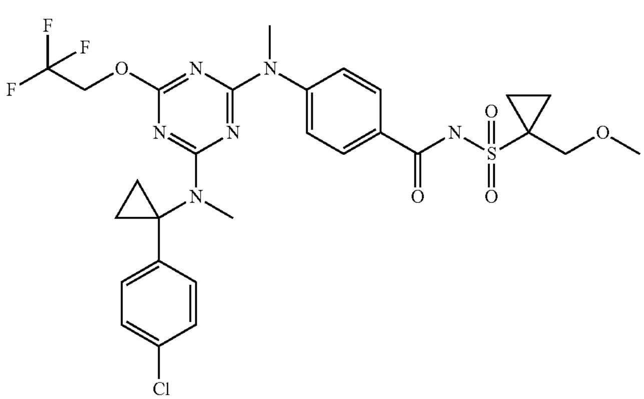 [SMILES: COCC1(S(=O)(=O)NC(=O)c2ccc(N(C)c3nc(OCC(F)(F)F)nc(N(C)C4(c5ccc(Cl)cc5)CC4)n3)cc2)CC1] | 655.10 | 655.19 |

TABLE 3-continued

| Examples | Structure | MW | LM/MS, MS m/z (M+ +H) Condition B |
|---|---|---|---|
| 8011 | 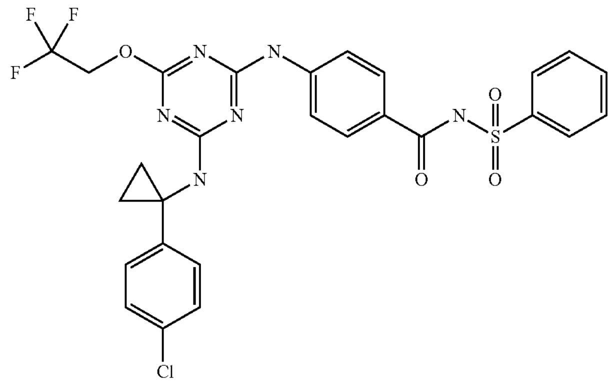 [SMILES: O=C(NS(=O)(=O)c1ccccc1)c1ccc(Nc2nc(NC3(c4ccc(Cl)cc4)CC3)nc(OCC(F)(F)F)n2)cc1] | 619.02 | 619.07 |
| 8012 | 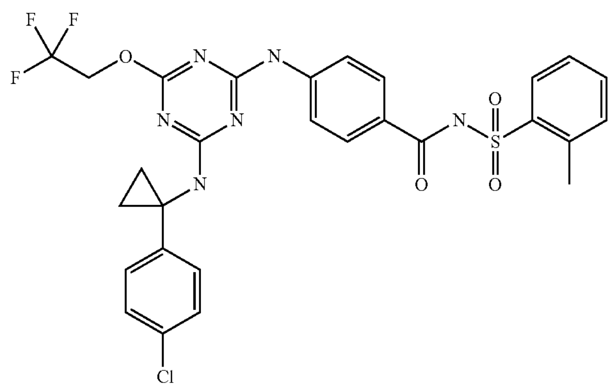 [SMILES: Cc1ccccc1S(=O)(=O)NC(=O)c1ccc(Nc2nc(NC3(c4ccc(Cl)cc4)CC3)nc(OCC(F)(F)F)n2)cc1] | 633.05 | 633.10 |
| 8013 | 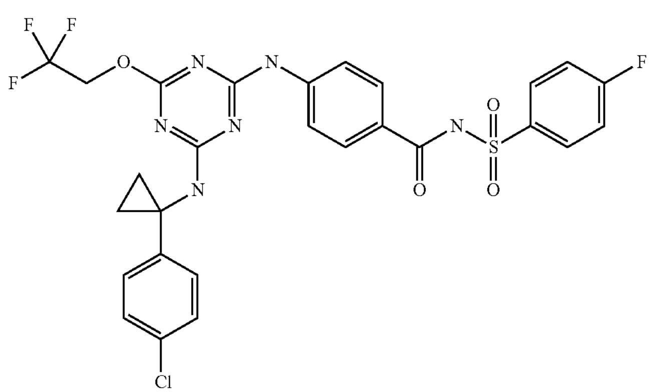 [SMILES: O=C(NS(=O)(=O)c1ccc(F)cc1)c1ccc(Nc2nc(NC3(c4ccc(Cl)cc4)CC3)nc(OCC(F)(F)F)n2)cc1] | 637.01 | 637.06 |
| 8014 | 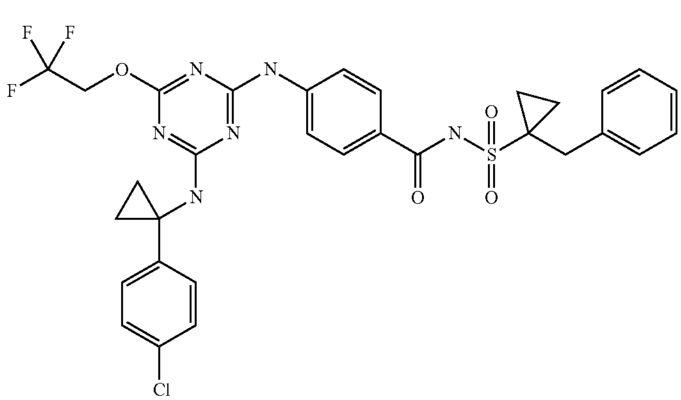 [SMILES: O=C(NS(=O)(=O)C1(Cc2ccccc2)CC1)c1ccc(Nc2nc(NC3(c4ccc(Cl)cc4)CC3)nc(OCC(F)(F)F)n2)cc1] | 673.11 | 673.11 |

TABLE 3-continued
| Examples | Structure | MW | LM/MS, MS m/z (M+ +H) Condition B |
|---|---|---|---|
| 8015 | 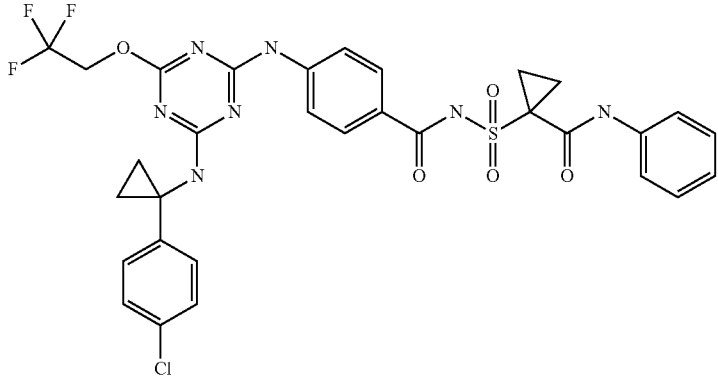 [SMILES: O=C(NS(=O)(=O)C1(C(=O)Nc2ccccc2)CC1)c1ccc(Nc2nc(NC3(c4ccc(Cl)cc4)CC3)nc(OCC(F)(F)F)n2)cc1] | 702.11 | 702.16 |
| 8016 | 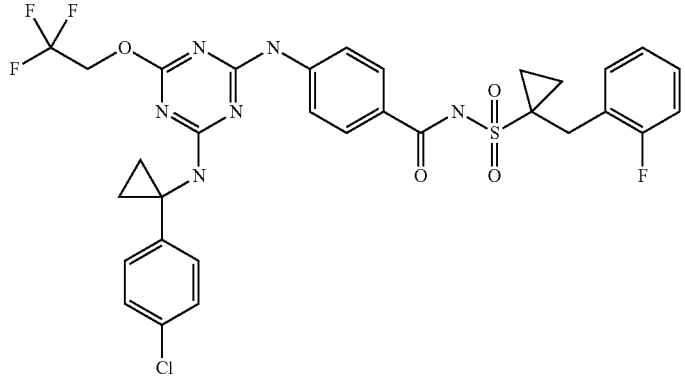 [SMILES: O=C(NS(=O)(=O)C1(Cc2ccccc2F)CC1)c1ccc(Nc2nc(NC3(c4ccc(Cl)cc4)CC3)nc(OCC(F)(F)F)n2)cc1] | 691.10 | 691.14 |
| 8017 | 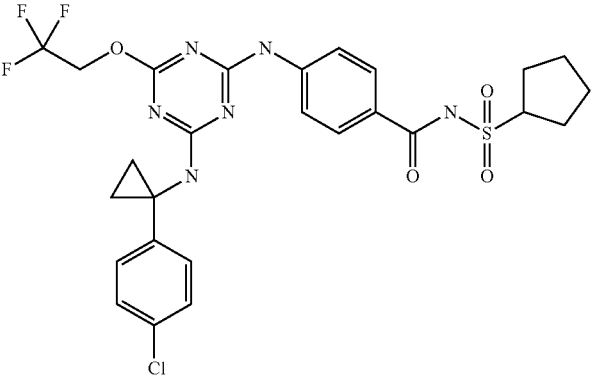 [SMILES: O=C(NS(=O)(=O)C1CCCC1)c1ccc(Nc2nc(NC3(c4ccc(Cl)cc4)CC3)nc(OCC(F)(F)F)n2)cc1] | 611.04 | 611.10 |
| 8018 | 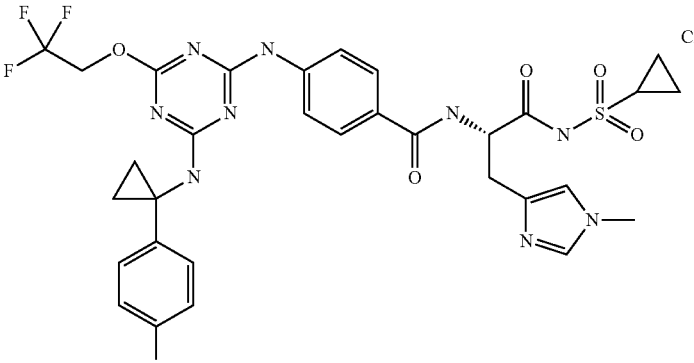 Chiral | 734.16 | 734.15 |

TABLE 3-continued
| Examples | Structure | MW | LM/MS, MS m/z (M+ +H) Condition B |
|---|---|---|---|
| 8019 | 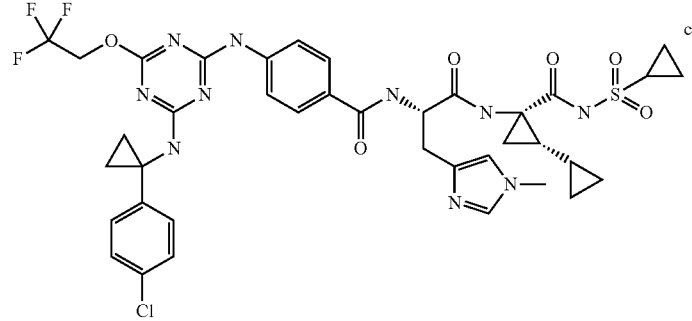 | 857.31 | 857.17 |
| 8020 | 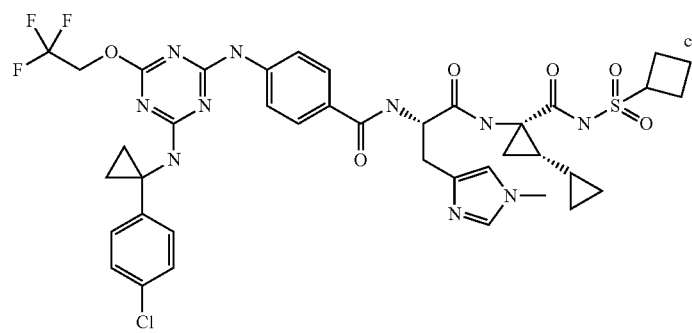 | 871.34 | 871.18 |
| 8021 | 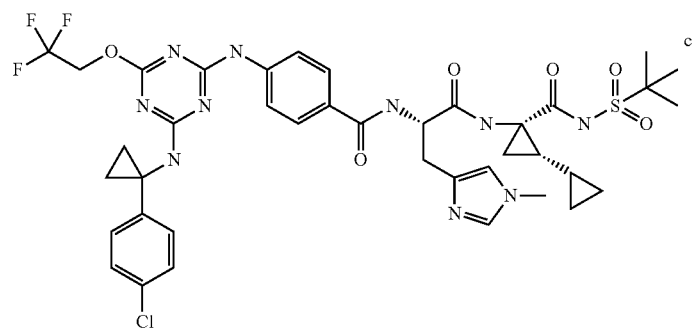 | 873.35 | 873.20 |
| 8022 | 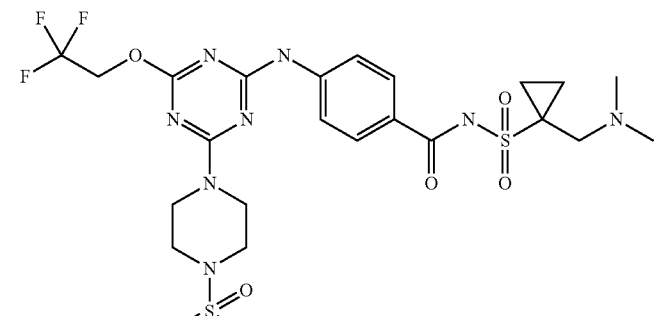 | 636.67 | 637.19 |

TABLE 3-continued

| Examples | Structure | MW | LM/MS, MS m/z (M+ +H) Condition B |
|---|---|---|---|
| 8023 | 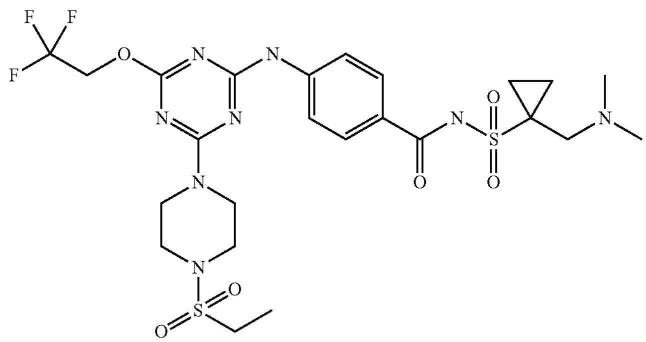 [SMILES: CCS(=O)(=O)N1CCN(c2nc(Nc3ccc(C(=O)NS(=O)(=O)C4(CN(C)C)CC4)cc3)nc(OCC(F)(F)F)n2)CC1] | 650.70 | 651.19 |
| 8024 | 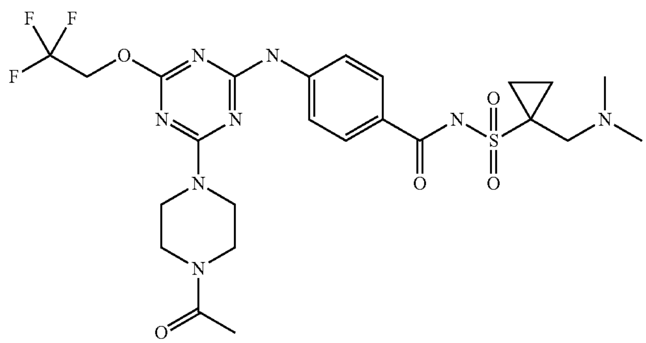 [SMILES: CC(=O)N1CCN(c2nc(Nc3ccc(C(=O)NS(=O)(=O)C4(CN(C)C)CC4)cc3)nc(OCC(F)(F)F)n2)CC1] | 600.62 | 601.18 |
| 8025 | 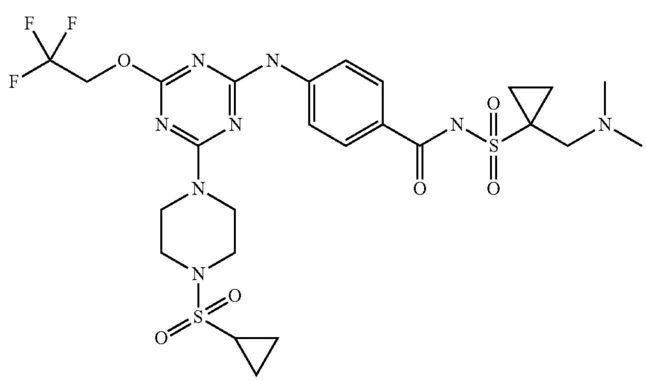 [SMILES: CN(C)CC1(S(=O)(=O)NC(=O)c2ccc(Nc3nc(OCC(F)(F)F)nc(N4CCN(S(=O)(=O)C5CC5)CC4)n3)cc2)CC1] | 662.71 | 663.20 |
| 8026 | 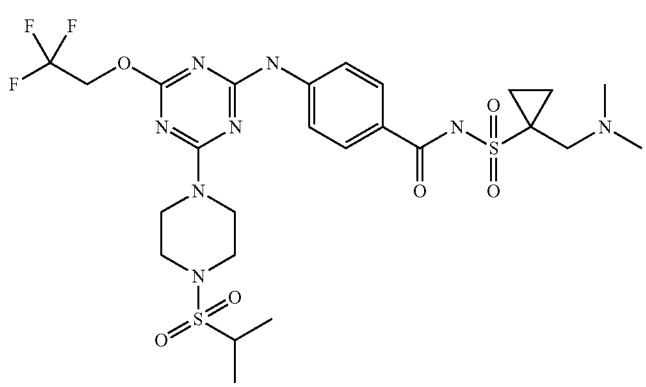 [SMILES: CC(C)S(=O)(=O)N1CCN(c2nc(Nc3ccc(C(=O)NS(=O)(=O)C4(CN(C)C)CC4)cc3)nc(OCC(F)(F)F)n2)CC1] | 664.73 | 665.23 |

TABLE 3-continued

| Examples | Structure | MW | LM/MS, MS m/z (M+ +H) Condition B |
|---|---|---|---|
| 8027 | 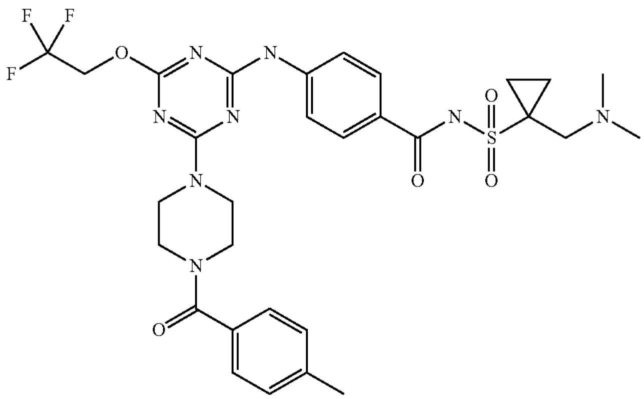 [SMILES: Cc1ccc(C(=O)N2CCN(c3nc(Nc4ccc(C(=O)NS(=O)(=O)C5(CN(C)C)CC5)cc4)nc(OCC(F)(F)F)n3)CC2)cc1] | 676.72 | 677.25 |
| 8028 | 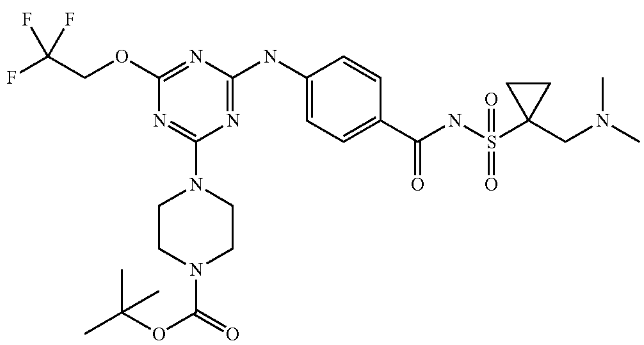 [SMILES: CN(C)CC1(S(=O)(=O)NC(=O)c2ccc(Nc3nc(OCC(F)(F)F)nc(N4CCN(C(=O)OC(C)(C)C)CC4)n3)cc2)CC1] | 658.70 | 659.20 |
| 8029 | 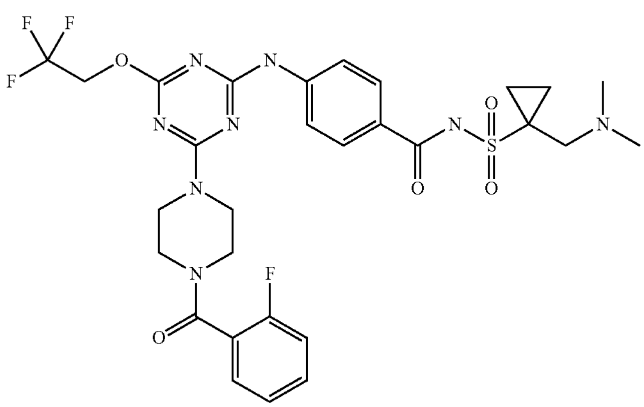 [SMILES: CN(C)CC1(S(=O)(=O)NC(=O)c2ccc(Nc3nc(OCC(F)(F)F)nc(N4CCN(C(=O)c5ccccc5F)CC4)n3)cc2)CC1] | 680.68 | 681.27 |
| 8030 | 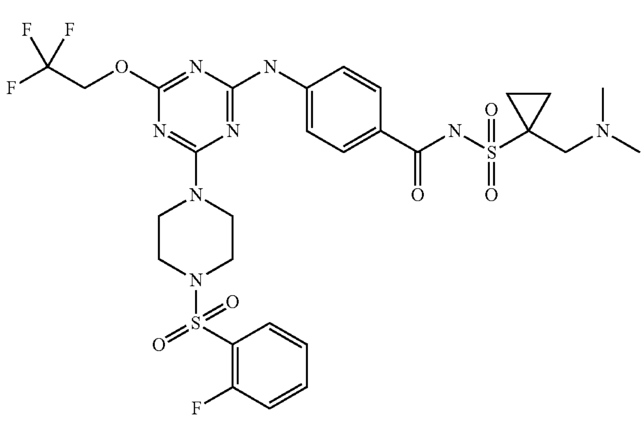 [SMILES: CN(C)CC1(S(=O)(=O)NC(=O)c2ccc(Nc3nc(OCC(F)(F)F)nc(N4CCN(S(=O)(=O)c5ccccc5F)CC4)n3)cc2)CC1] | 716.74 | 717.26 |

TABLE 3-continued

| Examples | Structure | MW | LM/MS, MS m/z (M+ +H) Condition B |
|---|---|---|---|
| 8031 | 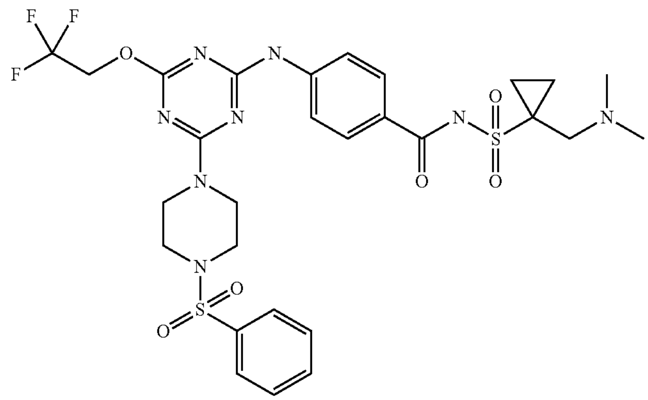 [SMILES: CN(C)CC1(S(=O)(=O)NC(=O)c2ccc(Nc3nc(OCC(F)(F)F)nc(N4CCN(S(=O)(=O)c5ccccc5)CC4)n3)cc2)CC1] | 698.75 | 699.25 |
| 8032 | 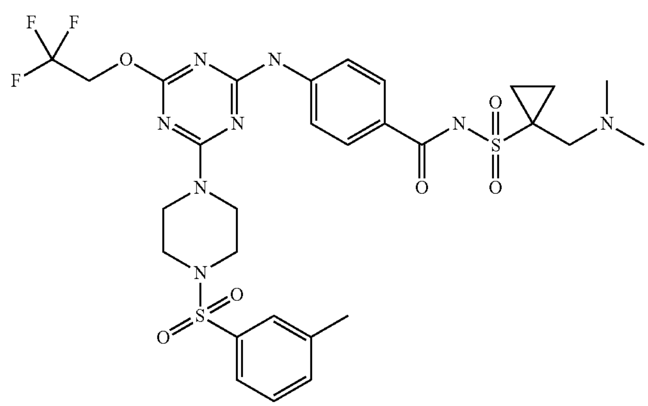 [SMILES: Cc1cccc(S(=O)(=O)N2CCN(c3nc(Nc4ccc(C(=O)NS(=O)(=O)C5(CN(C)C)CC5)cc4)nc(OCC(F)(F)F)n3)CC2)c1] | 712.77 | 713.27 |
| 8033 | 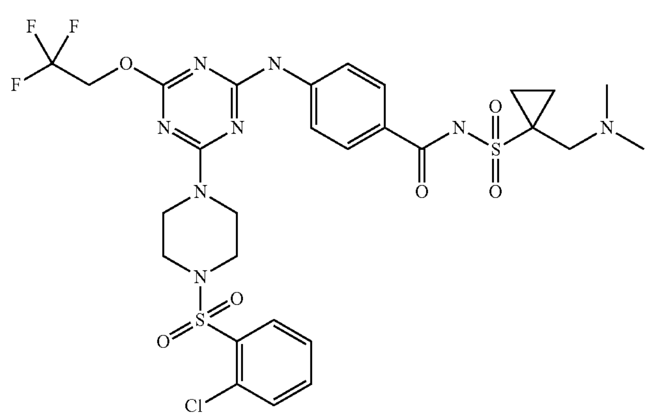 | 733.19 | 733.12 |

TABLE 3-continued
| Examples | Structure | MW | LM/MS, MS m/z (M+ +H) Condition B |
|---|---|---|---|
| 8034 | 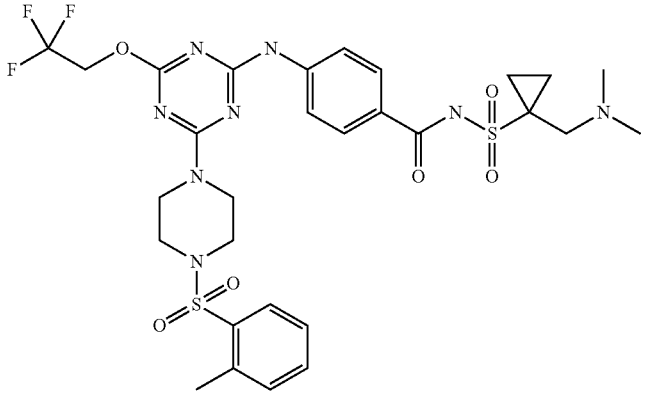 [SMILES: Cc1ccccc1S(=O)(=O)N1CCN(c2nc(Nc3ccc(C(=O)NS(=O)(=O)C4(CN(C)C)CC4)cc3)nc(OCC(F)(F)F)n2)CC1] | 712.77 | 713.18 |
| 8035 | 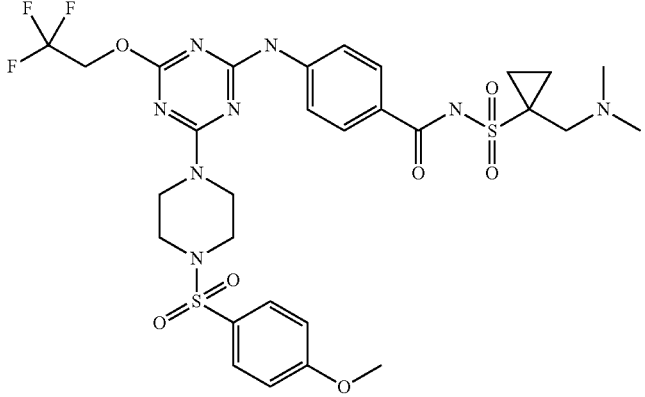 [SMILES: COc1ccc(S(=O)(=O)N2CCN(c3nc(Nc4ccc(C(=O)NS(=O)(=O)C5(CN(C)C)CC5)cc4)nc(OCC(F)(F)F)n3)CC2)cc1] | 728.77 | 729.19 |
| 8036 | 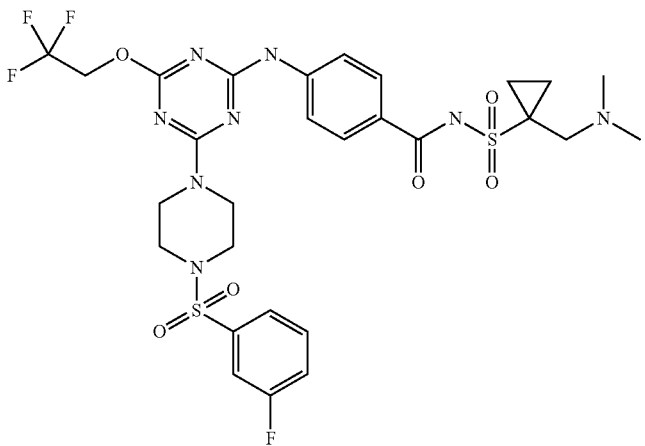 [SMILES: CN(C)CC1(S(=O)(=O)NC(=O)c2ccc(Nc3nc(OCC(F)(F)F)nc(N4CCN(S(=O)(=O)c5cccc(F)c5)CC4)n3)cc2)CC1] | 716.74 | 717.14 |

TABLE 3-continued

| Examples | Structure | MW | LM/MS, MS m/z (M+ +H) Condition B |
|---|---|---|---|
| 8037 | 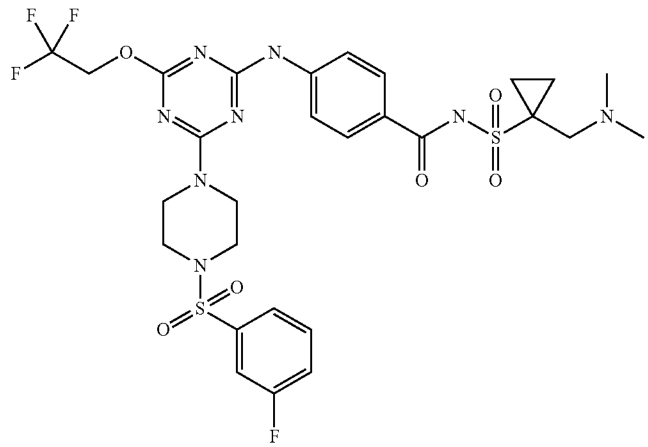 [SMILES: CN(C)CC1(S(=O)(=O)NC(=O)c2ccc(Nc3nc(OCC(F)(F)F)nc(N4CCN(S(=O)(=O)c5cccc(F)c5)CC4)n3)cc2)CC1] | 716.74 | 717.14 |
| 8038 | 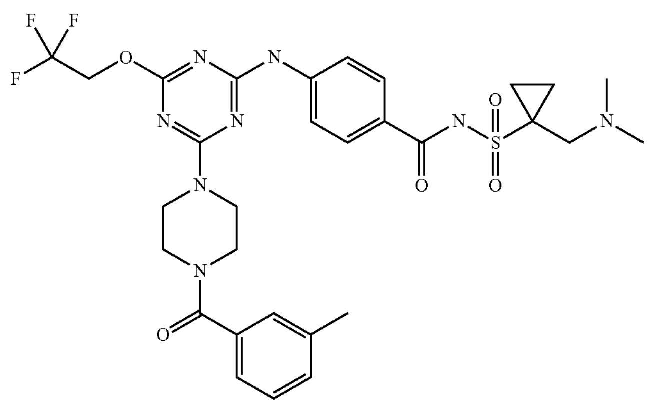 [SMILES: Cc1cccc(C(=O)N2CCN(c3nc(Nc4ccc(C(=O)NS(=O)(=O)C5(CN(C)C)CC5)cc4)nc(OCC(F)(F)F)n3)CC2)c1] | 676.72 | 677.18 |
| 8039 | 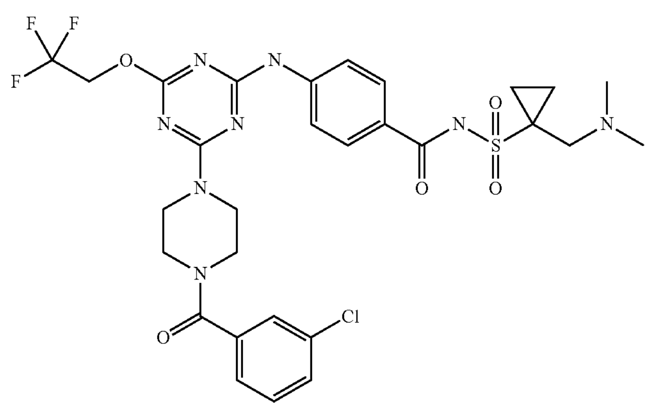 | 697.14 | 697.10 |

TABLE 3-continued

| Examples | Structure | MW | LM/MS, MS m/z (M+ +H) Condition B |
|---|---|---|---|
| 8040 | 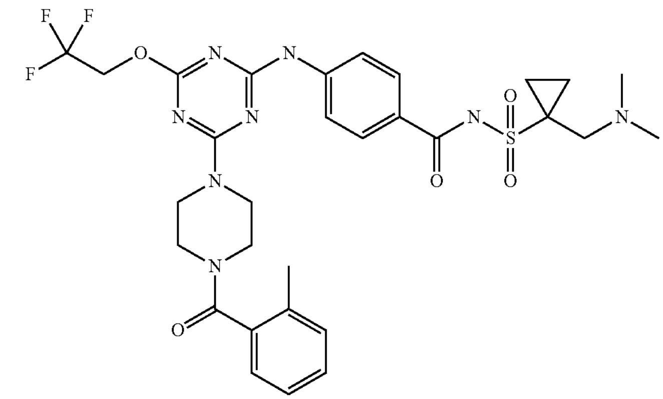 [SMILES: Cc1ccccc1C(=O)N1CCN(c2nc(Nc3ccc(C(=O)NS(=O)(=O)C4(CN(C)C)CC4)cc3)nc(OCC(F)(F)F)n2)CC1] | 676.72 | 677.18 |
| 8041 | 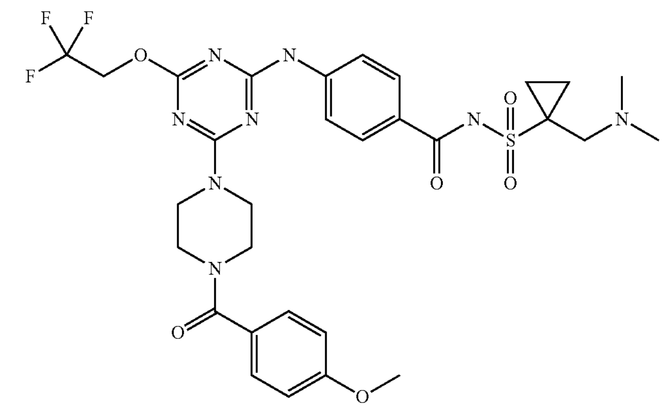 [SMILES: COc1ccc(C(=O)N2CCN(c3nc(Nc4ccc(C(=O)NS(=O)(=O)C5(CN(C)C)CC5)cc4)nc(OCC(F)(F)F)n3)CC2)cc1] | 692.72 | 693.16 |
| 8042 | 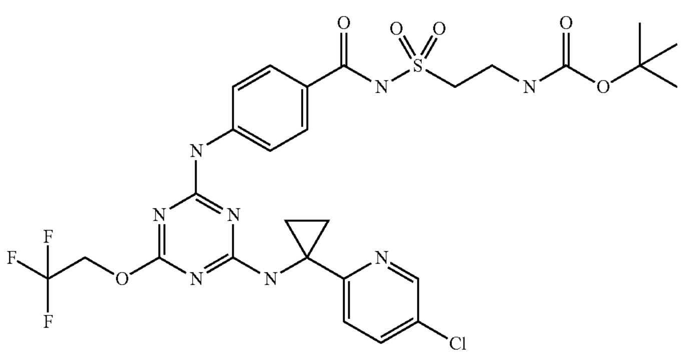 [SMILES: CC(C)(C)OC(=O)NCCS(=O)(=O)NC(=O)c1ccc(Nc2nc(NC3(c4ccc(Cl)cn4)CC3)nc(OCC(F)(F)F)n2)cc1] | 687.10 | 687.1 (condition A) |
| 8043 | 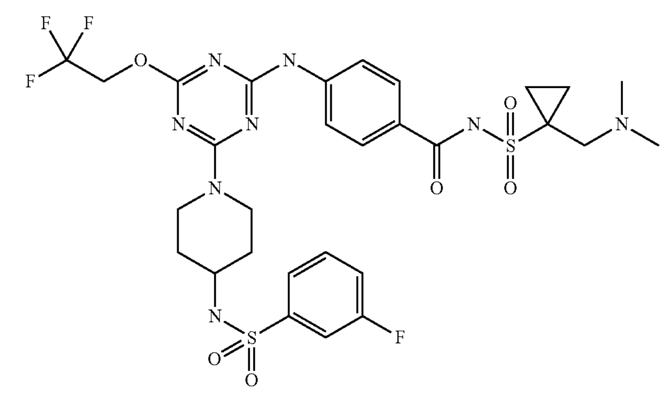 [SMILES: CN(C)CC1(S(=O)(=O)NC(=O)c2ccc(Nc3nc(OCC(F)(F)F)nc(N4CCC(NS(=O)(=O)c5cccc(F)c5)CC4)n3)cc2)CC1] | 730.76 | 731.24 |

TABLE 3-continued

| Examples | Structure | MW | LM/MS, MS m/z (M+ +H) Condition B |
|---|---|---|---|
| 8044 | 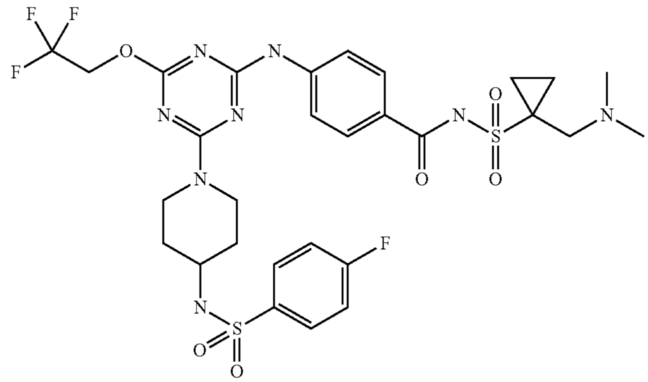 | 730.76 | 731.25 |
| 8045 | 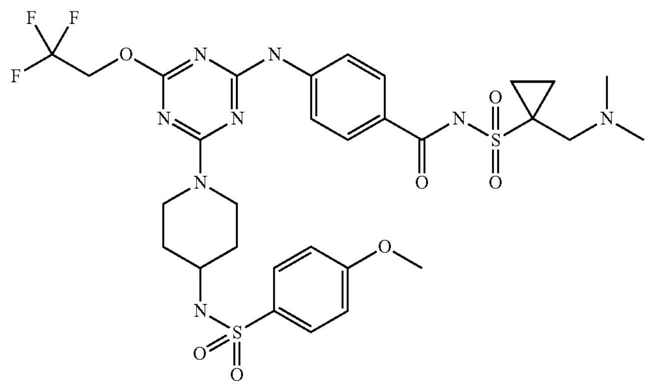 [SMILES: COc1ccc(S(=O)(=O)NC2CCN(c3nc(Nc4ccc(C(=O)NS(=O)(=O)C5(CN(C)C)CC5)cc4)nc(OCC(F)(F)F)n3)CC2)cc1] | 742.80 | 743.25 |
| 8046 | 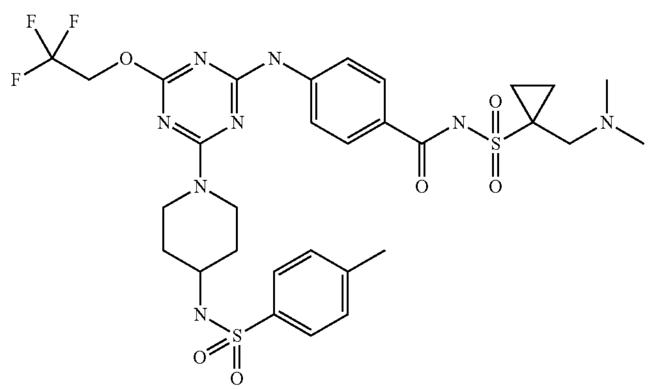 [SMILES: Cc1ccc(S(=O)(=O)NC2CCN(c3nc(Nc4ccc(C(=O)NS(=O)(=O)C5(CN(C)C)CC5)cc4)nc(OCC(F)(F)F)n3)CC2)cc1] | 726.80 | 727.26 |
| 8047 | 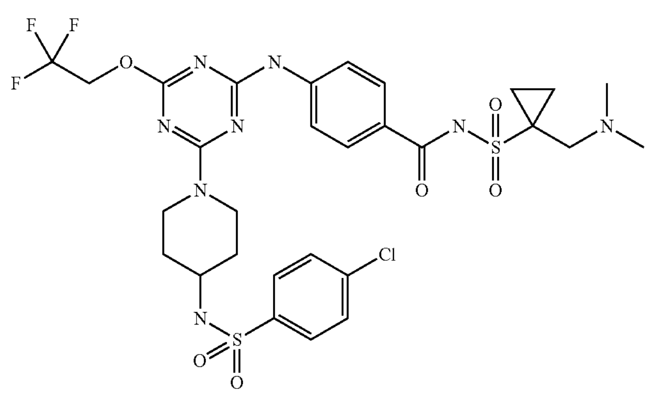 | 747.22 | 747.20 |

We claim:
1. A compound of formula I

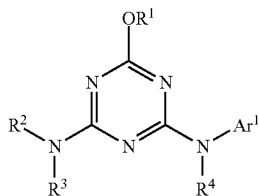

where
Ar¹ is phenyl substituted with 1 CON(R⁵)(R⁶) and with 0-3 substituents selected from halo and alkyl;
Ar² is phenyl substituted with 0-3 substituents selected from halo, alkyl, alkoxy, alkenyl, alkenyloxy, or CON(R⁷)(R⁸);
Ar³ is phenyl substituted with 0-3 substituents selected from halo, alkyl, and alkoxy;
Ar⁴ is phenyl or pyridinyl and is substituted with 0-3 substituents selected from halo, alkyl, and alkoxy;
R¹ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
R² is (Ar²)cycloalkyl;
R³ is hydrogen;
R⁴ is hydrogen;
R⁵ is (R¹⁰)alkyl, ((R¹⁰)cycloalkyl)alkyl, ((R¹⁰)alkyl)cycloalkyl, (((R¹⁰)alkyl)cycloalkyl), alkylSO₂, haloalkylSO₂, (cycloalkyl)alkylSO₂, alkenylSO₂, cycloalkylSO₂, (alkyl)cycloalkylSO₂, (R¹⁰)alkylSO₂, ((R¹⁰)cycloalkyl)alkylSO₂, ((R¹⁰)alkyl)cycloalkylSO₂, (((R¹⁰)alkyl)cycloalkyl)SO₂, Ar⁴SO₂, (R¹¹)(R¹²)NSO₂, or R¹³;
R⁶ is hydrogen or alkyl;
R⁷ is alkylSO₂, cycloalkylSO₂, or (Ar³)SO₂;
R⁸ is hydrogen or alkyl;
R⁹ is alkylCO, cycloalkylCO, (Ar³)CO, alkylCO₂, cycloalkylCO₂, alkylSO₂, cycloalkylSO₂, or (Ar³)SO₂;
R¹⁰ is hydrogen, halo, OR¹⁴, N(R¹⁵)(R¹⁶), CON(R¹⁷)(R¹⁸), SO₂N(R¹⁹)(R²⁰), or Ar⁴;
R¹¹ is hydrogen or alkyl;
R¹² is hydrogen or alkyl;
R¹³ is azetidinyl, pyrrolidinyl, piperidinyl, piperazinyl, or morpholinyl, and is substituted with 1 CON(R¹⁷)(R¹⁸) and with 0-2 substituents selected from alkyl, alkylCO and alkoxyCO;
or R¹³ is aminoalkyl and is substituted with 1 CON(R¹⁷)(R¹⁸) and with 0-2 substituents selected from alkyl, alkylCO and alkoxyCO;
or R¹³ is (imidazolyl)alkyl and is substituted with 1 CON(R¹⁷)(R¹⁸) and with 0-1 alkyl substituent;
R¹⁴ is hydrogen, alkyl, alkylCO, alkoxyCO, alkylaminoCO, or (Ar⁴)NHCO;
R¹⁵ is hydrogen, alkyl, cycloalkyl, (Ar⁴)alkyl, alkylCO, halolalkylCO, alkoxyCO, alkylNHCO, Ar⁴CO, alkylNHCO, Ar⁴NHCO, Ar⁴, (N-BOC-pyrrolidinyl)carboxyl or (N-BOC-piperidinyl)carboxyl;
R¹⁶ is hydrogen, alkyl;
or R¹⁵ and R¹⁶ taken together with the nitrogen to which they are attached is azetidinyl, pyrrolidinyl, piperidinyl, piperazinyl, or morpholinyl, and is substituted with 0-2 substituents selected from alkyl, alkylCO and Ar⁴;
or R¹⁵ and R¹⁶ taken together with the nitrogen to which they are attached is a [1-4.0-3.1-4] bridged bicyclic amine and is substituted with 0-3 substituents selected from alkyl, carboxy, alkoxycarbonyl, and carboxamido;
R¹⁷ is hydrogen, alkyl, alkylSO₂, haloalkylSO₂, hydroxyalkylSO₂, alkoxyalkylSO₂, (cycloalkyl)alkylSO₂, alkenylSO₂, cycloalkylSO₂, (alkyl)cycloalkylSO₂, SO₂N(R¹⁹)(R²⁰), Ar⁴, or R²¹;
R¹⁸ is hydrogen or alkyl;
or R¹⁷ and R¹⁸ taken together with the nitrogen to which they are attached is azetidinyl, pyrrolidinyl, piperidinyl, piperazinyl, or morpholinyl, and is substituted with 0-2 substituents selected from alkyl, alkylCO or Ar⁴;
or R¹⁷ and R¹⁸ taken together with the nitrogen to which they are attached is a [1-4.0-3.1-4] bridged bicyclic amine and is substituted with 0-3 substituents selected from alkyl, carboxy, alkoxycarbonyl, and carboxamido;
R¹⁹ is hydrogen, alkyl, cycloalkyl, (Ar⁴)alkyl, alkylCO, halolalkylCO, alkoxyCO, cycloalkylCO, alkylNHCO, Ar⁴CO, alkylNHCO, Ar⁴NHCO, Ar⁴, (N-BOC-piperidinyl)carboxamido, or (N-BOC-pyrrolidinyl)carboxamide;
R²⁰ is hydrogen or alkyl;
R²¹ is alkyl or cycloalkyl and is substituted with 1 CON(R²²)(R²³) and with 0-2 substituents selected from halo, alkyl, haloalkyl, alkenyl, cycloalkyl, and halocycloalkyl;
R²² is hydrogen, alkyl, alkylSO₂, haloalkylSO₂, hydroxyalkylSO₂, alkoxyalkylSO₂, (cycloalkyl)alkylSO₂, alkenylSO₂, cycloalkylSO₂, (alkyl)cycloalkylSO₂, SO₂N(R¹⁹)(R²⁰), or Ar⁴; and
R²³ is hydrogen or alkyl;
or a pharmaceutically acceptable salt thereof.

2. A compound of claim 1 where R¹ is haloalkyl or a pharmaceutically acceptable salt thereof.

3. A compound of claim 1 where R¹ is trifluoroethyl or a pharmaceutically acceptable salt thereof.

4. A compound of claim 1 where R⁵ is alkylSO₂, haloalkylSO₂, (cycloalkyl)alkylSO₂, alkenylSO₂, cycloalkylSO₂, (alkyl)cycloalkylSO₂, (R¹⁰)alkylSO₂, ((R¹⁰)cycloalkyl)alkylSO₂, ((R¹⁰)alkyl)cycloalkylSO₂, (((R¹⁰)alkyl)cycloalkyl)SO₂, Ar⁴SO₂, or (R¹¹)(R¹²)NSO₂; or a pharmaceutically acceptable salt thereof.

5. A compound of claim 1 where R⁵ is (R¹⁰)alkyl, ((R¹⁰)cycloalkyl)alkyl, ((R¹⁰)alkyl)cycloalkyl, or (((R¹⁰)alkyl)cycloalkyl); CON(R¹⁷)(R¹⁸) or SO₂N(R¹⁹)(R²⁰); R¹⁷ is alkylSO₂, haloalkylSO₂, hydroxyalkylSO₂, alkoxyalkylSO₂, (cycloalkyl)alkylSO₂, alkenylSO₂, cycloalkylSO₂, (alkyl)cycloalkylSO₂, or SO₂N(R¹⁹)(R²⁰); and R¹⁹ is alkylCO, halolalkylCO, alkoxyCO, cycloalkylCO, alkylNHCO, Ar⁴CO, alkylNHCO, or Ar⁴NHCO; or a pharmaceutically acceptable salt thereof.

6. A compound of claim 1 where R⁵ is (R¹⁰)alkyl, ((R¹⁰)cycloalkyl)alkyl, ((R¹⁰)alkyl)cycloalkyl, or (((R¹⁰)alkyl)cycloalkyl); R¹⁰ is CON(R¹⁷)(R¹⁸); R¹⁷ is R²¹; and R²² is alkylSO₂, haloalkylSO₂, hydroxyalkylSO₂, alkoxyalkylSO₂, (cycloalkyl)alkylSO$_2$, alkenylSO$_2$, cycloalkylSO$_2$, (alkyl)cycloalkylSO$_2$, or)SO$_2$N(R$^{19}$)(R$^{20}$); or a pharmaceutically acceptable salt thereof.

7. A compound of claim 1 where R$^2$ is (Ar$^2$)cycloalkyl where Ar$^2$ is substituted with 0-2 substituents selected from halo, alkyl, alkoxy, alkenyl, and alkenyloxy, and substituted with 1 CON(R$^7$)(R$^8$); or a pharmaceutically acceptable salt thereof.

8. A composition comprising a compound of claim 1, or a pharmaceutically acceptable salt thereof, and a pharmaceutically acceptable carrier.

9. A method of treating hepatitis C infection comprising administering a therapeutically effective amount of a compound of claim 1 to a patient.

\* \* \* \* \*

UNITED STATES PATENT AND TRADEMARK OFFICE
CERTIFICATE OF CORRECTION

PATENT NO. : 8,765,944 B2  
APPLICATION NO. : 13/210776  
DATED : July 1, 2014  
INVENTOR(S) : Li-Qiang Sun et al.

Page 1 of 1

It is certified that error appears in the above-identified patent and that said Letters Patent is hereby corrected as shown below:

In the Specification:

Column 10, line 44, change "Imiqimod," to -- Imiquimod, --.

Column 10, line 44, change "5′-monophospate" to -- 5′-monophosphate --.

Column 11, line 25, change "Imiqimod," to -- Imiquimod, --.

Column 11, line 25, change "5′-monophospate" to -- 5′-monophosphate --.

In the Claims:

Claim 5:

Column 190, line 57, change "$CON(R^{17})(R^{18})$" to -- $R^{10}$ is $CON(R^{17})(R^{18})$ --.

Claim 6:

Column 191, line 2, change "or)$SO_2N(R^{19})(R^{20})$;" to -- or $SO_2N(R^{19})(R^{20})$; --.

Signed and Sealed this  
Twenty-first Day of April, 2015

Michelle K. Lee  
*Director of the United States Patent and Trademark Office*